US010717930B2

(12) United States Patent
King et al.

(10) Patent No.: US 10,717,930 B2
(45) Date of Patent: *Jul. 21, 2020

(54) LYSINE AND PROLINE BASED FLAME RETARDANTS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/359,024

(22) Filed: Mar. 20, 2019

(65) Prior Publication Data
US 2019/0211267 A1 Jul. 11, 2019

Related U.S. Application Data

(63) Continuation of application No. 15/726,248, filed on Oct. 5, 2017, now Pat. No. 10,329,488.

(51) Int. Cl.
*C09K 21/10* (2006.01)
*C08K 5/5317* (2006.01)
(Continued)

(52) U.S. Cl.
CPC ............ *C09K 21/10* (2013.01); *C07C 211/12* (2013.01); *C07D 207/04* (2013.01); *C08G 79/04* (2013.01);
(Continued)

(58) Field of Classification Search
CPC ........ C09K 21/10; C09K 21/04; C08K 3/016; C08K 3/32; C08K 2003/329; C07D 207/04; C08G 79/04; C07C 211/12
See application file for complete search history.

(56) References Cited

U.S. PATENT DOCUMENTS

2014/0275311 A1 9/2014 Marks et al.

FOREIGN PATENT DOCUMENTS

CN 104072803 A 10/2014

OTHER PUBLICATIONS

Metkar et al., "Lysinol: a renewably resourced alternative to petrochemical polyamines and aminoalcohols," Green Chemistry 16.10 (2014): 4575-4586, http://www.academia.edu/download/40763096/GreenChem_2014.pdf.
(Continued)

*Primary Examiner* — Andrew J. Oyer
(74) *Attorney, Agent, or Firm* — James L. Olsen

(57) ABSTRACT

A flame retardant lysine-based derivative, a process for forming a flame retardant lysine-based derivative, and an article of manufacture comprising a flame retardant lysine-based derivative are disclosed. The flame retardant lysine-derived molecule can be synthesized from a bio-based source, and can have at least one phosphoryl or phosphonyl moiety. A flame retardant proline-based derivative, a process for forming a flame retardant proline-based derivative, and an article of manufacture comprising a flame retardant proline-based derivative are also disclosed. The flame retardant proline-derived molecule can be synthesized from a bio-based source and can have at least one phosphoryl or phosphonyl moiety.

7 Claims, 39 Drawing Sheets

(51) Int. Cl.
*C08K 5/5313* (2006.01)
*C08K 3/016* (2018.01)
*C07D 207/04* (2006.01)
*C08K 3/32* (2006.01)
*C08G 79/04* (2006.01)
*C07C 211/12* (2006.01)
*C09K 21/04* (2006.01)
*C08G 59/32* (2006.01)
*C08L 5/00* (2006.01)
C08K 5/00 (2006.01)

(52) U.S. Cl.
CPC ............ *C08K 3/016* (2018.01); *C08K 3/32* (2013.01); *C08K 5/5313* (2013.01); *C08K 5/5317* (2013.01); *C09K 21/04* (2013.01); *C08G 59/3227* (2013.01); *C08G 59/3272* (2013.01); *C08K 5/0066* (2013.01); *C08K 2003/329* (2013.01)

(56) References Cited

OTHER PUBLICATIONS

Yang et al., "Copper-Catalyzed Synthesis of Medium- and Large-sized Nitrogen Heterocycles via N-Arylation of Phosphoramidates and Carbamates," Organic Letters, 2005, vol. 7, No. 21, pp. 4781-4784.

King et al., "Lysine and Proline Based Flame Retardants", U.S. Appl. No. 15/726,248, filed Oct. 5, 2017.

IBM, List of IBM Patents or Patent Applications Treated as Related, Mar. 20, 2019, 2 pages.

410 2-Mercaptoethanol

420 Cysteamine HCl 430 3-Mercaptopropionate

A: Thiol-ene with 345, MeOH, UV
B: Thiol-ene with 375, MeOH, UV, pH 8-11
C: Thiol-ene with 360, UV A: Thiol-ene with 345, MeOH, UV
B: Thiol-ene with 375, MeOH, UV, pH 8-11
C: Thiol-ene with 360, UV A: Thiol-ene with 345, MeOH, UV
B: Thiol-ene with 375, MeOH, UV, pH 8-11
C: Thiol-ene with 360, UV A: Thiol-ene with 410, UV
B: Thiol-ene with 420, MeOH, UV, pH 8-11
C: Thiol-ene with 430, MeOH, UV A: Thiol-ene with 410, UV
B: Thiol-ene with 420, MeOH, UV, pH 8-11
C: Thiol-ene with 430, MeOH, UV A: Thiol-ene with 410, UV
B: Thiol-ene with 420, MeOH, UV, pH 8-11
C: Thiol-ene with 430, MeOH, UV A: Thiol-ene with 410, UV
B: Thiol-ene with 420, MeOH, UV, pH 8-11
C: Thiol-ene with 430, MeOH, UV

LYSINE AND PROLINE BASED FLAME RETARDANTS

BACKGROUND

The present disclosure relates generally to the field of bio-renewable compounds, and more particularly, to bio-renewable flame retardants.

Bio-based, sustainable compounds can be used in the syntheses of substances that previously required petroleum-based raw materials. For example, bio-based compounds can be used in polymers, flame retardants, cross-linkers, etc. There are numerous strategies for efficiently and inexpensively producing bio-based compounds on an industrial scale. These strategies can include fermentation technologies, membrane technologies, and genetic engineering, to name a few.

SUMMARY

A flame retardant lysine-based derivative, a process for forming a flame retardant lysine-based derivative, and an article of manufacture comprising a flame retardant lysine-based derivative are disclosed. The flame retardant lysine-derived molecule can be synthesized from a bio-based source and can have at least one phosphoryl or phosphonyl moiety. A flame retardant proline-based derivative, a process for forming a flame retardant proline-based derivative, and an article of manufacture comprising a flame retardant proline-based derivative are also disclosed. The flame retardant proline-derived molecule can be synthesized from a bio-based source and can have at least one phosphoryl or phosphonyl moiety.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

Figure 1:
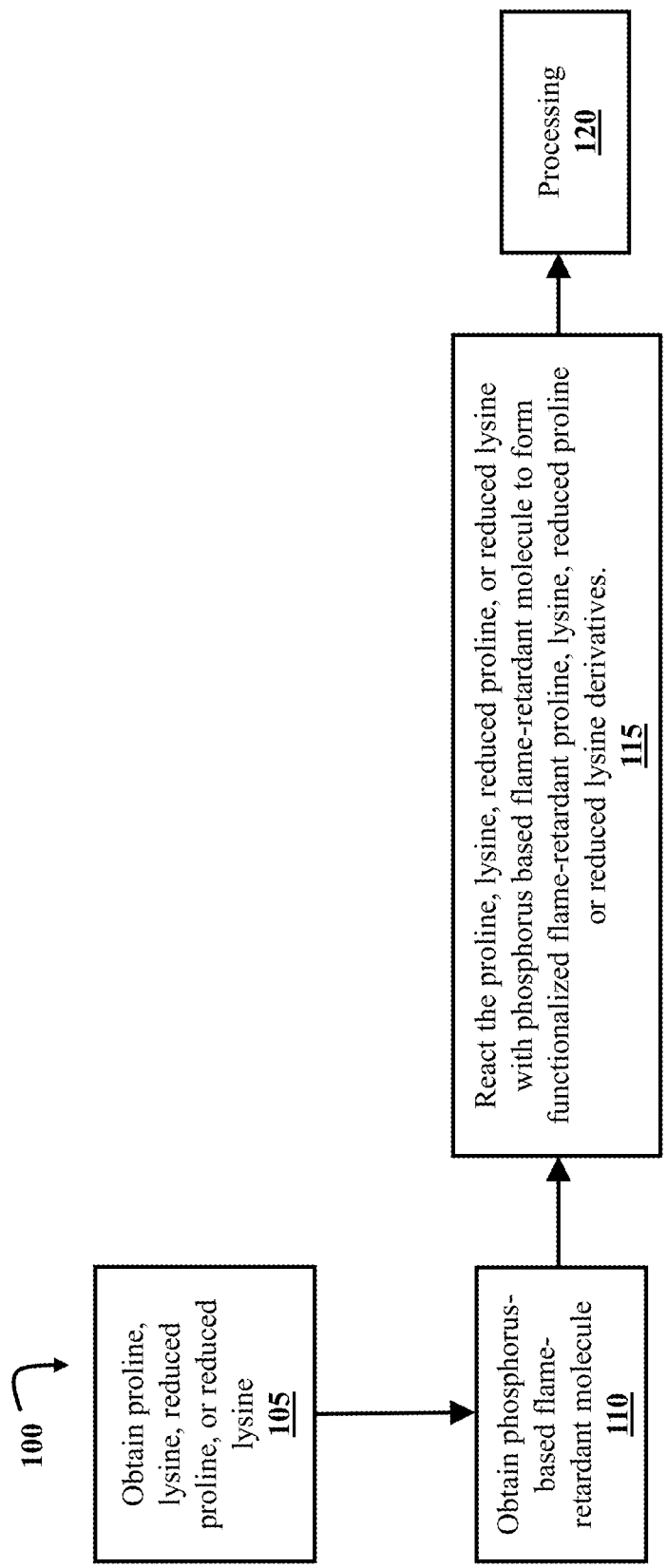
FIG. 1 is a flow diagram illustrating a process of forming a flame retardant polymer containing proline-derived or lysine-derived molecules, in accordance with embodiments of the present disclosure.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the invention.

DETAILED DESCRIPTION

Aspects of the present disclosure relate generally to the field of bio-renewable compounds, and more particularly, to bio-renewable flame retardants. While the present disclosure is not necessarily limited to such applications, various aspects of the disclosure may be appreciated through a discussion of various examples using this context.

Bio-based compounds are increasingly being used in the syntheses of substances that previously required petroleum-based raw materials. One benefit of bio-based compounds is that they are from renewable resources. Therefore, these compounds have applications in sustainable, or "green," materials. Sustainable materials are becoming more and more prevalent due to the rising costs of fossil fuels and increasing environmental regulatory controls. Advances in biotechnology have provided numerous strategies for efficiently and inexpensively producing bio-based compounds on an industrial scale. For example, these strategies can be found in fermentation technologies, membrane technologies, and genetic engineering. Two approaches that can use biotechnologies are plant-based and microorganism-based approaches. Plant-based approaches can involve obtaining a material directly from a plant, or growing plant tissues or cells that can produce bio-based compounds from various substrates using their own biosynthetic pathways. Microorganism-based approaches involve using native or genetically modified fungi, yeast, or bacteria to produce a desired compound from a structurally similar substrate.

Bio-based compounds can be used in a variety of applications. For example, bio-based compounds can be used in polymers, flame retardants, and cross-linkers. In some examples, bio-based polymers and petroleum-based polymers are blended to form a polymer composite. However, polymers can also be entirely bio-based, or produced from a combination of bio- and petroleum-based monomers. Bio-based compounds can impart flame retardant properties to bio- and petroleum-based polymers. For example, flame retardant molecules or cross-linkers can be incorporated into polymers. Additionally, flame retardant monomers can be polymerized to form flame retardant polymers.

Lysine, proline, and their reduced derivatives (2,6-diaminohexan-1-ol and pyrrolidin-2-ylmethanol, respectively) are examples of bio-based compounds that have applications as a component of various polymers, resins, and monomers. Lysine and proline are amino acids used in the biosynthesis of proteins. Lysine and proline can be naturally obtained from various biological sources, including: animal meat, legumes, vegetables, and eggs, to name a few. Lysine can be synthesized from caprolactam. Proline can be synthesized from diethyl malonate and acrylonitrile. Industrially, lysine is manufactured through fermentation using *Corynebacterium glutamicum*. This fermentation production exceeds 600,000 tons a year. Similarly, proline can be industrially produced through *Corynebacterium glutamicum* fermentation.

According to embodiments of the present disclosure, lysine, a reduced lysine derivative (2,6-diaminohexan-1-ol), proline, and a reduced proline derivative (pyrrolidin-2-ylmethanol) are used as a precursor for various flame retardant molecules (e.g., small molecules or functionalized molecules). The lysine, proline, reduced lysine, and reduced proline flame retardant molecules can be added to polymers, fabrics, resins, or other materials during blending, curing, foaming, extrusion, or other processing techniques. In addition to directly adding the lysine-derived and/or proline-derived flame retardants into the materials during processing, the flame retardants may be integrated into microcapsules. Lysine and reduced lysine-derived cross-linkers each have three functional R groups, which may bind to resins and/or polymers. Proline and reduced proline-derived cross-linkers each have two functional R groups, which may bind to resins and/or polymers. The addition of these cross-linkers causes a resin or polymer to be flame retardant. The lysine-derived and proline-derived molecules may be multifunctional (e.g., monofunctional or difunctional), depending on the number of functional R groups bound to the molecules.

FIG. 1 is a flow diagram illustrating a process 100 of forming a flame retardant polymer containing proline-derived or lysine-derived molecules, in accordance with embodiments of the present disclosure. Process 100 begins by obtaining proline, lysine, reduced proline, or reduced lysine at step 105. These molecules may be naturally obtained (e.g., from various biological sources) or synthesized from other biomolecules (e.g., lysine may be synthesized from caprolactam and proline may be synthesized from diethyl malonate or acrylonitrile). Further, reduced lysine and reduced proline may be synthesized from lysine and proline, respectively. At step 110, phosphorus-based flame retardant molecules are obtained. The phosphorus-based flame retardant molecules may have either a phosphoryl or a phosphonyl moiety (collectively referred to as an FR group) with an attached R functional group or phenyl (Ph) group. The R groups that are attached to the FR groups can vary, as is discussed in greater detail below. The phosphorus-based flame retardant molecules can be phosphate- or phosphonate-based flame retardant molecules. The structures and syntheses of phosphorus-based flame retardant molecules are discussed in greater detail with regard to FIGS. 2-3D.

After proline, lysine, reduced proline, or reduced lysine molecules and phosphorus-based flame retardant molecules are obtained at steps 105 and 110, respectively, the proline, lysine, reduced proline, or reduced lysine molecules are reacted with the phosphorus-based flame retardant molecules to form functionalized flame retardant proline, lysine, reduced proline, or reduced lysine-derived molecules at step 115. The structures and syntheses of the functionalized flame retardant molecules are discussed in greater detail with regard to FIGS. 6-12.

The structure of the functionalized flame retardant molecule formed at operation 115 is determined by the precursor (e.g., proline, lysine, reduced proline, and reduced lysine) and phosphorus-based flame retardant molecule used in the reaction. The phosphorus-based flame retardant molecule reacts with an amine, hydroxyl, and/or carboxylic acid group on the proline, lysine, reduced proline, or reduced lysine to provide an FR group with an attached R functional group. Examples of R groups can include phenyl substituents, epoxy functional groups, allyl functional groups, propylene carbonate substituents, hydroxyl-functionalized thioether substituents, amino-functionalized thioether substituents, carboxylic acid-functionalized thioether substituents, etc. The syntheses and structures of the functionalized flame retardant lysine-derived, reduced lysine-derived, proline derived, or reduced proline-derived molecules are discussed in greater detail with regard to FIGS. 6-12.

The proline, lysine, reduced proline, or reduced lysine derived flame retardant molecules are processed at step 120. The nature of the processing may depend on the identity of the flame retardant derivative. Processing 120 may include chemically reacting a functionalized (e.g., monofunctional, difunctional, trifunctional, etc.) flame retardant proline, lysine, reduced proline, or reduced lysine derived molecule with a polymer, forming a bond between the flame retardant and the polymer. In some embodiments, processing 120 may include adding a flame retardant proline, lysine, reduced proline, or reduced lysine small molecule to a polymer (e.g., during blending, extrusion, etc.). Examples of polymers include epoxies, polyhydroxyurethanes, polycarbonates, polyesters, polyacrylates, polyimides, polyamides, polyureas, poly(vinyl-esters), etc. The materials for these polymers can come from petroleum-based sources, bio-based sources, or a combination of petroleum- and bio-based sources. Further, in some embodiments, the flame retardant molecules can be used in non-polymeric applications, such as resins for varnishes and adhesives. Flame retardant lysine, reduced lysine, proline, or reduced proline monomers may be polymerized in a reaction with a base and/or second monomer. Additionally, in some embodiments, the monomers may be polymerized in a reaction with a Ziegler-Natta catalyst. Polymerizations reactions with the flame retardant monomers are discussed in greater detail with regard to FIG. 13.

Figure 2:
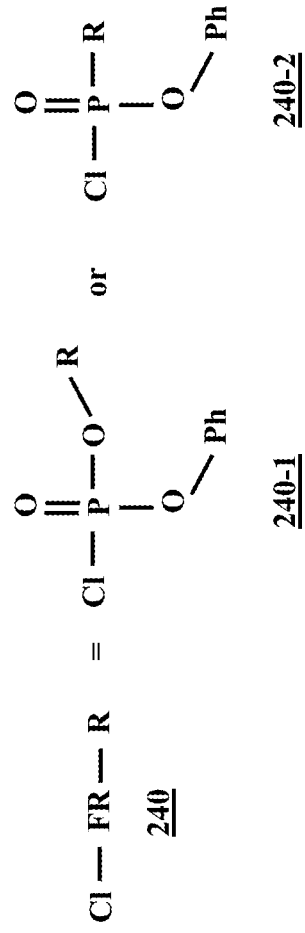
FIG. 2 is a diagrammatic representation of the molecular structures of generic phosphorus-based flame retardant molecules, in accordance with embodiments of the present disclosure.
Figure 2:
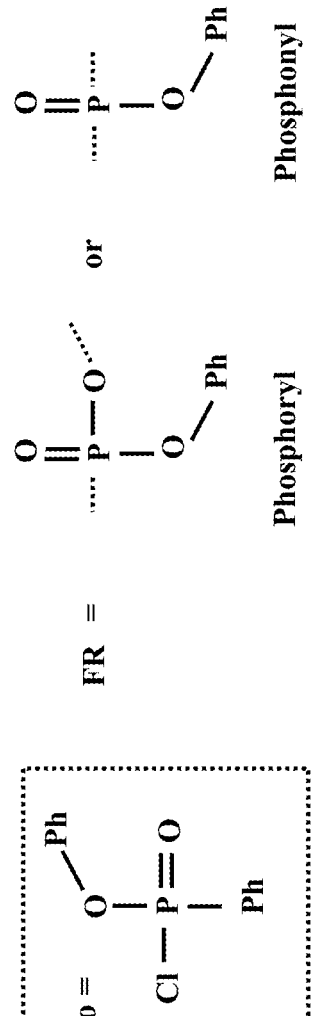
Figure 2:
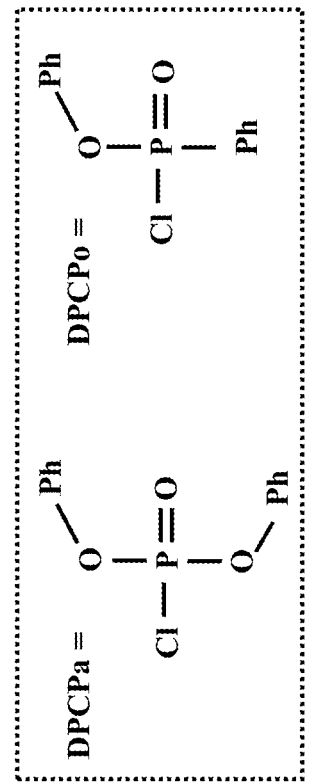

FIG. 2 is a diagrammatic representation of the molecular structures 202 of R-substituted phosphorus-based flame retardant molecules 240, in accordance with embodiments of the present disclosure. Each phosphorus-based flame retardant molecule 240 is either a phosphate-based flame retardant molecule 240-1 or a phosphonate-based flame retardant molecule 240-2. Herein, phosphoryl and phosphonyl moieties are replaced by the abbreviation "FR" in order to simplify illustrations of the molecular structures. Each phosphorus-based flame retardant molecule 240 has a phenyl (Ph) substituent and an R group. In some examples, the R group can bind to a resin. Further, the molecular structures of diphenyl chlorophosphate (DPCPa) and diphenylphosphinic chloride (DPCPo) are also illustrated in FIG. 2. DPCPa is a phosphate-based flame retardant molecule 240-1, where the R-substitute is a phenyl group. DPCPo is a phosphonate-based flame retardant molecule 240-2, where the R-substitute is a phenyl group. DPCPa and DPCPo may be used in forming various proline, reduced proline, lysine, and reduced lysine derived small molecules and functionalized molecules.

The identities of the R groups bound to the phosphorus-based flame retardant molecules 240 vary, and are discussed in greater detail with respect to FIGS. 3A-3D. Additionally, in some embodiments, the phenyl group is replaced by an alkyl substituent (e.g., methyl, ethyl, propyl, isopropyl, etc.). Further, in some embodiments, the phenyl groups present on diphenyl chlorophosphate (DPCPa) or diphenylphosphinic chloride (DPCPo) may be replaced by similar non-polar functional groups (e.g., methyl, ethyl, propyl, isopropyl, etc.) The syntheses of the phosphorus-based flame retardant molecules 240 are discussed with regard to FIGS. 3A-3D.

Figure 3A:
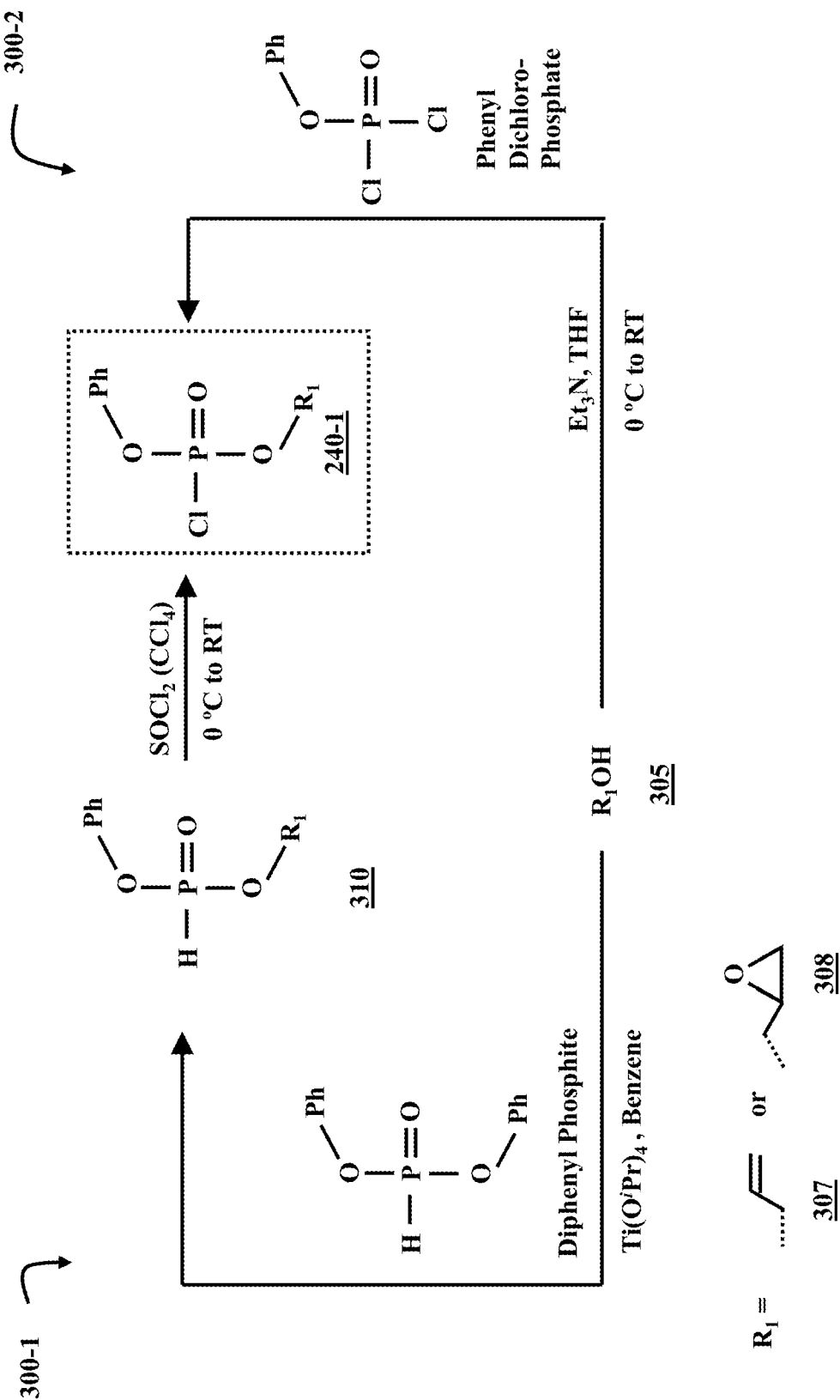
FIG. 3A is a chemical reaction diagram illustrating two processes of synthesizing the phosphate-based flame retardant molecule, in accordance with embodiments of the present disclosure.

FIG. 3A is a chemical reaction diagram illustrating two processes 300-1 and 300-2 of synthesizing the phosphate-based flame retardant molecule 240-1, in accordance with embodiments of the present disclosure. In both processes 300-1 and 300-2, an alcohol 305 is a starting material for the phosphate-based flame retardant molecule 240-1. The alcohol 305 has either an allyl $R_1$ group 307 or an epoxide $R_1$ group 308. It should be noted that, though an allyl group 307 with a single methylene spacer group is illustrated here, other alcohols with allylic chains of varying lengths (e.g., one to twelve methylene spacer groups) could be used. Additionally, alcohols with acrylate substituents are used in some embodiments.

In process 300-1, the alcohol 305 is reacted with diphenyl phosphite and titanium isopropoxide (Ti(O$^i$Pr)$_4$) in benzene to produce a precursor 310 to the phosphate-based flame retardant molecule 240-1. In this pseudo-transesterification reaction, the precursor 310 is formed when a phenyl (Ph) substituent on diphenyl phosphite is replaced by an allyl 307 or epoxide 308 $R_1$ group from the alcohol 305. The precursor 310 is then reacted with thionyl chloride (SOCl$_2$) and carbon tetrachloride (CCl$_4$) over a range of 0° C. to room temperature (RT), forming the phosphate-based flame retardant molecule 240-1.

In process 300-2, the alcohol 305 is reacted with phenyl dichlorophosphate in a tetrahydrofuran (THF) solution containing triethyl amine (Et$_3$N). This process is carried out over a range of 0° C. to room temperature (RT). A chloride on the phenyl dichlorophosphate is replaced by the alcohol 305, forming the phosphate-based flame retardant molecule 240-1 with an allyl 307 or epoxide 308 $R_1$ group.

Figure 3B:
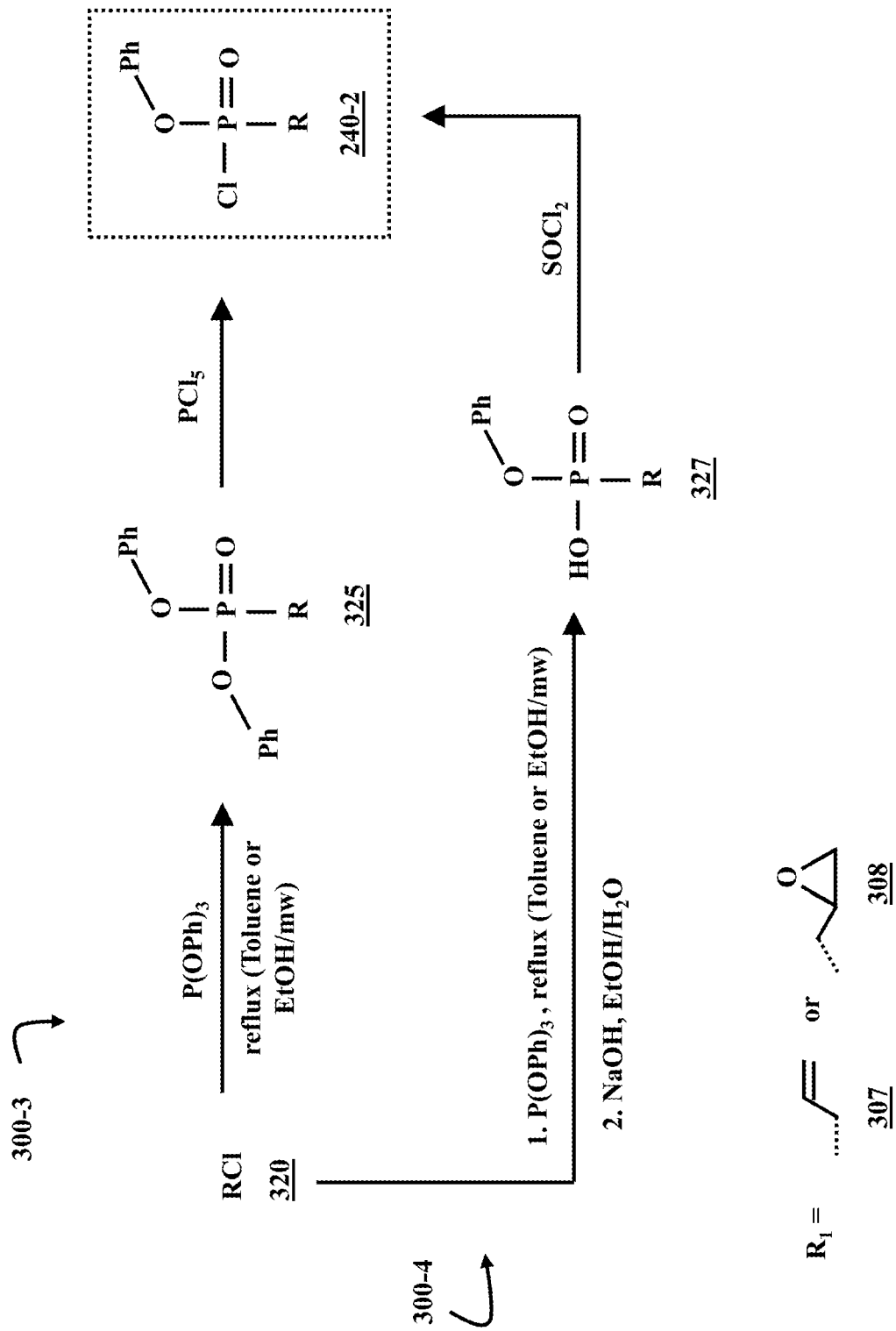
FIG. 3B is a chemical reaction diagram illustrating two processes of synthesizing the phosphonate-based flame retardant molecule, in accordance with embodiments of the present disclosure.

FIG. 3B is a chemical reaction diagram illustrating two processes 300-3 and 300-4 of synthesizing the phosphonate-based flame retardant molecule 240-2, in accordance with embodiments of the present disclosure. In both processes 300-3 and 300-4, an organochloride 320 is a starting material for the phosphonate-based flame retardant molecule 240-2. The organochloride has either an allyl $R_1$ group 307 or an epoxide $R_1$ group 308. It should be noted that, as in the case of the alcohol 305, other organochlorides with allylic chains of varying lengths (e.g., one to twelve methylene spacer groups) could be used. Additionally, organochlorides with acrylate substituents are used in some embodiments.

In process 300-3, the organochloride 320 is reacted with triphenyl phosphite (P(OPh)$_3$). The mixture is heated, either by refluxing in toluene or microwaving (mw) in ethanol (EtOH), producing a phosphonyl ester precursor 325 to the phosphonate-based flame retardant molecule 240-2. The phosphonyl ester precursor 325 is reacted with phosphorus pentachloride (PCl$_5$) to form the phosphonate-based flame retardant molecule 240-2 with an allyl 307 or epoxide 308 $R_1$ group.

In process 300-4, a mixture of the organochloride 320 and triphenyl phosphite (P(OPh)$_3$) is heated, either by refluxing in toluene or microwaving (mw) in ethanol (EtOH), forming a phenylphosphinic acid precursor 327 to the phosphonate-based flame retardant molecule 240-2. The reaction is then quenched by raising the pH of the solution. In this prophetic example, an ethanol (EtOH)/water (H$_2$O) solution of sodium hydroxide (NaOH) is added to the reaction mixture. However, in some embodiments, bases other than sodium hydroxide, such as potassium hydroxide or lithium hydroxide, are used to quench the reaction. When the reaction has been quenched, thionyl chloride (SOCl$_2$) is added to the phenylphosphinic acid precursor 327, producing the phosphonate-based flame retardant molecule 240-2 with an allyl 307 or epoxide 308 $R_1$ group.

Figure 3C:
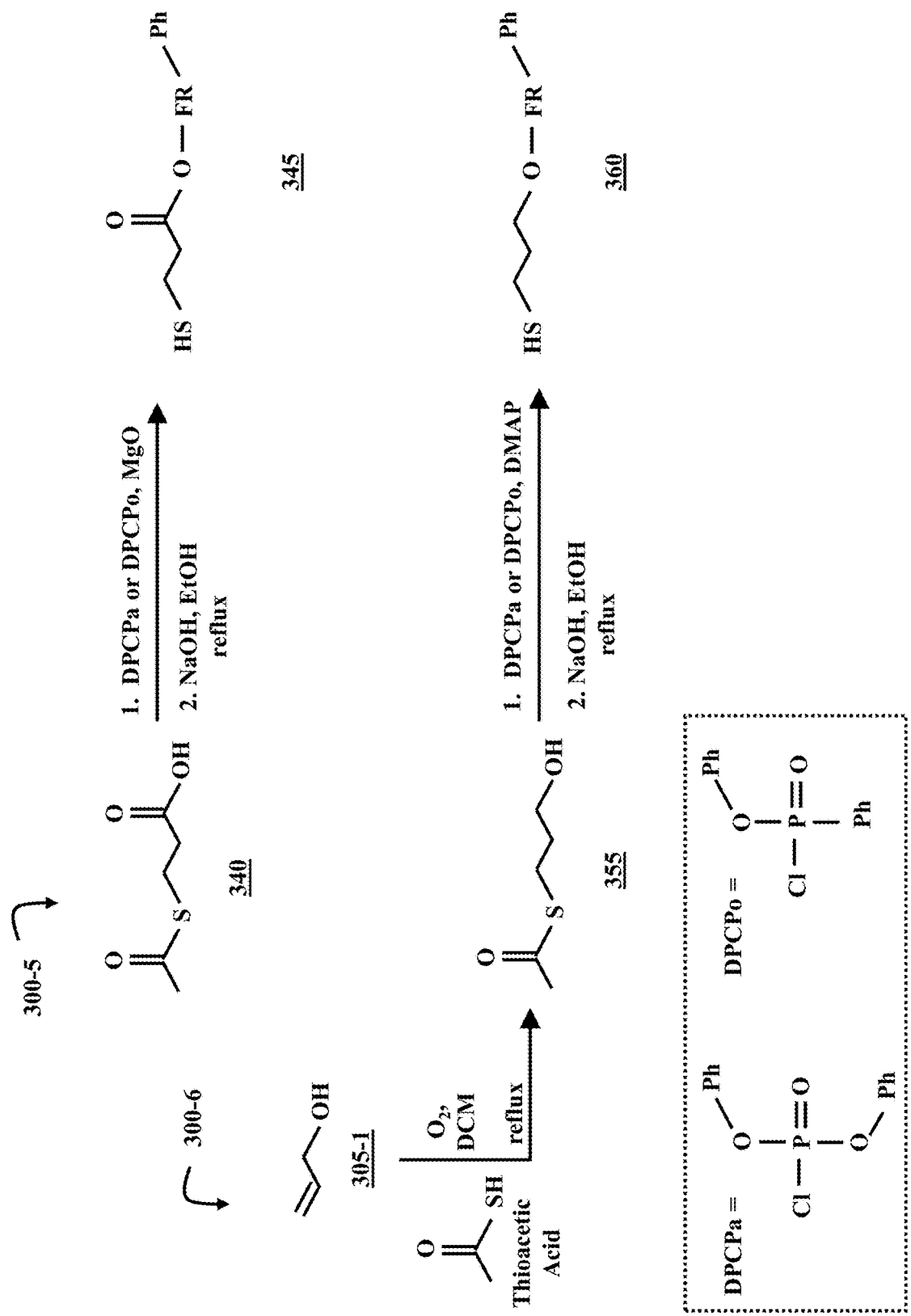
FIG. 3C is a chemical reaction diagram illustrating a process of synthesizing a carboxylic acid-derived flame retardant thiol molecule and a process of synthesizing a hydroxy-derived flame retardant thiol molecule, in accordance with embodiments of the present disclosure.

FIG. 3C is a chemical reaction diagram illustrating a process 300-5 of synthesizing a carboxylic acid-derived flame retardant thiol molecule 345 and a process 300-6 of synthesizing a hydroxy-derived flame retardant thiol molecule 360, in accordance with embodiments of the present disclosure. In process 300-5, acetate-protected thiopropionic acid 340 is reacted with magnesium oxide (MgO) and diphenyl chlorophosphate (DPCPa) or diphenylphosphinic chloride (DPCPo). The acetate group is then removed by refluxing the mixture in an ethanol (EtOH) solution containing sodium hydroxide (NaOH), yielding the carboxylic acid-derived flame retardant thiol molecule 345. If the process is carried out with DPCPa, the carboxylic acid-derived flame retardant thiol molecule 345 will have phosphoryl FR groups, and, if the reaction is carried out with DPCPo, the carboxylic acid-derived flame retardant thiol molecule 345 will have phosphonyl FR groups.

In process 300-6, allyl alcohol 305-1 is reacted with thioacetic acid in a thiol-ene reaction. In the first step of the reaction, oxygen (O$_2$) is added to a dichloromethane (DCM) solution of the allyl alcohol 305-1 and thioacetic acid. The mixture is refluxed, resulting in an acetate-protected mercaptopropanol 355. The second step in the reaction is a substitution reaction involving diphenyl chlorophosphate (DPCPa) and catalytic dimethylaminopyridine (DMAP) or diphenylphosphinic chloride (DPCPo). The acetate group is removed by refluxing the mixture in an ethanol (EtOH) solution containing sodium hydroxide (NaOH). This step results in the production of the hydroxy-derived flame retardant thiol molecule 360. If the process is carried out with DPCPa, the hydroxy-derived flame retardant thiol molecule 360 will have phosphoryl FR groups, and, if the reaction is carried out with DPCPo, the hydroxy-derived flame retardant thiol molecule 360 will have phosphonyl FR groups.

Figure 3D:
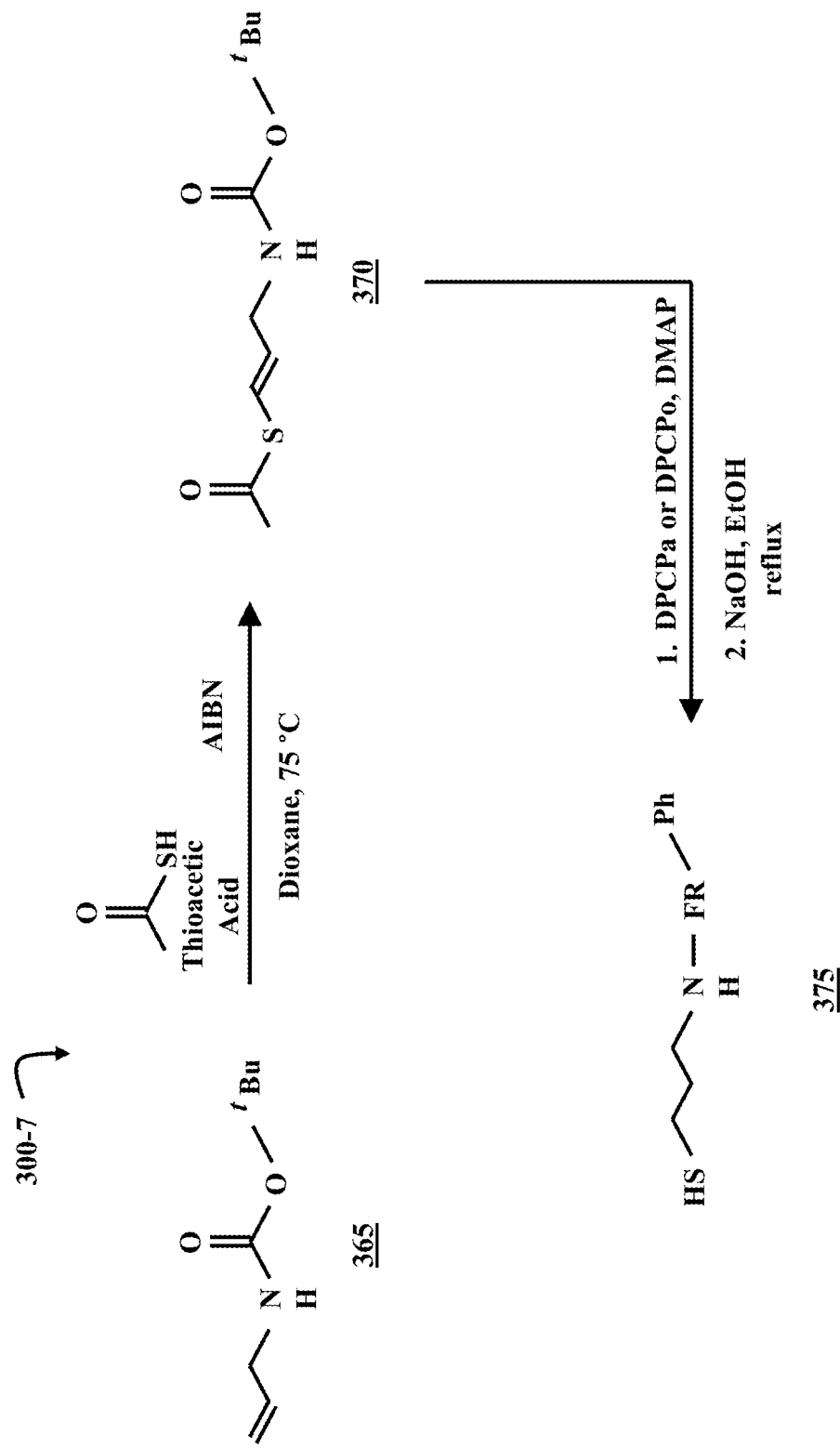
FIG. 3D is a chemical reaction diagram illustrating a process of synthesizing an amino-derived flame retardant thiol molecule, in accordance with embodiments of the present disclosure.

FIG. 3D is a chemical reaction diagram illustrating a process 300-7 of synthesizing an amino-derived flame retardant thiol molecule 375, in accordance with embodiments of the present disclosure. In process 300-7, 1-(boc-amino)-3-butene 365 is first reacted with thioacetic acid in a thiol-ene reaction. Azobisisobutyronitrile (AIBN) is added to the dioxane solution of 1-(boc-amino)-3-butene 365 and thioacetic acid, and the mixture is stirred at 75° C., resulting in an acetate-protected precursor 370 to the amino-derived flame retardant thiol molecule 375. The second step in process 300-7 is a substitution reaction with diphenyl chlorophosphate (DPCPa) or diphenylphosphinic chloride (DPCPo) and catalytic dimethylaminopyridine (DMAP). The acetate group and boc groups are removed under basic conditions (e.g., by refluxing the mixture in an ethanol (EtOH) solution containing sodium hydroxide (NaOH)). This step results in the production of the amino-derived flame retardant thiol molecule 375. If the process is carried out with DPCPa, the amino-derived flame retardant thiol molecule 375 will have phosphoryl FR groups, and, if the reaction is carried out with DPCPo, the amino-derived flame retardant thiol molecule 375 will have phosphonyl FR groups.

Figure 4:
FIG. 4 is a diagrammatic representation of the molecular structures of three thiol molecules that are involved in the synthesis of some examples of the flame retardant lysine-derived, proline-derived, reduced lysine-derived, or reduced proline-derived molecules, in accordance with embodiments of the present disclosure.
Figure 4:
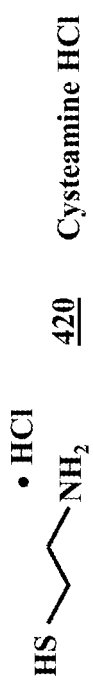
Figure 4:
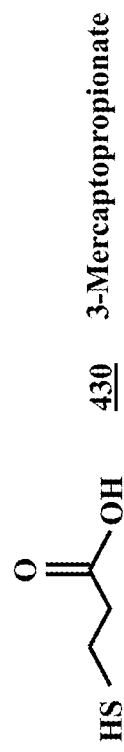

FIG. 4 is a diagrammatic representation of the molecular structures of three thiol molecules that are involved in the synthesis of some examples of the flame retardant lysine-derived, proline-derived, reduced lysine-derived, or reduced proline-derived molecules, in accordance with embodiments of the present disclosure. The three thiol molecules are 2-mercaptoethanol 410, cysteamine hydrochloride (HCl) 420, and 3-mercaptopropionate 430. Each of these thiols is involved in the synthesis of a thioether-linked flame retardant derivative. In these syntheses, the thiol molecules provide thioether R groups. Details of the syntheses and structures of the thioether-linked flame retardant lysine, proline, reduced lysine, or reduced proline-derived molecules are discussed in greater detail with regard to FIGS. 8A-8D.

Figure 5:
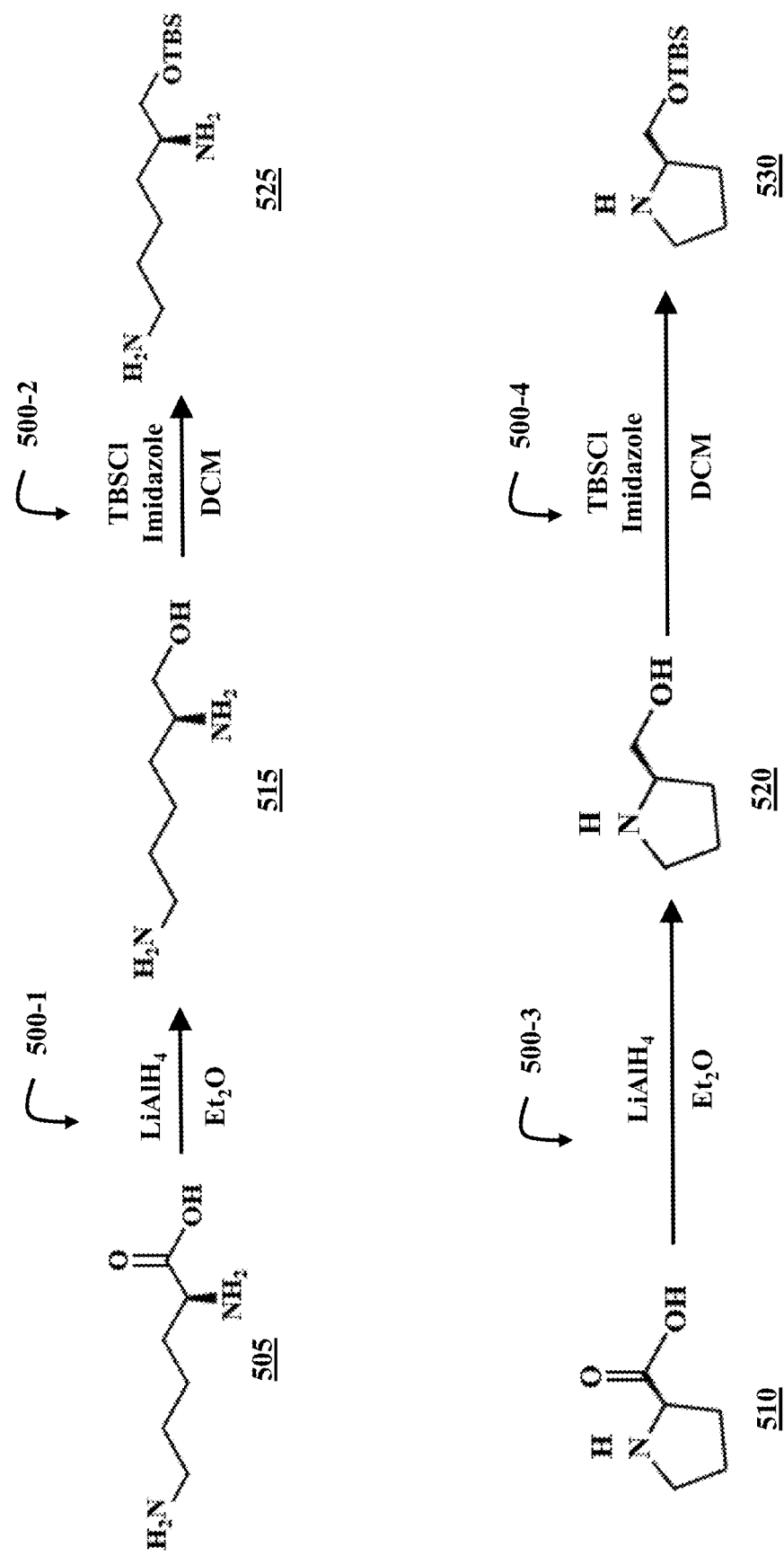
FIG. 5 is a chemical reaction diagram illustrating processes for forming reduced lysine, reduced proline, protected reduced lysine, and protected reduced proline molecules from lysine and proline, in accordance with embodiments of the present disclosure.

FIG. 5 is a chemical reaction diagram illustrating processes for forming reduced lysine 515, reduced proline 520, protected reduced lysine 525, and protected reduced proline 530 molecules from lysine 505 and proline 510, in accordance with embodiments of the present disclosure. In process 500-1, lysine 505 is reduced using lithium aluminum hydride (LiAlH$_4$) in a diethyl ether solution (Et$_2$O) to yield 2,6-diaminohexan-1-ol 515 (herein referred to as "reduced lysine 515"). The reduced lysine 515 molecule obtained in process 500-1 is then reacted with tert-butyldimethylsilyl chloride (TBSCl) and imidazole in a dichloromethane (DCM) solution in process 500-2 to yield (S)-6-((tert-butyldimethylsilyl)oxy)hexane-1,5-diamine 525 (herein referred to as "protected reduced lysine 525"). In process 500-3, proline 510 is reduced using lithium aluminum hydride in a diethyl ether solution (Et$_2$O) to yield pyrrolidin-2-ylmethanol 520 (herein referred to as "reduced proline 520"). In process 500-4, the reduced proline 520 is then reacted with tert-butyldimethylsilyl chloride (TBSCl) and imidazole in a dichloromethane (DCM) solution to yield (R)-2-(((tert-butyldimethylsilyl)oxy)methyl)pyrrolidine 530 (herein referred to as "protected reduced proline 530"). The lysine 505, reduced lysine 515, protected reduced lysine 525, proline 510, reduced proline 520, and protected reduced proline 530 molecules depicted in FIG. 5 can then be used as a precursor for forming various flame retardant molecules, shown and discussed in greater detail with respect to FIGS. 6-13.

Figure 6A:
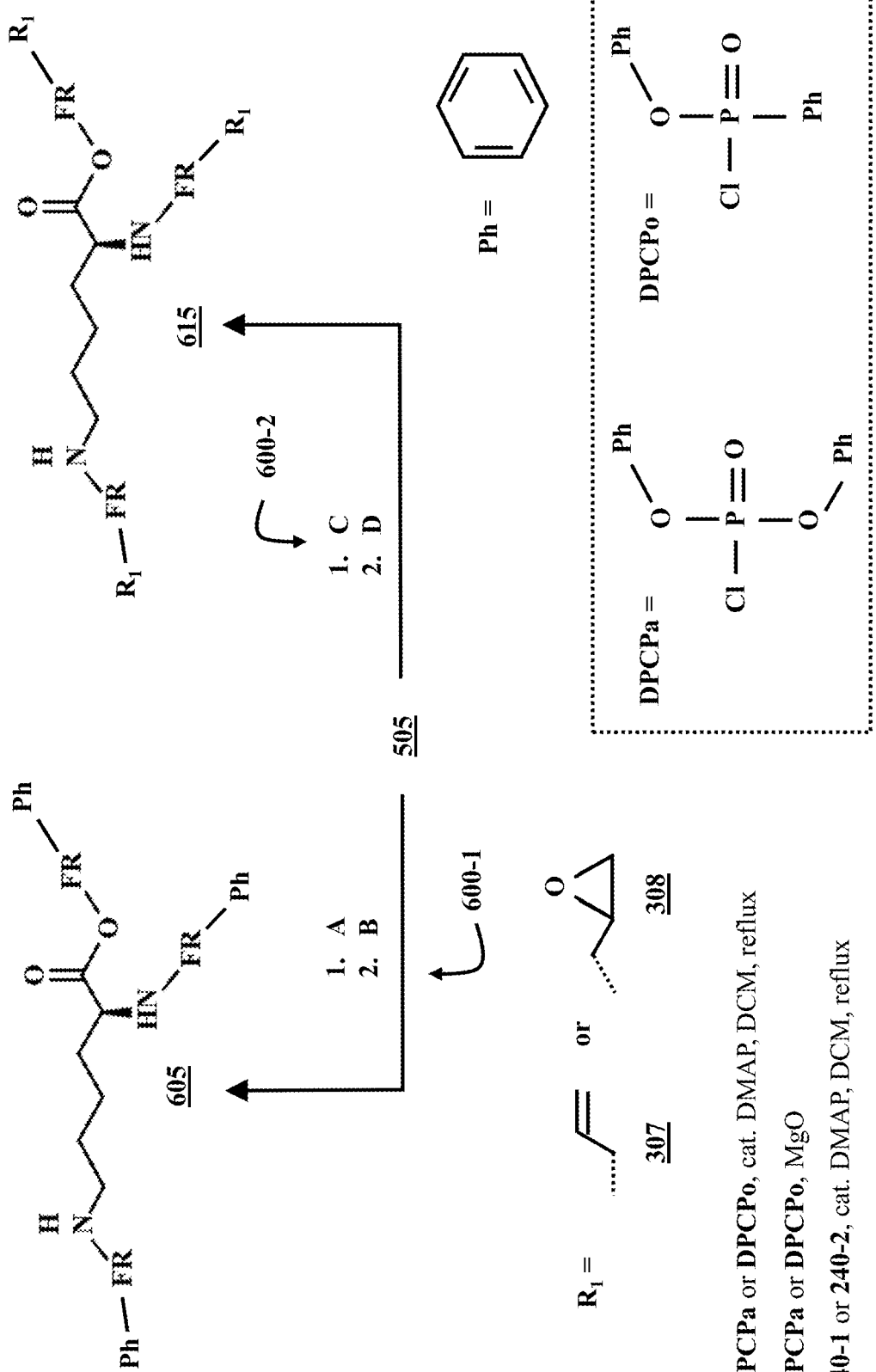
FIG. 6A is a chemical reaction diagram illustrating a process of synthesizing a flame retardant lysine-derived small molecule and a process of forming a trifunctionalized flame retardant lysine-derived cross-linker, in accordance with embodiments of the present disclosure.

FIG. 6A is a chemical reaction diagram illustrating a process 600-1 of synthesizing a flame retardant lysine-derived small molecule 605 and a process 600-2 of forming a trifunctionalized flame retardant lysine cross-linker 615, in accordance with embodiments of the present disclosure. In process 600-1, lysine 505 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. The resulting mixture is reacted with either diphenyl chlorophosphate (DPCPa) or diphenylphosphinic chloride (DPCPo) and magnesium oxide (MgO), producing the flame retardant lysine-derived small molecule 605. If the process is carried out with DPCPa, the flame retardant lysine-derived small molecule 605 will have phosphoryl FR groups, and, if the reaction is carried out with DPCPo, the flame retardant lysine-derived small molecule 605 will have phosphonyl FR groups.

In process 600-2, lysine 505 is reacted with a phosphorus-based flame retardant molecule 240 and catalytic dimethylaminopyridine (cat. DMAP) in a dichloromethane (DCM) solution, and the resulting mixture is reacted with a phosphorus-based flame retardant molecule 240 and magnesium oxide (MgO), to yield the allyl functionalized or the epoxy functionalized flame retardant lysine cross-linker 615. If lysine 505 is reacted with a phosphorus-based flame retardant molecule 240 having an allyl R$_1$ group 307, the functionalized flame retardant will be an allyl functionalized flame retardant lysine cross-linker (e.g., R$_1$ as shown on FIG. 6A will be an allyl functional group 307, see FIG. 6B). If lysine 505 is reacted with a phosphorus-based flame retardant molecule 240 having an epoxy R$_1$ group 308, the functionalized flame retardant will be an epoxy functionalized flame retardant lysine cross-linker (e.g., R$_1$ as shown on FIG. 6A will be an epoxy functional group 308, see FIG. 6B). If the reaction is carried out with phosphate-based flame retardant molecule 240-1, the trifunctionalized flame retardant lysine cross-linker 615 will have a phosphoryl FR group, and, if the reaction is carried out with the phosphonate-based flame retardant molecule 240-2, the trifunctionalized flame retardant lysine cross-linker 615 will have a phosphonyl FR group.

Figure 6B:
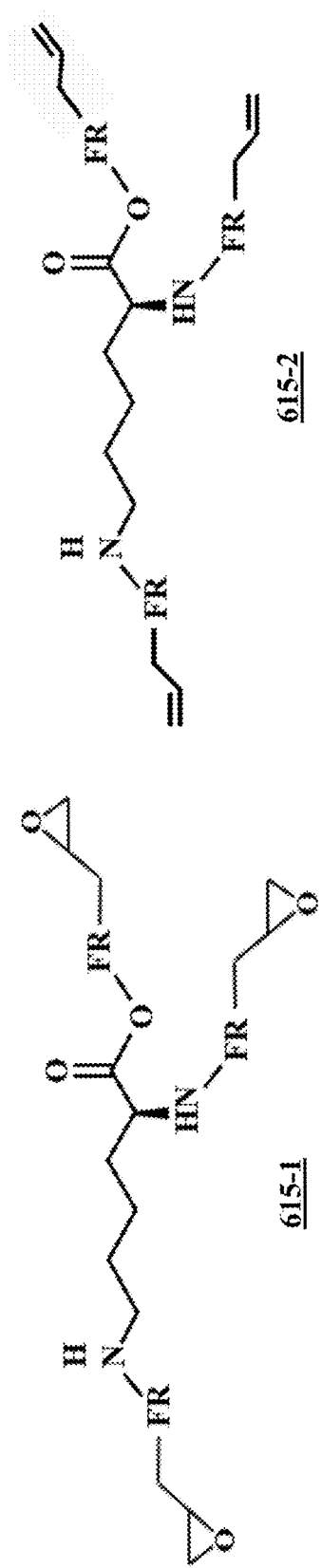
FIG. 6B is a chemical diagram illustrating an allyl functionalized flame retardant lysine-derived cross-linker and an epoxy functionalized flame retardant lysine-derived cross-linker, in accordance with embodiments of the present disclosure.

FIG. 6B illustrates an epoxy functionalized flame retardant lysine cross-linker 615-1 and an allyl functionalized flame retardant lysine cross-linker 615-2, in accordance with embodiments of the present disclosure. As mentioned with regard to FIG. 6A, if lysine 505 is reacted with a phosphorus-based flame retardant molecule 240 having an epoxy R$_1$ group 308, the functionalized flame retardant will be the epoxy functionalized flame retardant lysine cross-linker 615-1. If lysine 505 is reacted with a phosphorus-based flame retardant molecule 240 having an allyl R$_1$ group 307, the functionalized flame retardant will be the allyl functionalized flame retardant lysine cross-linker 615-2.

Figure 6C:
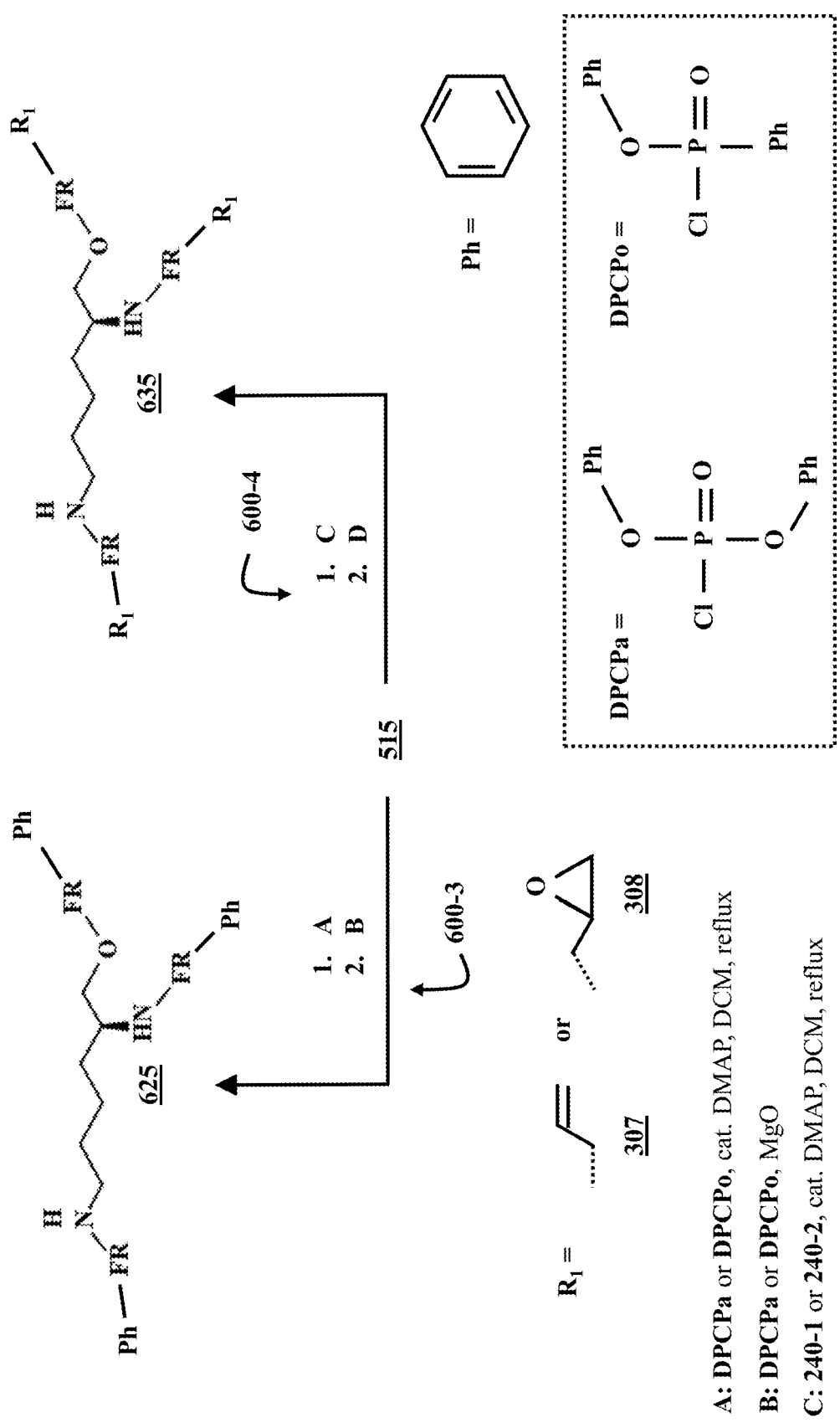
FIG. 6C is a chemical reaction diagram illustrating a process of synthesizing a flame retardant reduced lysine-derived small molecule and a process of forming a trifunctionalized flame retardant reduced lysine-derived cross-linker, in accordance with embodiments of the present disclosure.

FIG. 6C is a chemical reaction diagram illustrating a process 600-3 of synthesizing a flame retardant reduced lysine-derived small molecule 625 and a process 600-4 of forming a trifunctionalized flame retardant reduced lysine cross-linker 635, in accordance with embodiments of the present disclosure. In process 600-3, reduced lysine 515 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. The resulting mixture is reacted with either diphenyl chlorophosphate (DPCPa) or diphenylphosphinic chloride (DPCPo) and magnesium oxide (MgO), producing the flame retardant reduced lysine-derived small molecule 625. If the process is carried out with DPCPa, the flame retardant reduced lysine-derived small molecule 625 will have phosphoryl FR groups, and, if the reaction is carried out with DPCPo, the flame retardant reduced lysine-derived small molecule 625 will have phosphonyl FR groups.

In process 600-4, reduced lysine 515 is reacted with a phosphorus-based flame retardant molecule 240 and catalytic dimethylaminopyridine (DMAP) in a dichloromethane (DCM) solution, and the resulting mixture is reacted with a phosphorus-based flame retardant molecule 240 and magnesium oxide (MgO), to yield the trifunctionalized flame retardant reduced lysine cross-linker 635. If reduced lysine 515 is reacted with a phosphorus-based flame retardant molecule 240 having an allyl $R_1$ group 307, the functionalized flame retardant will be an allyl functionalized flame retardant reduced lysine cross-linker (e.g., $R_1$ as shown on FIG. 6C will be an allyl functional group 307, see FIG. 6D). If reduced lysine 515 is reacted with a phosphorus-based flame retardant molecule 240 having an epoxy $R_1$ group 308, the functionalized flame retardant will be an epoxy functionalized flame retardant reduced lysine cross-linker (e.g., $R_1$ as shown on FIG. 6C will be an epoxy functional group 308, see FIG. 6D). If the reaction is carried out with phosphate-based flame retardant molecule 240-1, the trifunctionalized flame retardant reduced lysine cross-linker 635 will have a phosphoryl FR group, and, if the reaction is carried out with the phosphonate-based flame retardant molecule 240-2, the trifunctionalized flame retardant reduced lysine cross-linker 635 will have a phosphonyl FR group.

Figure 6D:
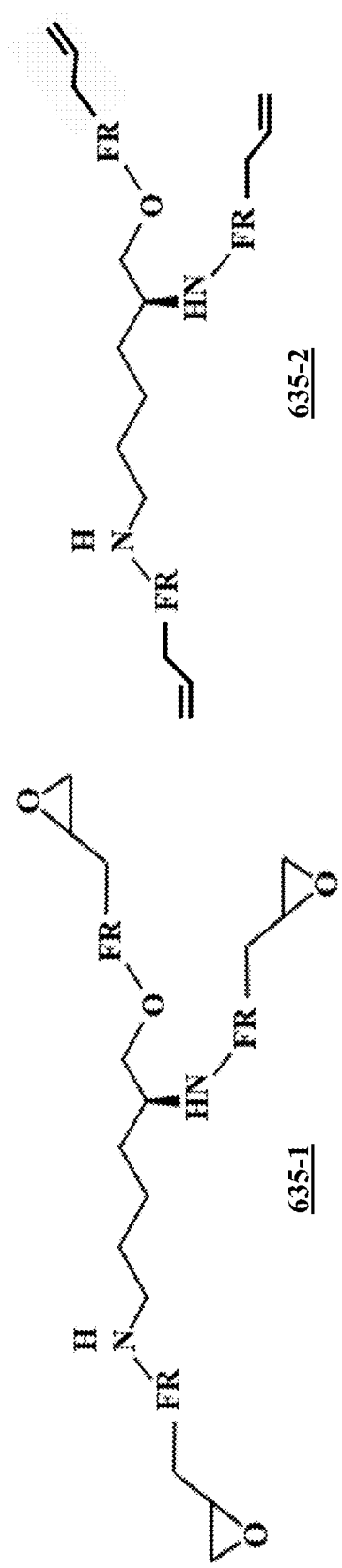
FIG. 6D is a chemical diagram illustrating an allyl functionalized flame retardant reduced lysine-derived cross-linker and an epoxy functionalized flame retardant reduced lysine-derived cross-linker, in accordance with embodiments of the present disclosure.

FIG. 6D illustrates an epoxy functionalized flame retardant reduced lysine cross-linker 635-1 and an allyl functionalized flame retardant reduced lysine cross-linker 635-2, in accordance with embodiments of the present disclosure. As mentioned with regard to FIG. 6C, if reduced lysine 515 is reacted with a phosphorus-based flame retardant molecule 240 having an epoxy $R_1$ group 308, the functionalized flame retardant will be the epoxy functionalized flame retardant reduced lysine cross-linker 635-1. If reduced lysine 515 is reacted with a phosphorus-based flame retardant molecule 240 having an allyl $R_1$ group 307, the functionalized flame retardant will be the allyl functionalized flame retardant reduced lysine cross-linker 635-2.

Figure 6E:
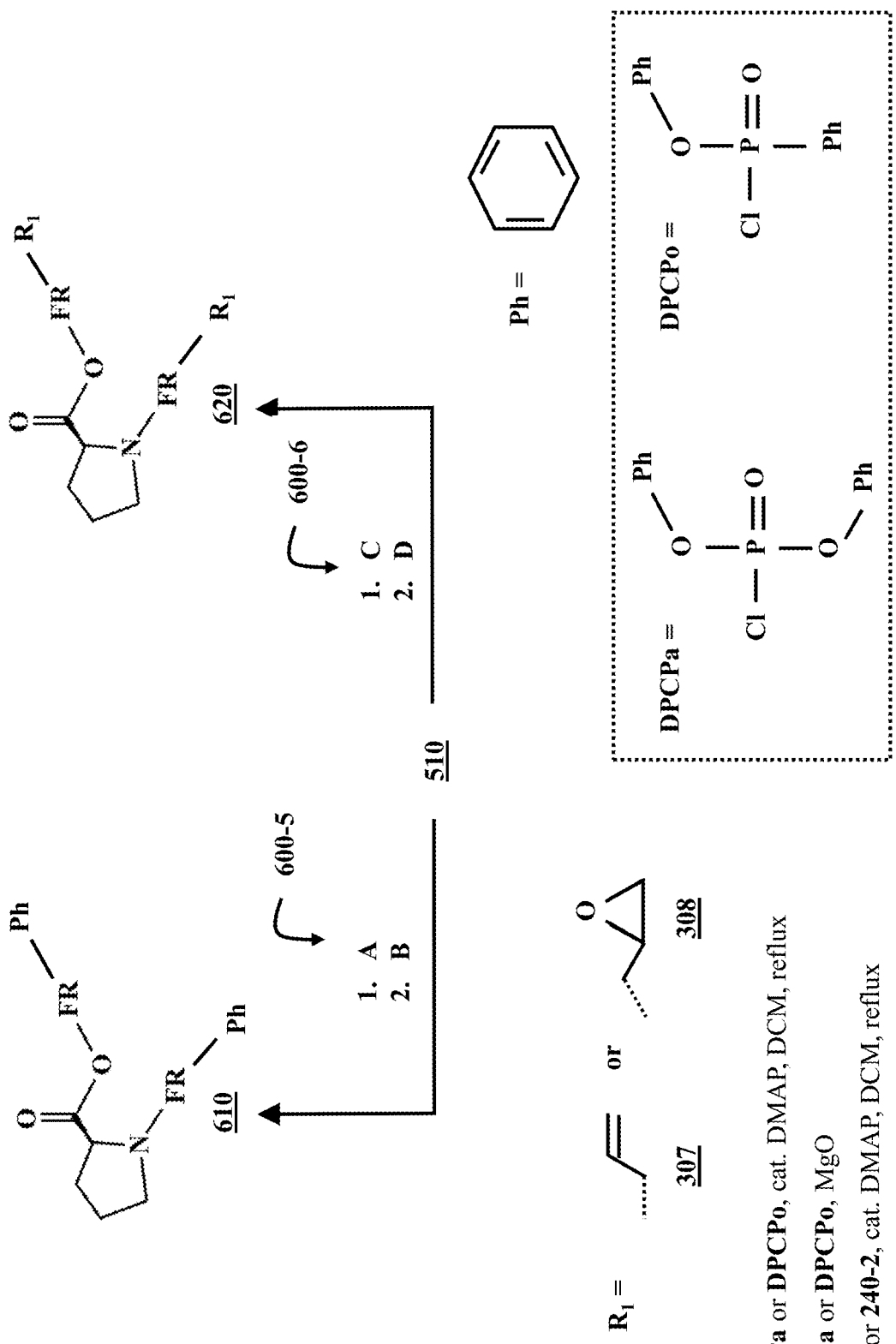
FIG. 6E is a chemical reaction diagram illustrating a process of synthesizing a flame retardant proline-derived small molecule and a process of forming a difunctionalized flame retardant proline-derived cross-linker, in accordance with embodiments of the present disclosure.

FIG. 6E is a chemical reaction diagram illustrating a process 600-5 of synthesizing a flame retardant proline-derived small molecule 610 and a process 600-6 of forming an allyl functionalized or an epoxy functionalized flame retardant proline cross-linker 620, in accordance with embodiments of the present disclosure. In process 600-5, proline 510 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. The resulting mixture is reacted with either diphenyl chlorophosphate (DPCPa) or diphenylphosphinic chloride (DPCPo) and magnesium oxide (MgO), producing the flame retardant proline-derived small molecule 610. If the process is carried out with DPCPa, the flame retardant proline-derived small molecule 610 will have phosphoryl FR groups, and, if the reaction is carried out with DPCPo, the flame retardant proline-derived small molecule 610 will have phosphonyl FR groups.

In process 600-6, proline 510 is reacted with a phosphorus-based flame retardant molecule 240 and catalytic dimethylaminopyridine (DMAP) in a dichloromethane (DCM) solution, and the resulting mixture is reacted with a phosphorus-based flame retardant molecule 240 and magnesium oxide (MgO), to yield the allyl functionalized or the epoxy functionalized flame retardant proline cross-linker 620. If proline 510 is reacted with a phosphorus-based flame retardant molecule 240 having an allyl $R_1$ group 307, the functionalized flame retardant will be an allyl functionalized flame retardant proline cross-linker (e.g., $R_1$ as shown on FIG. 6E will be an allyl functional group 307, see FIG. 6F). If proline 510 is reacted with a phosphorus-based flame retardant molecule 240 having an epoxy $R_1$ group 308, the functionalized flame retardant will be an epoxy functionalized flame retardant proline cross-linker (e.g., $R_1$ as shown on FIG. 6E will be an epoxy functional group 308, see FIG. 6F). If the reaction is carried out with phosphate-based flame retardant molecule 240-1, the difunctionalized flame retardant proline cross-linker 620 will have a phosphoryl FR group, and, if the reaction is carried out with the phosphonate-based flame retardant molecule 240-2, the difunctionalized flame retardant proline cross-linker 620 will have a phosphonyl FR group.

Figure 6F:
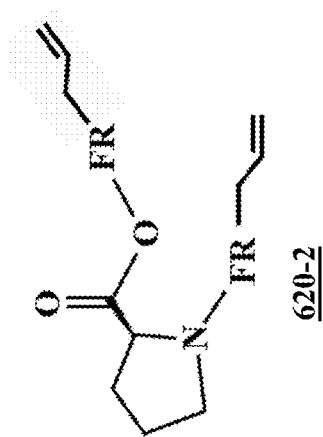
FIG. 6F is a chemical diagram illustrating an allyl functionalized flame retardant proline-derived cross-linker and an epoxy functionalized flame retardant proline-derived cross-linker, in accordance with embodiments of the present disclosure.
Figure 6F:
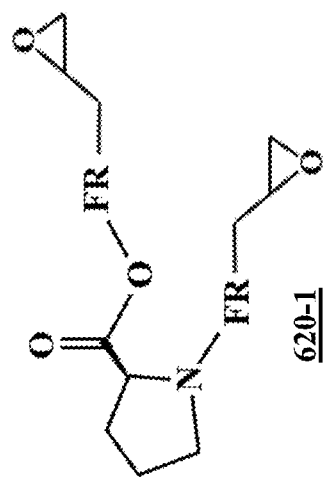

FIG. 6F is a chemical diagram illustrating an epoxy functionalized flame retardant proline cross-linker 620-1 and an allyl functionalized flame retardant proline cross-linker 620-2, in accordance with embodiments of the present disclosure. As mentioned with regard to FIG. 6E, if proline 510 is reacted with a phosphorus-based flame retardant molecule 240 having an epoxy $R_1$ group 308, the functionalized flame retardant will be the epoxy functionalized flame retardant proline cross-linker 620-1. If proline 510 is reacted with a phosphorus-based flame retardant molecule 240 having an allyl $R_1$ group 307, the functionalized flame retardant will be the allyl functionalized flame retardant proline cross-linker 620-2.

Figure 6G:
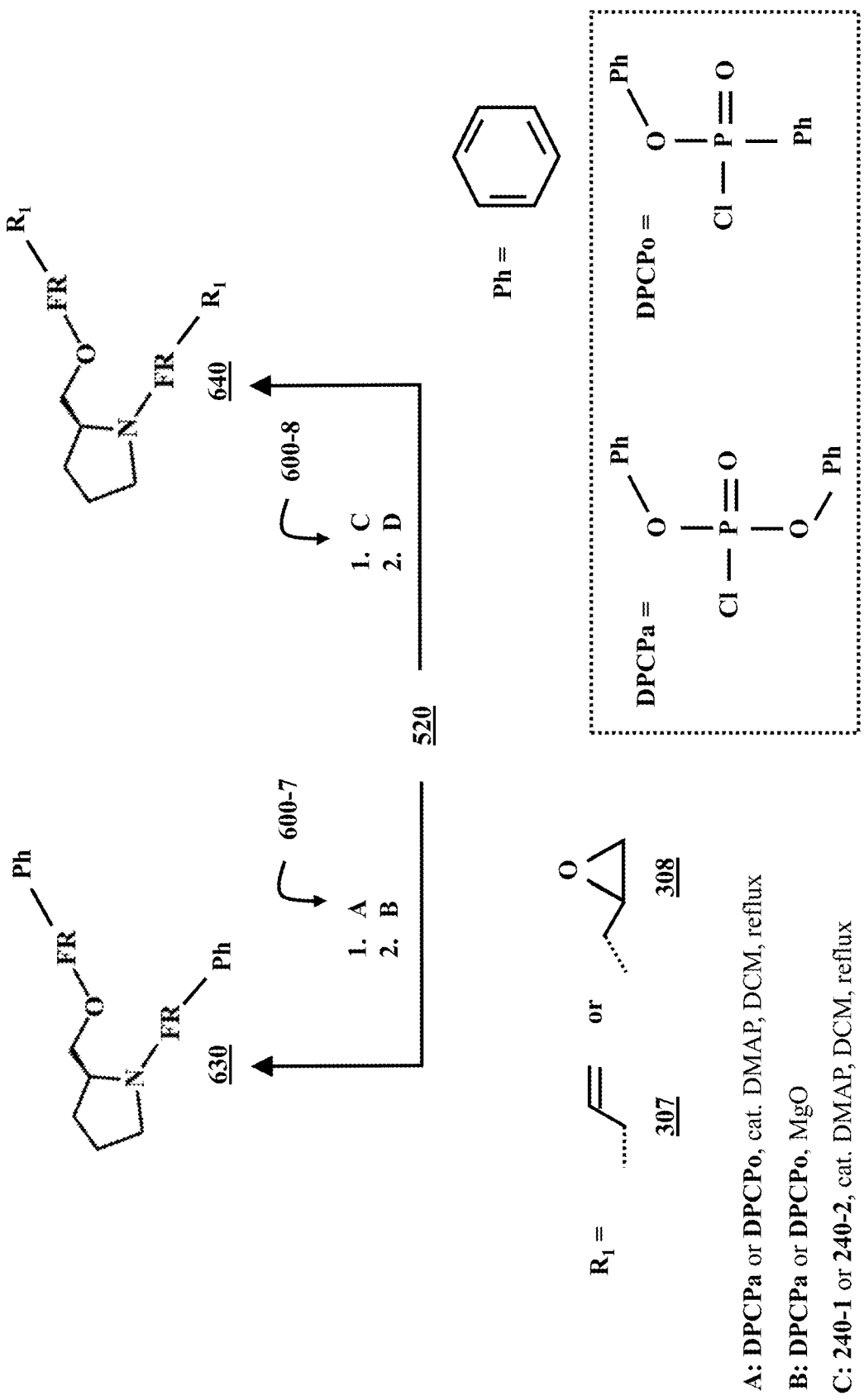
FIG. 6G is a chemical reaction diagram illustrating a process of synthesizing a flame retardant reduced proline-derived small molecule and a process of forming a trifunctionalized flame retardant reduced proline-derived cross-linker, in accordance with embodiments of the present disclosure.

FIG. 6G is a chemical reaction diagram illustrating a process 600-7 of synthesizing a flame retardant reduced proline-derived small molecule 630 and a process 600-8 of forming an allyl functionalized or an epoxy functionalized flame retardant reduced proline cross-linker 640, in accordance with embodiments of the present disclosure. In process 600-7, reduced proline 520 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. The resulting mixture is reacted with either diphenyl chlorophosphate (DPCPa) or diphenylphosphinic chloride (DPCPo) and magnesium oxide (MgO), producing the flame retardant reduced proline-derived small molecule 630. If the process is carried out with DPCPa, the flame retardant reduced proline-derived small molecule 630 will have phosphoryl FR groups, and, if the reaction is carried out with DPCPo, the flame retardant reduced proline-derived small molecule 630 will have phosphonyl FR groups.

In process 600-8, reduced proline 520 is reacted with a phosphorus-based flame retardant molecule 240 and catalytic dimethylaminopyridine (DMAP) in a dichloromethane (DCM) solution, and the resulting mixture is reacted with a phosphorus-based flame retardant molecule 240 and magnesium oxide (MgO), to yield the allyl functionalized or the epoxy functionalized flame retardant reduced proline cross-linker 640. If reduced proline 520 is reacted with a phosphorus-based flame retardant molecule 240 having an allyl $R_1$ group 307, the functionalized flame retardant will be an allyl functionalized flame retardant reduced proline cross-linker (e.g., $R_1$ as shown on FIG. 6G will be an allyl functional group 307, see FIG. 6H). If reduced proline 520 is reacted with a phosphorus-based flame retardant molecule 240 having an epoxy $R_1$ group 308, the functionalized flame retardant will be an epoxy functionalized flame retardant reduced proline cross-linker (e.g., $R_1$ as shown on FIG. 6G will be an epoxy functional group 308, see FIG. 6H). If the reaction is carried out with phosphate-based flame retardant molecule 240-1, the difunctionalized flame retardant reduced proline cross-linker 640 will have a phosphoryl FR group, and, if the reaction is carried out with the phosphonate-based flame retardant molecule 240-2, the difunctionalized flame retardant reduced proline cross-linker 640 will have a phosphonyl FR group.

Figure 6H:
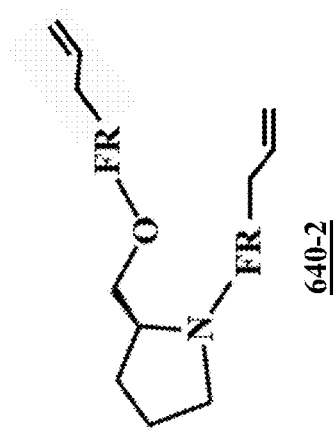
FIG. 6H is a chemical diagram illustrating an allyl functionalized flame retardant reduced proline-derived cross-linker and an epoxy functionalized flame retardant reduced proline-derived cross-linker, in accordance with embodiments of the present disclosure.
Figure 6H:
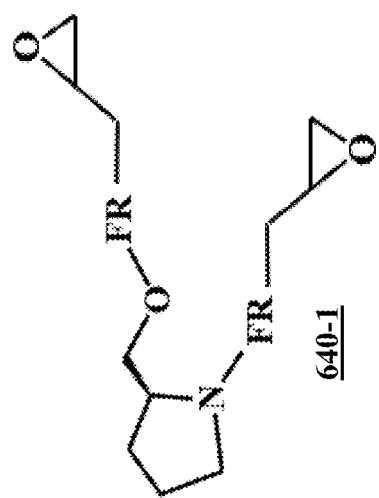

FIG. 6H illustrates an epoxy functionalized flame retardant reduced proline cross-linker 640-1 and an allyl functionalized flame retardant reduced proline cross-linker 640-2, in accordance with embodiments of the present disclosure. As mentioned with regard to FIG. 6G, if reduced proline 520 is reacted with a phosphorus-based flame retardant molecule 240 having an epoxy $R_1$ group 308, the functionalized flame retardant will be the epoxy functionalized flame retardant reduced proline cross-linker 640-1. If reduced proline 520 is reacted with a phosphorus-based flame retardant molecule 240 having an allyl $R_1$ group 307, the functionalized flame retardant will be the allyl functionalized flame retardant reduced proline cross-linker 640-2.

Figure 7A:
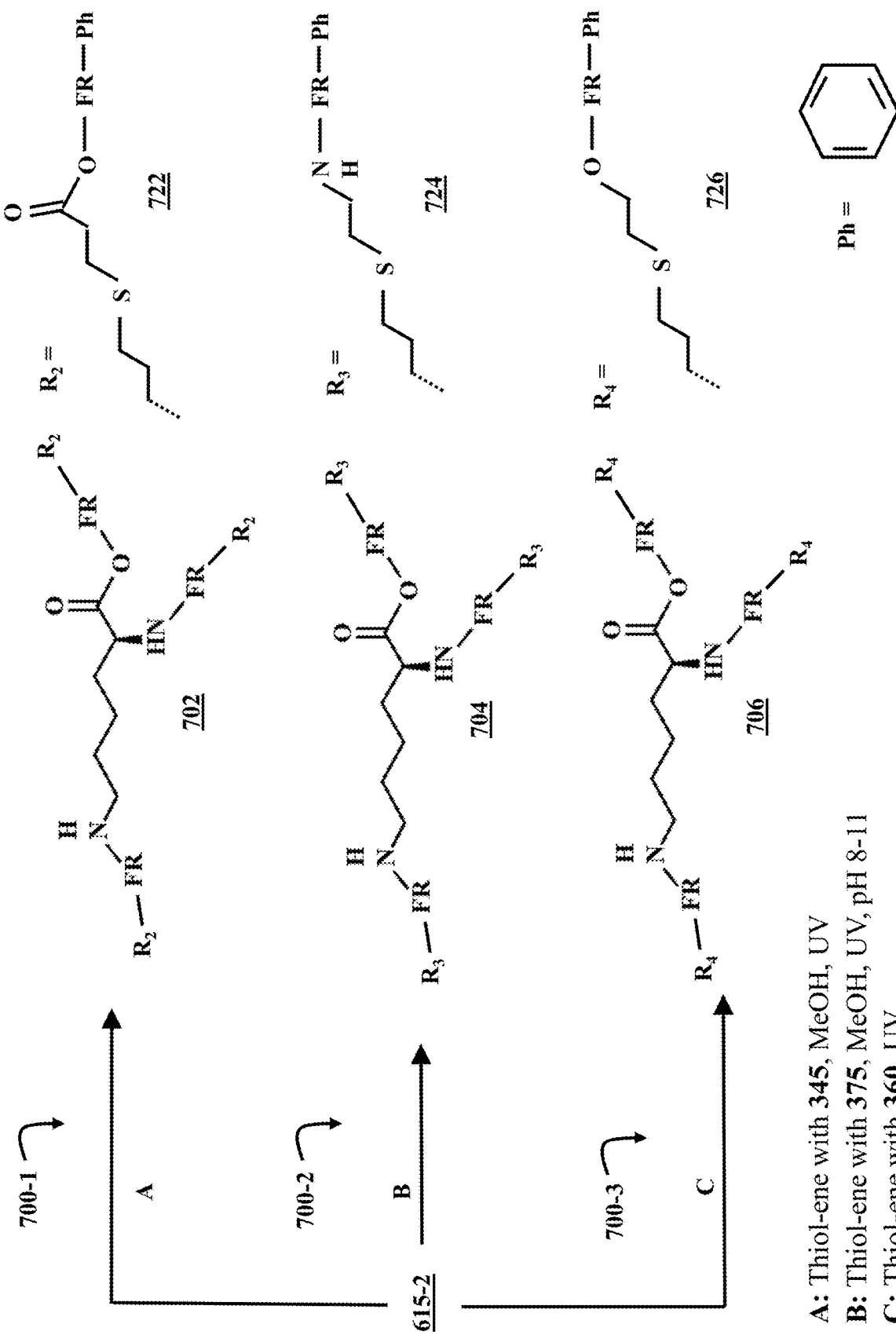
FIG. 7A is a chemical reaction diagram illustrating three processes of synthesizing thioether-linked flame retardant lysine-derived small molecules, in accordance with embodiments of the present disclosure.

FIG. 7A is a chemical reaction diagram illustrating three processes 700-1, 700-2, and 700-3 of synthesizing thioether-linked flame retardant lysine-derived small molecules, in accordance with embodiments of the present disclosure. Each process is a thiol-ene reaction between the allyl-substituted flame retardant lysine cross-linker 615-2 and a flame retardant thiol molecule 345, 360, or 375. The syntheses and structures of the flame retardant thiol molecules are discussed in greater detail with regard to FIGS. 3C and 3D.

In process 700-1, the allyl functionalized flame retardant lysine cross-linker 615-2 is reacted with the carboxylic acid-derived flame retardant thiol molecule 345 under UV light (e.g., light with a wavelength of approximately 100-400 nm) in a methanol (MeOH) solution. The resulting thioether-linked flame retardant lysine-derived small molecule 702 has a thioether $R_2$ group 722 that corresponds to the carboxylic acid-derived flame retardant thiol molecule 345. In process 700-2, the allyl functionalized flame retardant lysine cross-linker 615-2 is reacted with the amino-derived flame retardant thiol molecule 375 in a methanol (MeOH) solution with a pH of approximately 8-11 under UV light. The resulting thioether-linked flame retardant lysine-derived small molecule 704 has a thioether $R_3$ group 724 that corresponds to the amino-derived flame retardant thiol molecule 375. In process 700-3, the allyl functionalized flame retardant lysine cross-linker 615-2 is reacted with the hydroxy-derived flame retardant thiol molecule 360 under UV light. The resulting thioether-linked flame retardant lysine-derived small molecule 706 has a thioether $R_4$ group 726 that corresponds to the hydroxy-derived flame retardant thiol molecule 360.

Figure 7B:
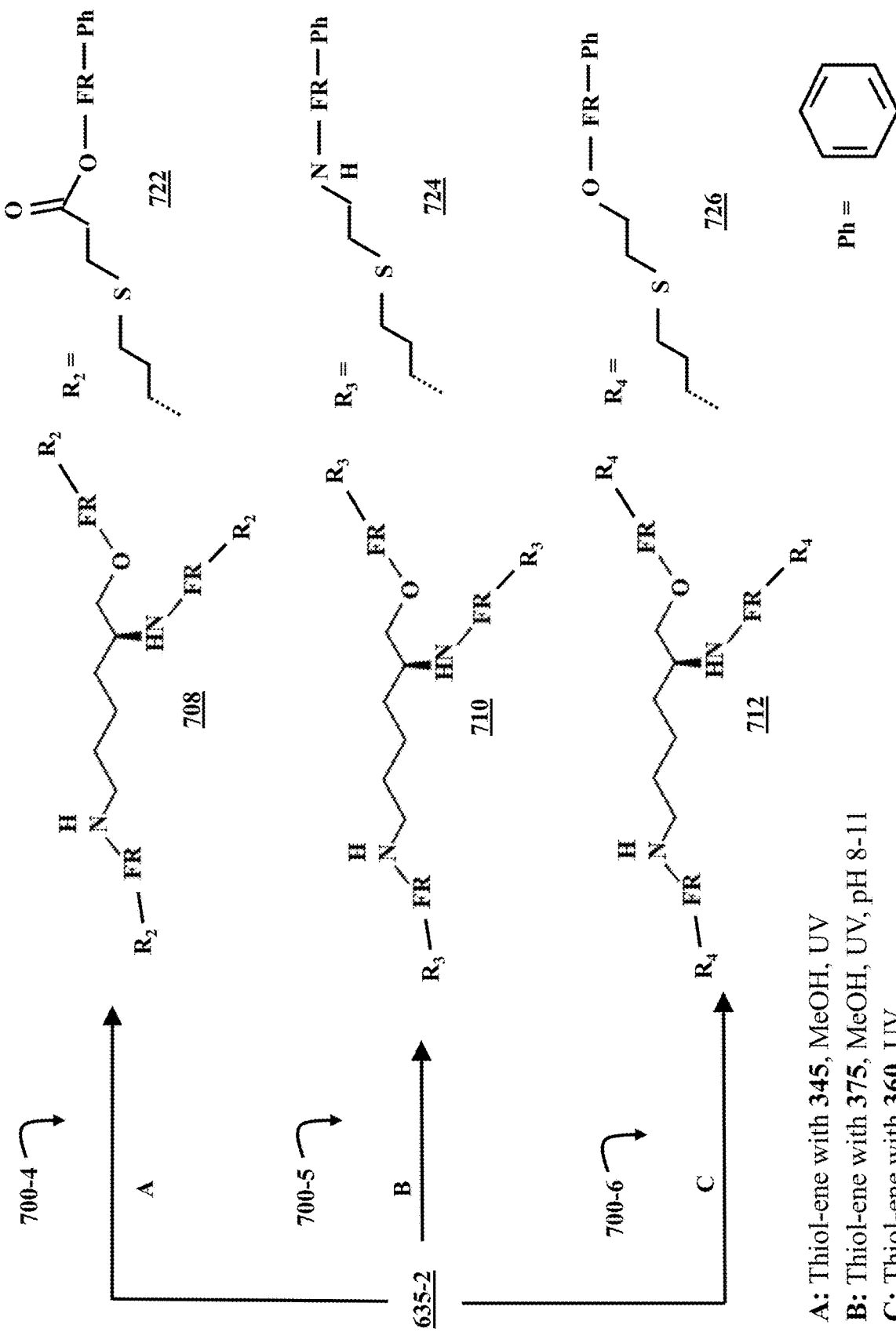
FIG. 7B is a chemical reaction diagram illustrating three processes of synthesizing thioether-linked flame retardant reduced lysine-derived small molecules, in accordance with embodiments of the present disclosure.

FIG. 7B is a chemical reaction diagram illustrating three processes 700-4, 700-5, and 700-6 of synthesizing thioether-linked flame retardant reduced lysine-derived small molecules, in accordance with embodiments of the present disclosure. Each process is a thiol-ene reaction between the allyl-substituted flame retardant reduced lysine cross-linker 635-2 and a flame retardant thiol molecule 345, 360, or 375. The syntheses and structures of the flame retardant thiol molecules are discussed in greater detail with regard to FIGS. 3C and 3D.

In process 700-4, the allyl functionalized flame retardant reduced lysine cross-linker 635-2 is reacted with the carboxylic acid-derived flame retardant thiol molecule 345 under UV light in a methanol (MeOH) solution. The resulting thioether-linked flame retardant reduced lysine-derived small molecule 708 has a thioether $R_2$ group 722 that corresponds to the carboxylic acid-derived flame retardant thiol molecule 345. In process 700-5, the allyl functionalized flame retardant reduced lysine cross-linker 635-2 is reacted with the amino-derived flame retardant thiol molecule 375 in a methanol (MeOH) solution with a pH of approximately 8-11 under UV light. The resulting thioether-linked flame retardant reduced lysine-derived small molecule 710 has a thioether $R_3$ group 724 that corresponds to the amino-derived flame retardant thiol molecule 375. In process 700-6, the allyl functionalized flame retardant reduced lysine cross-linker 635-2 is reacted with the hydroxy-derived flame retardant thiol molecule 360 under UV light. The resulting thioether-linked flame retardant reduced lysine-derived small molecule 706 has a thioether $R_4$ group 726 that corresponds to the hydroxy-derived flame retardant thiol molecule 360.

Figure 7C:
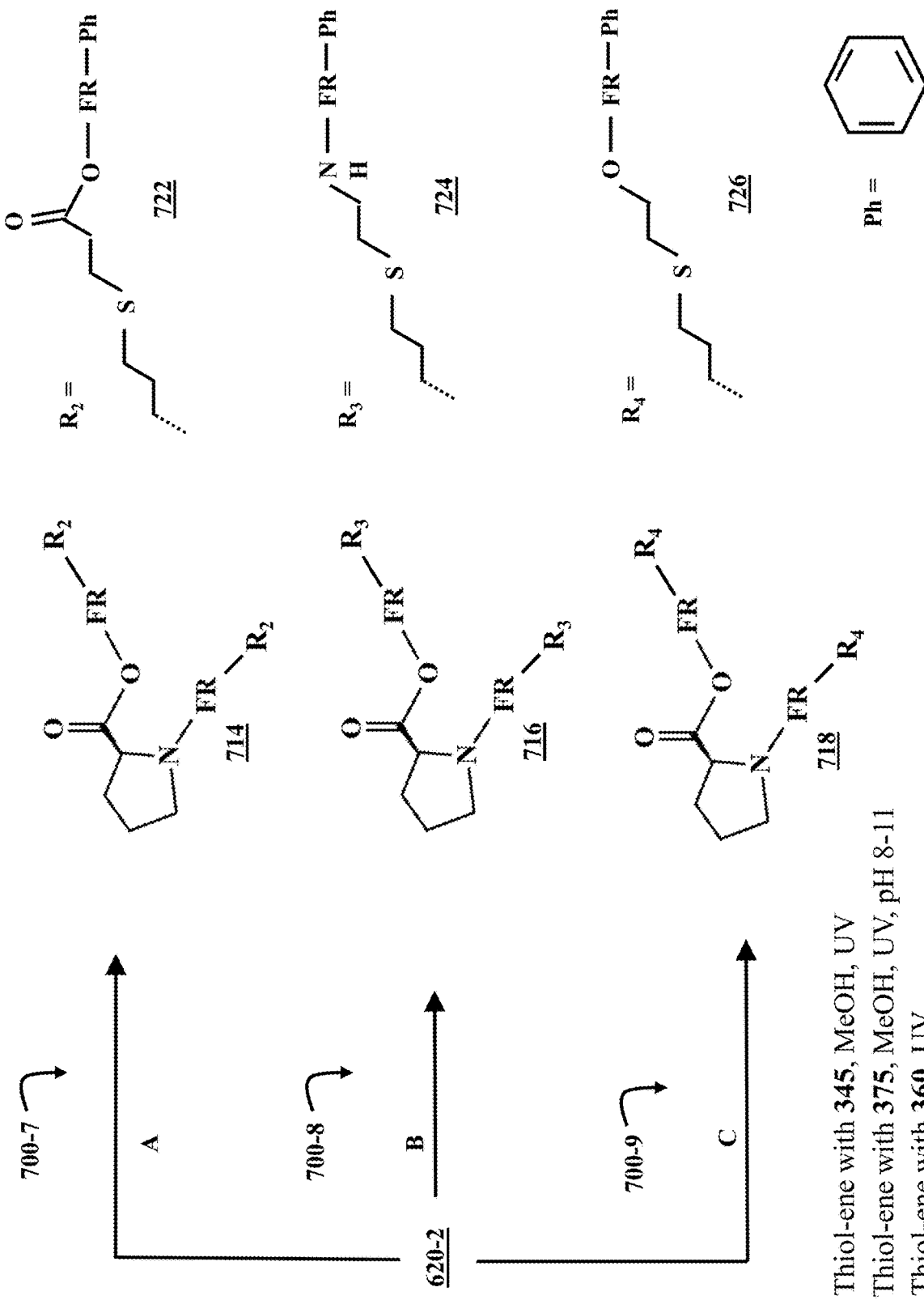
FIG. 7C is a chemical reaction diagram illustrating three processes of synthesizing thioether-linked flame retardant proline-derived small molecules, in accordance with embodiments of the present disclosure.

FIG. 7C is a chemical reaction diagram illustrating three processes 700-7, 700-8, and 700-9 of synthesizing thioether-linked flame retardant proline-derived small molecules, in accordance with embodiments of the present disclosure. Each process is a thiol-ene reaction between the allyl-substituted flame retardant proline cross-linker 620-2 and a flame retardant thiol molecule 345, 360, or 375. The syntheses and structures of the flame retardant thiol molecules are discussed in greater detail with regard to FIGS. 3C and 3D.

In process 700-7, the allyl functionalized flame retardant proline cross-linker 620-2 is reacted with the carboxylic acid-derived flame retardant thiol molecule 345 under UV light (e.g., light with a wavelength of approximately 100-400 nm) in a methanol (MeOH) solution. The resulting thioether-linked flame retardant proline-derived small molecule 714 has a thioether $R_2$ group 722 that corresponds to the carboxylic acid-derived flame retardant thiol molecule 345. In process 700-8, the allyl functionalized flame retardant proline cross-linker 620-2 is reacted with the amino-derived flame retardant thiol molecule 375 in a methanol (MeOH) solution with a pH of approximately 8-11 under UV light. The resulting thioether-linked flame retardant proline-derived small molecule 716 has a thioether $R_3$ group 724 that corresponds to the amino-derived flame retardant thiol molecule 375. In process 700-9, the allyl functionalized flame retardant proline cross-linker 620-2 is reacted with the hydroxy-derived flame retardant thiol molecule 360 under UV light. The resulting thioether-linked flame retardant proline-derived small molecule 718 has a thioether $R_4$ group 726 that corresponds to the hydroxy-derived flame retardant thiol molecule 360.

Figure 7D:
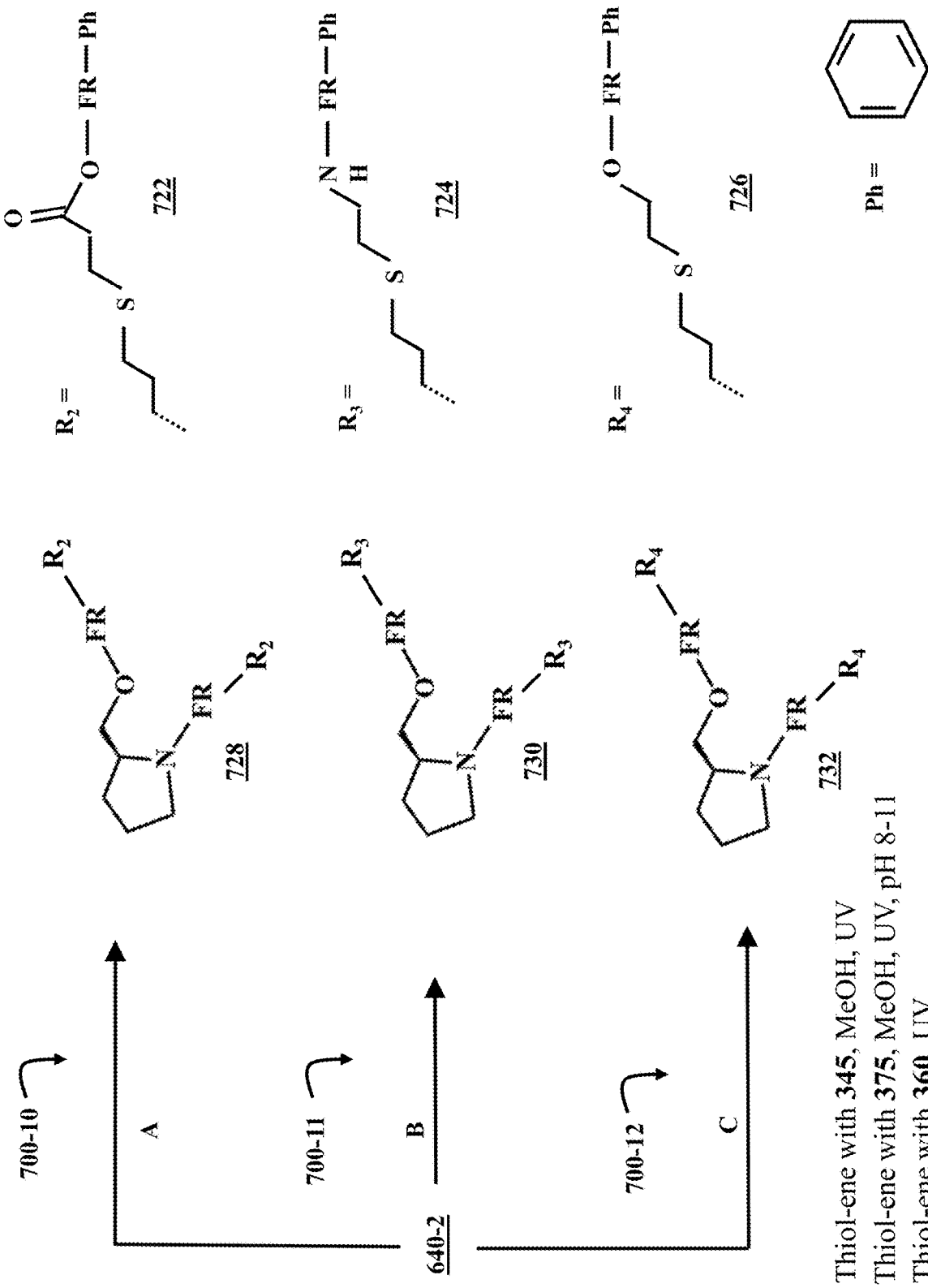
FIG. 7D is a chemical reaction diagram illustrating three processes of synthesizing thioether-linked flame retardant reduced proline-derived small molecules, in accordance with embodiments of the present disclosure

FIG. 7D is a chemical reaction diagram illustrating three processes 700-10, 700-11, and 700-12 of synthesizing thioether-linked flame retardant reduced proline-derived small molecules, in accordance with embodiments of the present disclosure. Each process is a thiol-ene reaction between the allyl-substituted flame retardant reduced cross-linker 640-2 and a flame retardant thiol molecule 345, 360, or 375. The syntheses and structures of the flame retardant thiol molecules are discussed in greater detail with regard to FIGS. 3C and 3D.

In process 700-10, the allyl functionalized flame retardant reduced proline cross-linker 640-2 is reacted with the carboxylic acid-derived flame retardant thiol molecule 345 under UV light in a methanol (MeOH) solution. The resulting thioether-linked flame retardant reduced proline-derived small molecule 728 has a thioether $R_2$ group 722 that corresponds to the carboxylic acid-derived flame retardant thiol molecule 345. In process 700-11, the allyl functionalized flame retardant reduced proline cross-linker 640-2 is reacted with the amino-derived flame retardant thiol molecule 375 in a methanol (MeOH) solution with a pH of approximately 8-11 under UV light. The resulting thioether-linked flame retardant reduced proline-derived small molecule 730 has a thioether $R_3$ group 724 that corresponds to the amino-derived flame retardant thiol molecule 375. In process 700-12, the allyl functionalized flame retardant reduced proline cross-linker 640-2 is reacted with the hydroxy-derived flame retardant thiol molecule 360 under UV light. The resulting thioether-linked flame retardant reduced proline-derived small molecule 732 has a thioether $R_4$ group 726 that corresponds to the hydroxy-derived flame retardant thiol molecule 360.

Figure 8A:
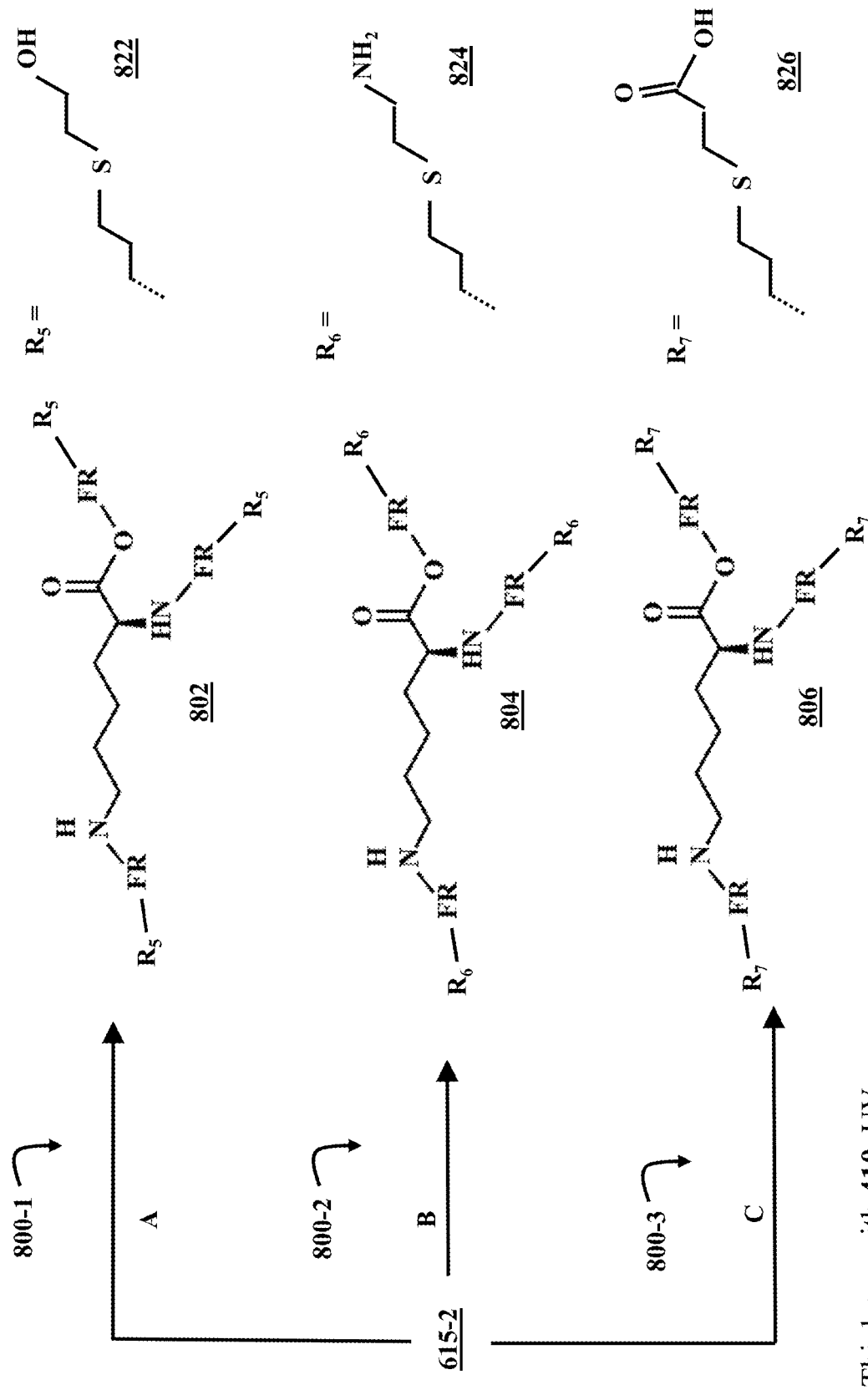
FIG. 8A is a chemical reaction diagram illustrating three processes of synthesizing thioether-linked flame retardant lysine-derived cross-linkers, in accordance with embodiments of the present disclosure.

FIG. 8A is a chemical reaction diagram illustrating three processes 800-1, 800-2, and 800-3 of synthesizing thioether-linked flame retardant lysine-derived cross-linkers, in accordance with embodiments of the present disclosure. Each process is a thiol-ene reaction between the allyl functionalized flame retardant lysine cross-linker 615-2 and a thiol molecule. The thiol molecules used in processes 800-1, 800-2, and 800-3 are 2-mercaptoethanol 410, cysteamine HCl 420, and 3-mercaptopropionate 430, respectively. The structures of these thiol molecules are illustrated in FIG. 4.

In process 800-1 the allyl functionalized flame retardant lysine cross-linker 615-2 is reacted with 2-mercaptoethanol 410 under UV light. The resulting hydroxyl-functionalized flame retardant lysine-derived cross-linker 802 has thioether $R_5$ groups 822 that correspond to 2-mercaptoethanol 410. In process 800-2 the allyl functionalized flame retardant lysine cross-linker 615-2 is reacted with cysteamine HCl 420 in a pH of approximately 8-11 methanol (MeOH) solution under UV light. The resulting amino-functionalized flame retardant lysine-derived cross-linker 804 has thioether $R_6$ groups 824 that correspond to cysteamine HCl 420. In process 800-3 the allyl functionalized flame retardant lysine cross-linker 615-2 is reacted with 2-mercaptopropionate 430 under UV light in a methanol (MeOH) solution. The resulting carboxylic acid-functionalized flame retardant lysine-derived cross-linker 806 has thioether $R_7$ groups 826 that correspond to 3-mercaptopropionate 430.

Figure 8B:
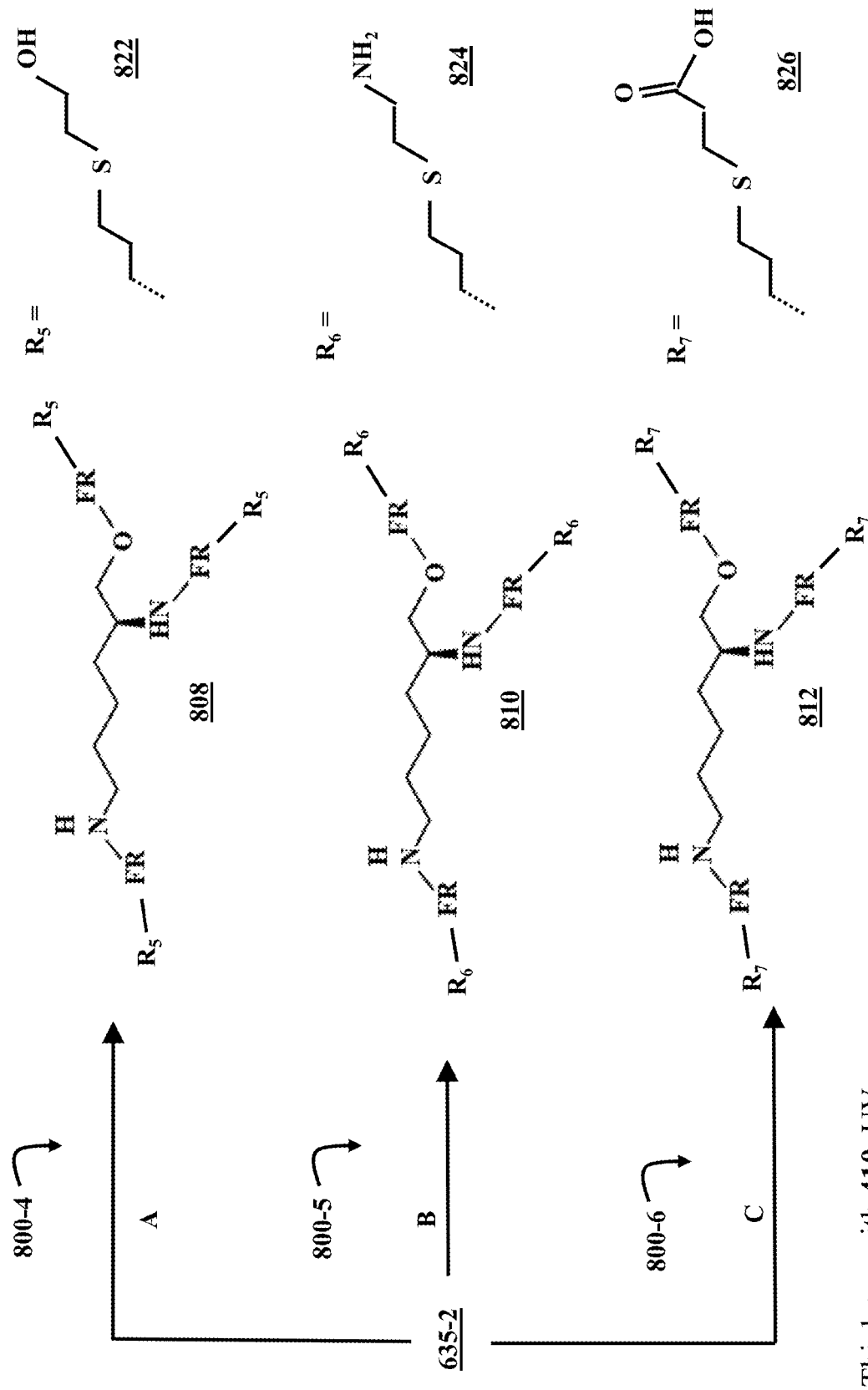
FIG. 8B is a chemical reaction diagram illustrating three processes of synthesizing thioether-linked flame retardant reduced lysine-derived cross-linkers, in accordance with embodiments of the present disclosure.

FIG. 8B is a chemical reaction diagram illustrating three processes 800-4, 800-5, and 800-6 of synthesizing thioether-linked flame retardant reduced lysine-derived cross-linkers, in accordance with embodiments of the present disclosure. Each process is a thiol-ene reaction between the allyl functionalized flame retardant reduced lysine cross-linker 635-2 and a thiol molecule. The thiol molecules used in processes 800-4, 800-5, and 800-6 are 2-mercaptoethanol 410, cysteamine HCl 420, and 3-mercaptopropionate 430, respectively. The structures of these thiol molecules are illustrated in FIG. 4.

In process 800-4, the allyl functionalized flame retardant reduced lysine cross-linker 635-2 is reacted with 2-mercaptoethanol 410 under UV light. The resulting hydroxyl-functionalized flame retardant reduced lysine-derived cross-linker 808 has thioether $R_5$ groups 822 that correspond to 2-mercaptoethanol 410. In process 800-5 the allyl functionalized flame retardant reduced lysine cross-linker 635-2 is reacted with cysteamine HCl 420 in a pH of approximately 8-11 methanol (MeOH) solution under UV light. The resulting amino-functionalized flame retardant reduced lysine-derived cross-linker 810 has thioether $R_6$ groups 824 that correspond to cysteamine HCl 420. In process 800-6, the allyl functionalized flame retardant reduced lysine cross-linker 635-2 is reacted with 2-mercaptopropionate 430 under UV light in a methanol (MeOH) solution. The resulting carboxylic acid-functionalized flame retardant reduced lysine-derived cross-linker 812 has thioether $R_7$ groups 826 that correspond to 3-mercaptopropionate 430.

Figure 8C:
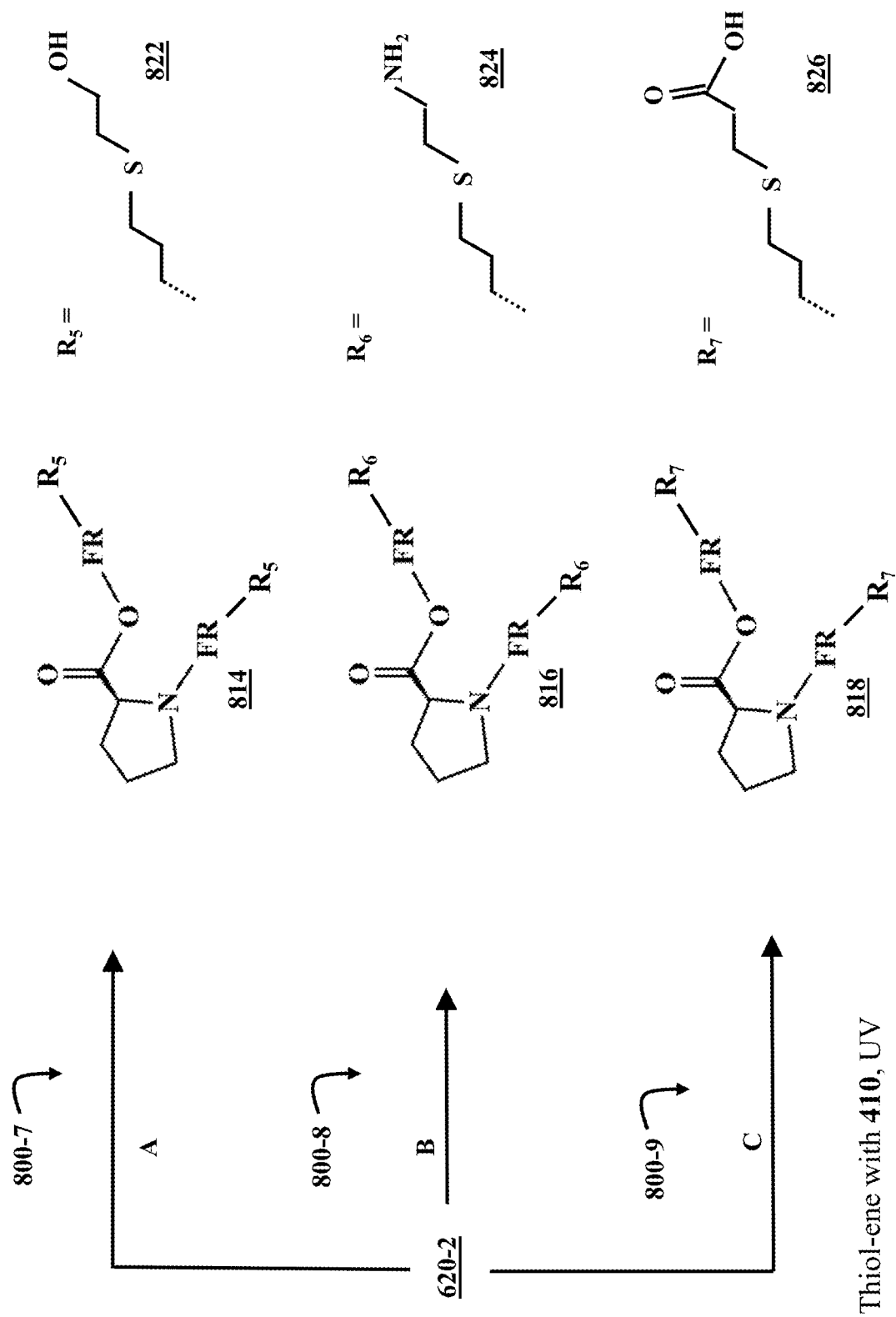
FIG. 8C is a chemical reaction diagram illustrating three processes of synthesizing thioether-linked flame retardant proline-derived cross-linkers, in accordance with embodiments of the present disclosure.

FIG. 8C is a chemical reaction diagram illustrating three processes 800-7, 800-8, and 800-9 of synthesizing thioether-linked flame retardant proline-derived cross-linkers, in accordance with embodiments of the present disclosure. Each process is a thiol-ene reaction between the allyl functionalized flame retardant proline cross-linker 620-2 and a thiol molecule. The thiol molecules used in processes 800-7, 800-8, and 800-9 are 2-mercaptoethanol 410, cysteamine HCl 420, and 3-mercaptopropionate 430, respectively. The structures of these thiol molecules are illustrated in FIG. 4.

In process 800-7 the allyl functionalized flame retardant proline cross-linker 620-2 is reacted with 2-mercaptoethanol 410 under UV light. The resulting hydroxyl-functionalized flame retardant proline-derived cross-linker 814 has thioether $R_5$ groups 822 that correspond to 2-mercaptoethanol 410. In process 800-8 the allyl functionalized flame retardant proline cross-linker 620-2 is reacted with cysteamine HCl 420 in a pH of approximately 8-11 methanol (MeOH) solution under UV light. The resulting amino-functionalized flame retardant proline-derived cross-linker 816 has thioether $R_6$ groups 824 that correspond to cysteamine HCl 420. In process 800-9 the allyl functionalized flame retardant proline cross-linker 620-2 is reacted with 2-mercaptopropionate 430 under UV light in a methanol (MeOH) solution. The resulting carboxylic acid-functionalized flame retardant proline-derived cross-linker 818 has thioether $R_7$ groups 826 that correspond to 3-mercaptopropionate 430.

Figure 8D:
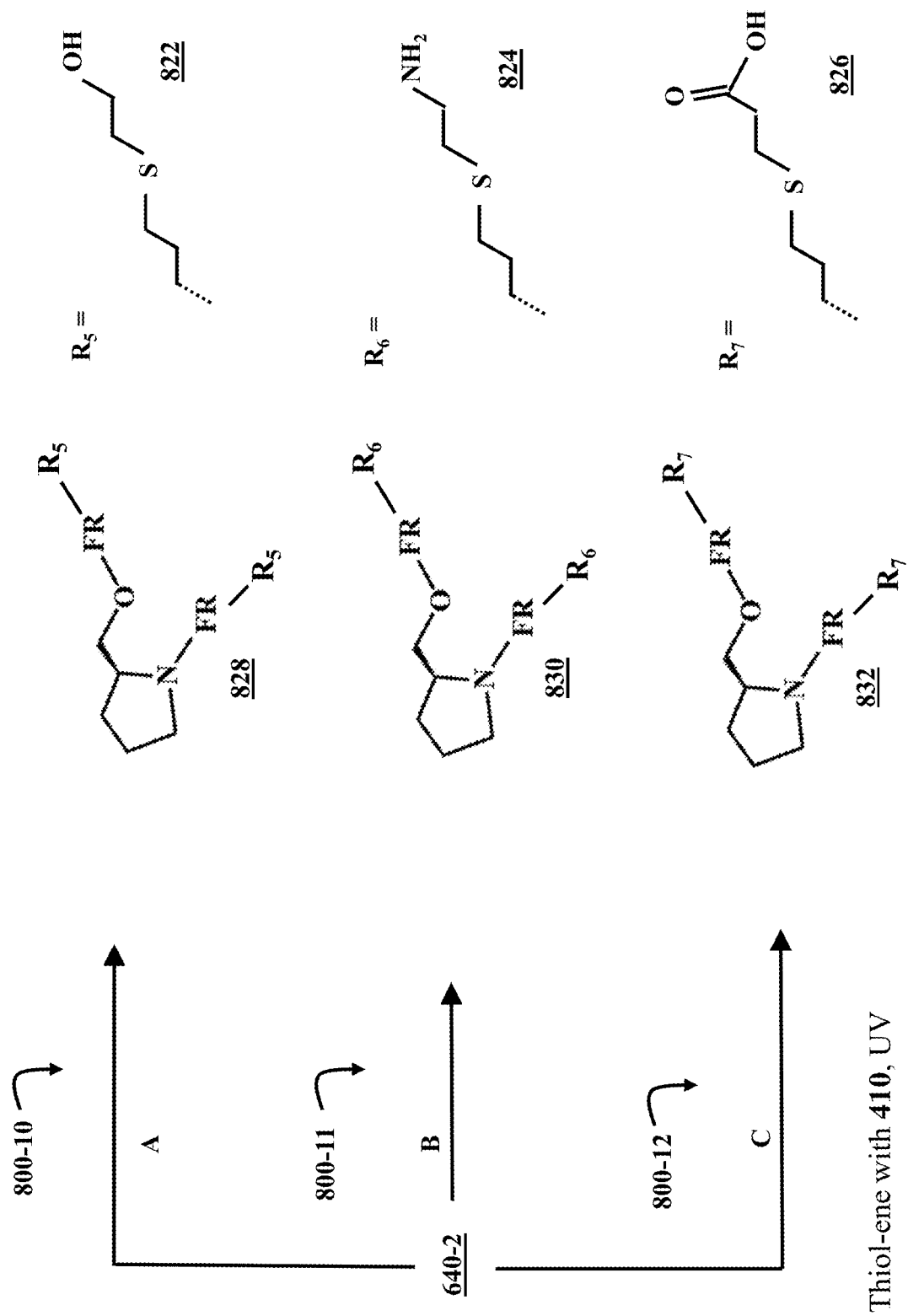
FIG. 8D is a chemical reaction diagram illustrating three processes of synthesizing thioether-linked flame retardant reduced proline-derived cross-linkers, in accordance with embodiments of the present disclosure.

FIG. 8D is a chemical reaction diagram illustrating three processes 800-10, 800-11, and 800-12 of synthesizing thioether-linked flame retardant reduced proline-derived cross-linkers, in accordance with embodiments of the present disclosure. Each process is a thiol-ene reaction between the allyl functionalized flame retardant reduced proline cross-linker 640-2 and a thiol molecule. The thiol molecules used in processes 800-10, 800-11, and 800-12 are 2-mercaptoethanol 410, cysteamine HCl 420, and 3-mercaptopropionate 430, respectively. The structures of these thiol molecules are illustrated in FIG. 4.

In process 800-10 the allyl functionalized flame retardant reduced proline cross-linker 640-2 is reacted with 2-mercaptoethanol 410 under UV light. The resulting hydroxyl-functionalized flame retardant reduced proline-derived cross-linker 828 has thioether $R_5$ groups 822 that correspond to 2-mercaptoethanol 410. In process 800-11 the allyl functionalized flame retardant reduced proline cross-linker 640-2 is reacted with cysteamine HCl 420 in a pH of approximately 8-11 methanol (MeOH) solution under UV light. The resulting amino-functionalized flame retardant reduced proline-derived cross-linker 830 has thioether $R_6$ groups 824 that correspond to cysteamine HCl 420. In process 800-12 the allyl functionalized flame retardant reduced proline cross-linker 640-2 is reacted with 2-mercaptopropionate 430 under UV light in a methanol (MeOH) solution. The resulting carboxylic acid-functionalized flame retardant reduced proline-derived cross-linker 832 has thioether $R_7$ groups 826 that correspond to 3-mercaptopropionate 430.

Figure 8E:
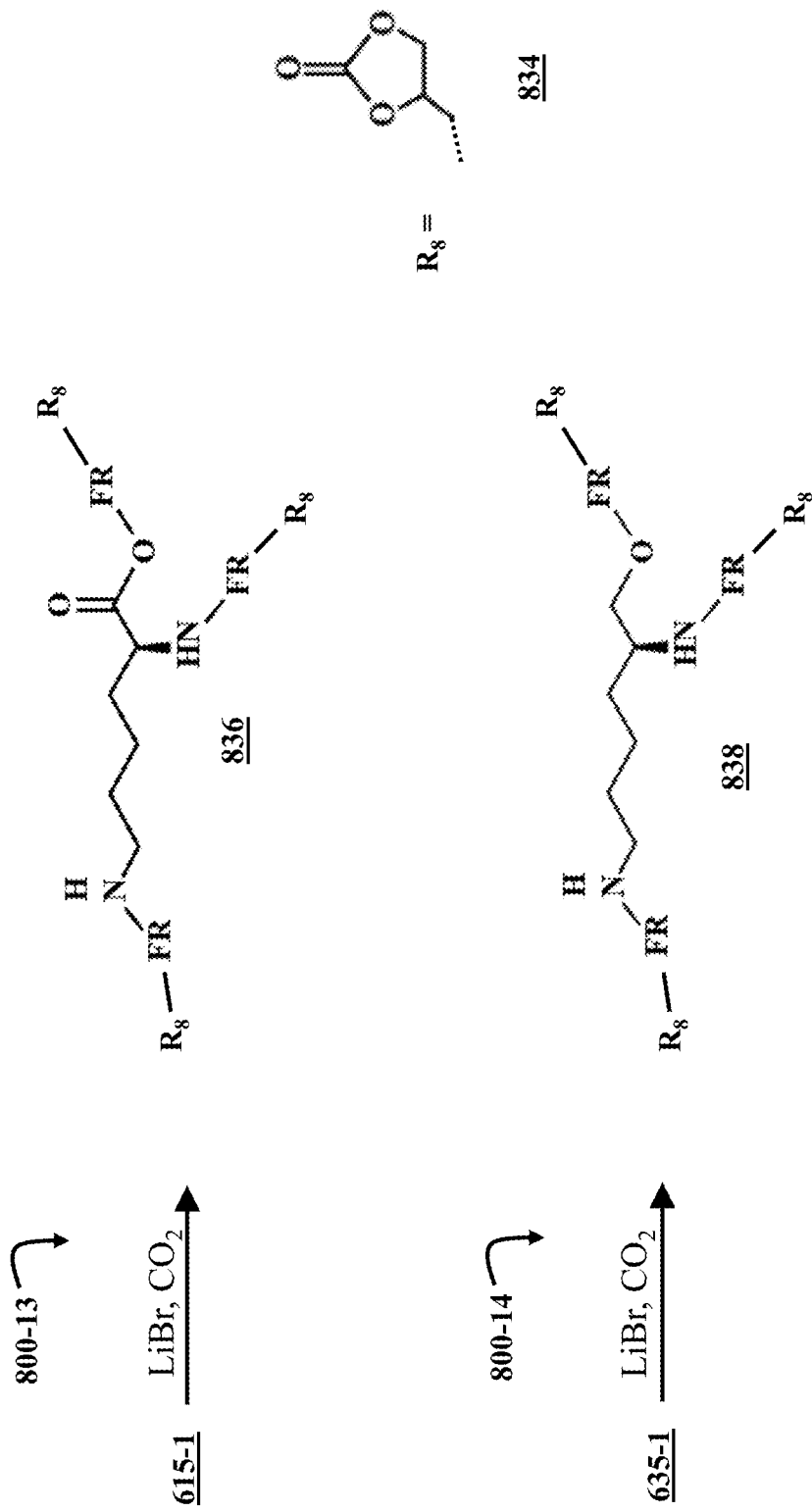
FIG. 8E is a chemical reaction diagram illustrating a process of synthesizing a propylene carbonate-functionalized flame retardant lysine-derived cross-linker and a process of synthesizing propylene carbonate-functionalized flame retardant reduced lysine-derived cross-linker, in accordance with embodiments of the present disclosure.

FIG. 8E is a chemical reaction diagram illustrating processes 800-13 and 800-14 of synthesizing a propylene carbonate-functionalized flame retardant lysine-derived cross-linker 836 and a propylene carbonate-functionalized flame retardant reduced lysine-derived cross-linker 838, in accordance with embodiments of the present disclosure. In process 800-13 the epoxy functionalized flame retardant lysine cross-linker 615-1 is combined with lithium bromide (LiBr). Carbon dioxide ($CO_2$) is added to the mixture, either by injecting into the headspace of the reaction flask, or by bubbling through the solution. This step yields the propylene carbonate-functionalized flame retardant lysine-derived cross-linker 836 with a propylene carbonate $R_8$ functional group 834. In process 800-14 the epoxy functionalized flame retardant reduced lysine cross-linker 635-1 is combined with lithium bromide (LiBr). Carbon dioxide ($CO_2$) is added to the mixture, either by injecting into the headspace of the reaction flask, or by bubbling through the solution. This step yields the propylene carbonate-functionalized flame retardant reduced lysine-derived cross-linker 838 with a propylene carbonate $R_8$ functional group 834.

Figure 8F:
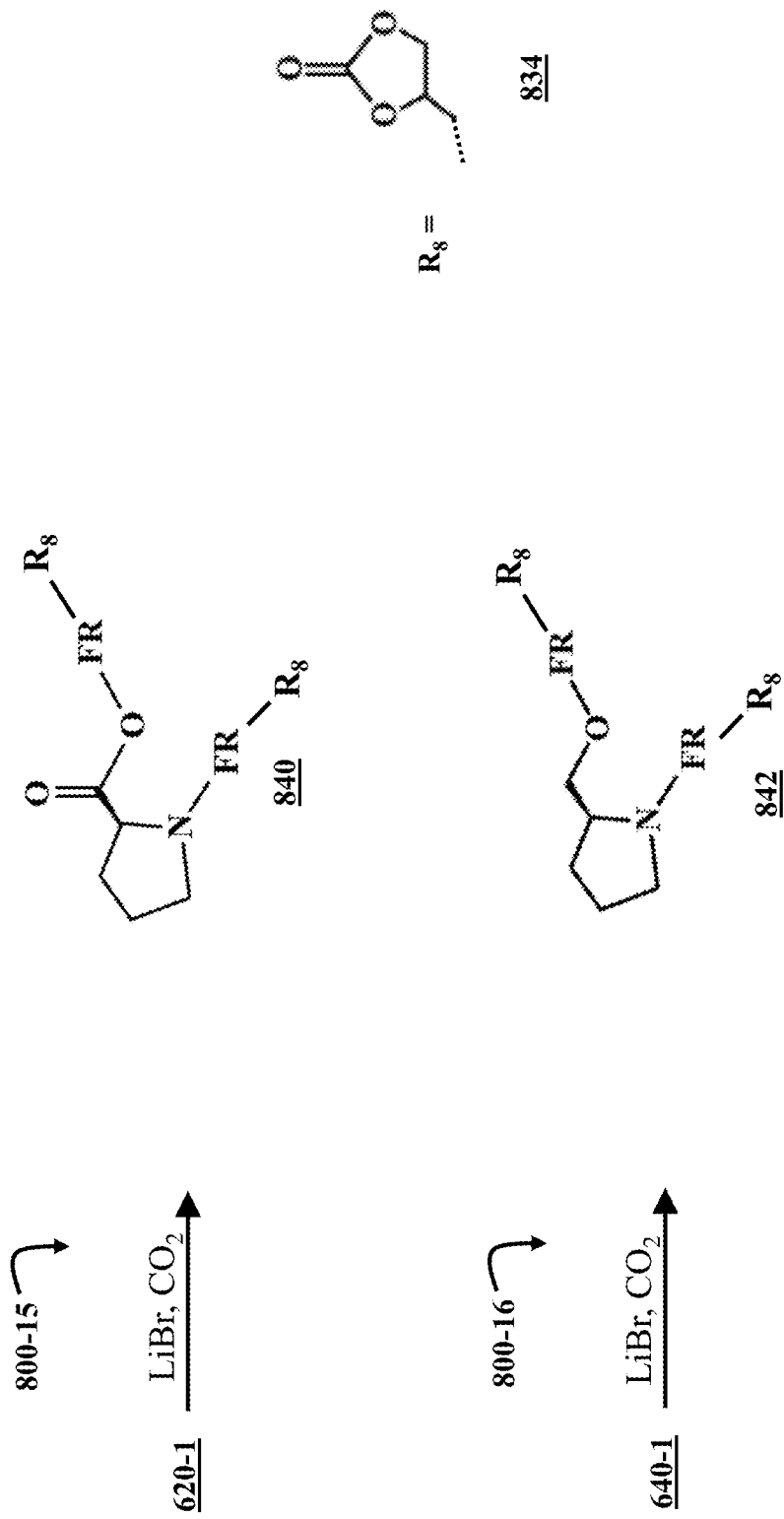
FIG. 8F is a chemical reaction diagram illustrating a process of synthesizing a propylene carbonate-functionalized flame retardant proline-derived cross-linker and a process of synthesizing a propylene carbonate-functionalized flame retardant reduced proline-derived cross-linker, in accordance with embodiments of the present disclosure.

FIG. 8F is a chemical reaction diagram illustrating processes 800-15 and 800-16 of synthesizing a propylene carbonate-functionalized flame retardant proline-derived cross-linker 840 and a propylene carbonate-functionalized flame retardant reduced proline-derived cross-linker 842, in accordance with embodiments of the present disclosure. In process 800-15 the epoxy functionalized flame retardant proline cross-linker 620-1 is combined with lithium bromide (LiBr). Carbon dioxide ($CO_2$) is added to the mixture, either by injecting into the headspace of the reaction flask, or by bubbling through the solution. This step yields the propylene carbonate-functionalized flame retardant proline-derived cross-linker 840 with a propylene carbonate $R_8$ functional group 834. In process 800-16 the epoxy functionalized flame retardant reduced proline cross-linker 640-1 is combined with lithium bromide (LiBr). Carbon dioxide ($CO_2$) is added to the mixture, either by injecting into the headspace of the reaction flask, or by bubbling through the solution. This step yields the propylene carbonate-functionalized flame retardant reduced proline-derived cross-linker 842 with a propylene carbonate $R_8$ functional group 834.

Figure 9A:
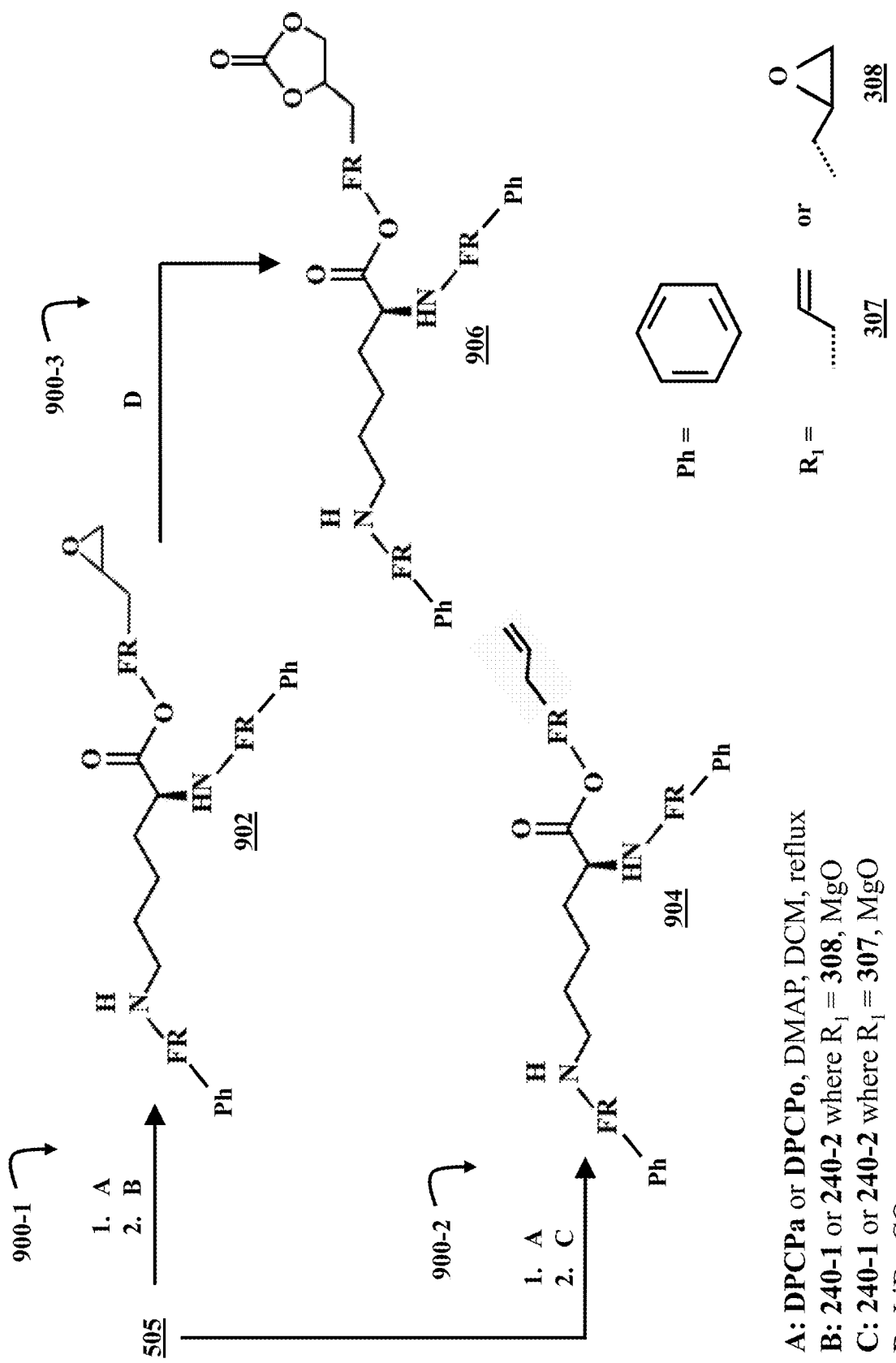
FIG. 9A is a chemical reaction diagram illustrating three processes of forming monofunctionalized flame retardant lysine-derived molecules, in accordance with embodiments of the present disclosure.

FIG. 9A is a chemical reaction diagram illustrating three processes 900-1, 900-2, and 900-3 of forming monofunctionalized flame retardant lysine derived molecules 902, 904 and 906, in accordance with embodiments of the present disclosure. In process 900-1, lysine 505 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. The resulting molecules are then reacted with the phosphorus-based flame retardant molecule 240 (e.g., 240-1 or 240-2), where the $R_1$ functional group is an epoxy functional group 308, and magnesium oxide (MgO) to yield an epoxy monofunctionalized flame retardant lysine derived molecule 902. If the process is carried out with DPCPa, the epoxy monofunctionalized flame retardant lysine derived molecule 902 will have phosphoryl FR groups, and, if the reaction is carried out with DPCPo, the epoxy monofunctionalized flame retardant lysine-derived molecule 902 will have phosphonyl FR groups.

In process 900-2, lysine 505 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. Further, in process 900-2, the resulting molecules are then reacted with the phosphorus-based flame retardant molecule 240, where the $R_1$ functional group is an allyl functional group 307, and magnesium oxide (MgO) to yield an allyl monofunctionalized flame retardant lysine-derived molecule 904. If the process is carried out with DPCPa, the allyl monofunctionalized flame retardant lysine-derived molecule 904 will have phosphoryl FR groups, and, if the reaction is carried out with DPCPo, the allyl monofunctionalized flame retardant lysine-derived molecule 904 will have phosphonyl FR groups.

In process 900-3, the epoxy monofunctionalized flame retardant lysine-derived molecule 902 is combined with lithium bromide (LiBr). Carbon dioxide ($CO_2$) is added to the mixture, either by injecting it into the headspace of the reaction flask, or by bubbling it through the solution. This process yields a propylene carbonate monofunctionalized flame retardant lysine-derived molecule 906.

Figure 9B:
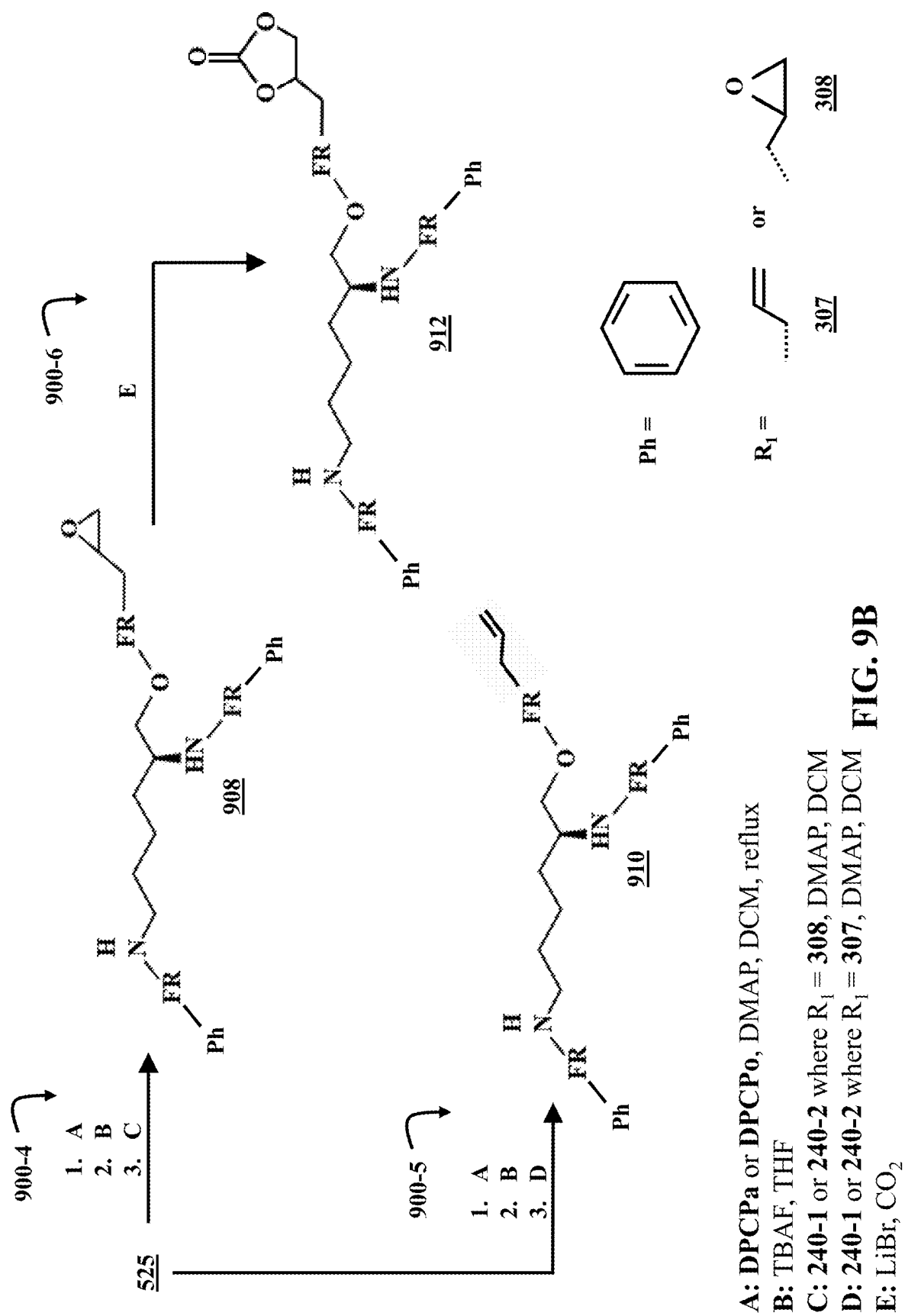
FIG. 9B is a chemical reaction diagram illustrating three processes of forming monofunctionalized flame retardant reduced lysine-derived molecules, in accordance with embodiments of the present disclosure.

FIG. 9B is a chemical reaction diagram illustrating three processes 900-4, 900-5, and 900-6 of forming monofunctionalized flame retardant reduced lysine-derived molecules 908, 910, and 912, in accordance with embodiments of the present disclosure. In process 900-4, protected reduced lysine 525 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. Next, the protected reduced lysine with diphenyl functionalized FR groups bound to the amine functional groups are reacted with tetra-n-butylammonium fluoride (TBAF) and tetrahydrofuran (THF) to deprotect the hydroxyl group present on the protected reduced lysine 525. After deprotection, the resulting molecules are then reacted with the phosphorus-based flame retardant molecule 240, where the $R_1$ functional group is an epoxy functional group 308, and magnesium oxide (MgO) to yield an epoxy monofunctionalized flame retardant reduced lysine-derived molecule 908. If the process is carried out with DPCPa, the epoxy monofunctionalized flame retardant reduced lysine-derived molecule 908 will have phosphoryl FR groups, and, if the reaction is carried out with DPCPo, the epoxy monofunctionalized flame retardant reduced lysine-derived molecule 908 will have phosphonyl FR groups.

In process 900-5, protected reduced lysine 525 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. Next, the protected reduced lysine with diphenyl functionalized FR groups bound to the amine functional groups are reacted with tetra-n-butylammonium fluoride (TBAF) and tetrahydrofuran (THF) to deprotect the hydroxyl group present on the protected reduced lysine 525. After deprotection, the resulting molecules are then reacted with the phosphorus-based flame retardant molecule 240, where the $R_1$ functional group is an allyl functional group 307, and magnesium oxide (MgO) to yield an allyl monofunctionalized flame retardant reduced lysine-derived molecule 910. If the process is carried out with DPCPa, the allyl monofunctionalized flame retardant reduced lysine-derived molecule 910 will have phosphoryl FR groups, and, if the reaction is carried out with DPCPo, the allyl monofunctionalized flame retardant reduced lysine-derived molecule 910 will have phosphonyl FR groups.

In process 900-6, the epoxy monofunctionalized flame retardant reduced lysine-derived molecule 908 is combined with lithium bromide (LiBr). Carbon dioxide ($CO_2$) is added to the mixture, either by injecting it into the headspace of the reaction flask, or by bubbling it through the solution. This process yields a propylene carbonate monofunctionalized flame retardant reduced lysine-derived molecule 912.

Figure 9C:
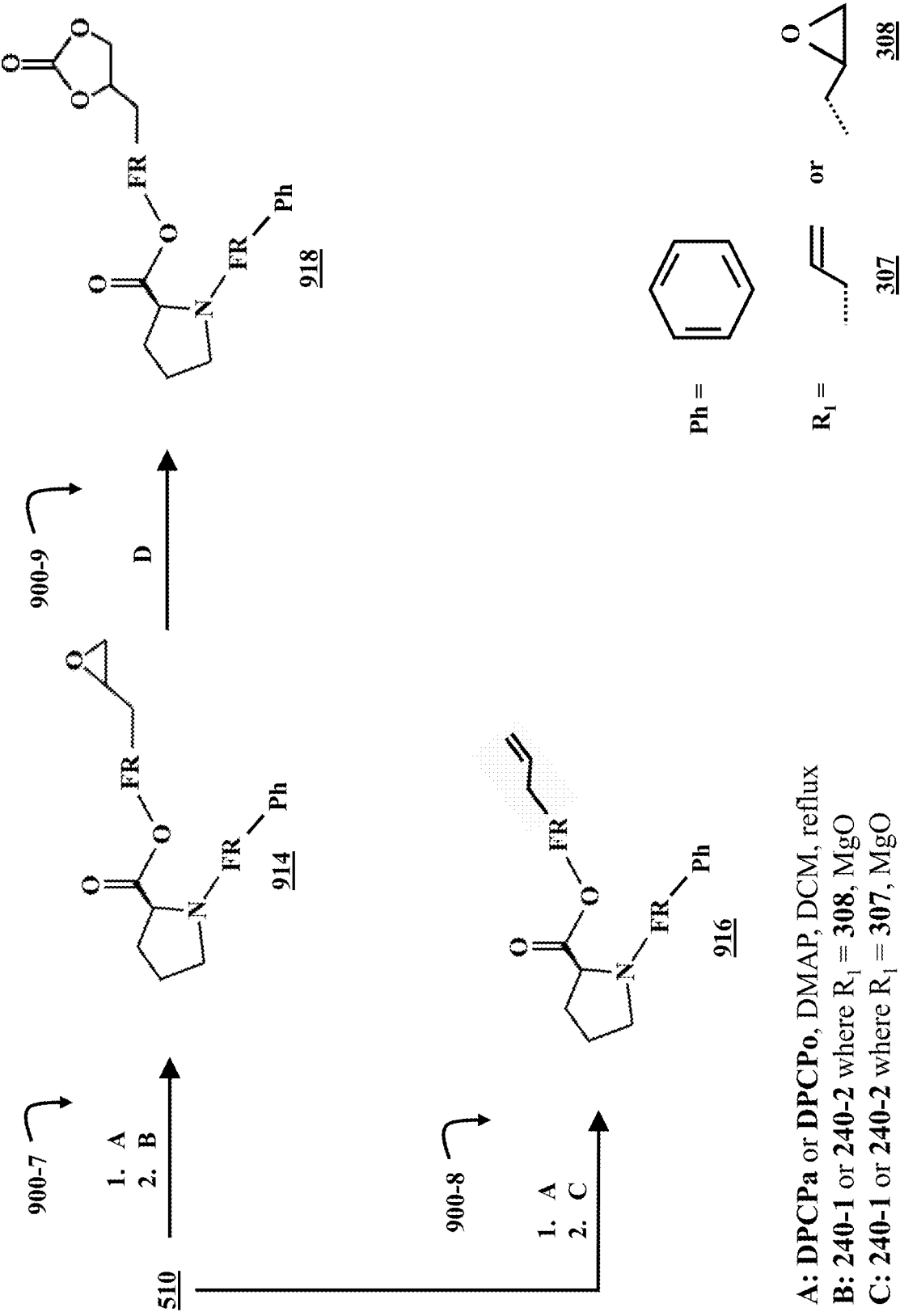
FIG. 9C is a chemical reaction diagram illustrating three processes of forming monofunctionalized flame retardant proline-derived molecules, in accordance with embodiments of the present disclosure.

FIG. 9C is a chemical reaction diagram illustrating three processes 900-7, 900-8, and 900-9 of forming monofunctionalized flame retardant proline-derived molecules 914, 916, and 918, in accordance with embodiments of the present disclosure. In process 900-7, proline 510 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. The resulting molecules are then reacted with the phosphorus-based flame retardant molecule 240, where the $R_1$ functional group is an epoxy functional group 308, and magnesium oxide (MgO) to yield an epoxy monofunctionalized flame retardant proline-derived molecule 914. If the process is carried out with DPCPa, the epoxy monofunctionalized flame retardant proline-derived molecule 914 will have phosphoryl FR groups, and, if the reaction is carried out with DPCPo, the epoxy monofunctionalized flame retardant proline-derived molecule 914 will have phosphonyl FR groups.

In process 900-8, proline 510 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. The resulting molecules are then reacted with the phosphorus-based flame retardant molecule 240, where the $R_1$ functional group is an allyl functional group 307, and magnesium oxide (MgO) to yield an allyl monofunctionalized flame retardant proline-derived molecule 916. If the process is carried out with DPCPa, the allyl monofunctionalized flame retardant proline-derived molecule 916 will have phosphoryl FR groups, and, if the reaction is carried out with DPCPo, the allyl monofunctionalized flame retardant proline-derived molecule 916 will have phosphonyl FR groups.

In process 900-9, the epoxy monofunctionalized flame retardant proline-derived molecule 914 is combined with lithium bromide (LiBr). Carbon dioxide ($CO_2$) is added to the mixture, either by injecting it into the headspace of the reaction flask, or by bubbling it through the solution. This process yields a propylene carbonate monofunctionalized flame retardant proline-derived molecule 918.

Figure 9D:
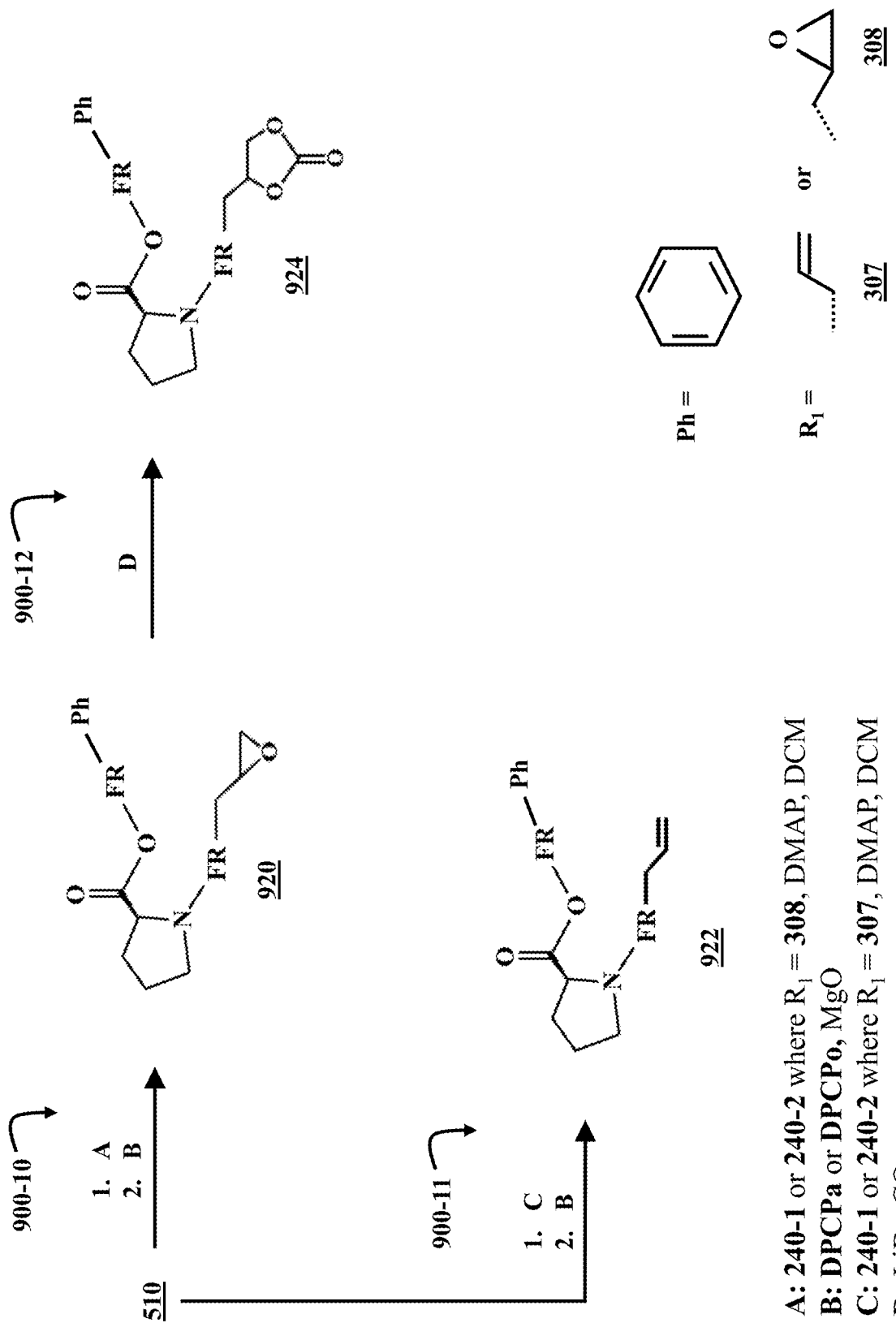
FIG. 9D is a chemical reaction diagram illustrating three processes of forming monofunctionalized flame retardant proline-derived molecules, in accordance with embodiments of the present disclosure.

FIG. 9D is a chemical reaction diagram illustrating three processes 900-10, 900-11, and 900-12 of forming monofunctionalized flame retardant proline-derived molecules 920, 922, and 924, in accordance with embodiments of the present disclosure. The monofunctionalized flame retardant proline-derived molecules formed in FIG. 9D differ from the monofunctionalized flame retardant proline-derived molecules illustrated in FIG. 9C, as the diphenyl FR is bound to the carboxylic acid group in FIG. 9D as opposed to the amino group in FIG. 9C.

In process 900-10, proline 510 is reacted with the phosphorus-based flame retardant molecule 240, where the $R_1$ functional group is an epoxy functional group 308. The mixture is refluxed with catalytic dimethylaminopyridine (DMAP) in a dichloromethane (DCM) solution. In some embodiments, stoichiometric trimethylamine is used instead of DMAP. The resulting molecules are then reacted with either diphenyl chlorophosphate (DPCPa) or diphenylphosphinic chloride (DPCPo), and magnesium oxide (MgO) to yield an epoxy monofunctionalized flame retardant proline-derived molecule 920. If the process is carried out with DPCPa, the epoxy monofunctionalized flame retardant proline-derived molecule 920 will have phosphoryl FR groups, and, if the reaction is carried out with DPCPo, the epoxy monofunctionalized flame retardant proline-derived molecule 920 will have phosphonyl FR groups.

In process 900-11, proline 510 is reacted with the phosphorus-based flame retardant molecule 240, where the $R_1$ functional group is an allyl functional group 307. The mixture is refluxed with catalytic dimethylaminopyridine (DMAP) in a dichloromethane (DCM) solution. In some embodiments, stoichiometric trimethylamine is used instead of DMAP. Further, in process 900-11, the resulting molecules are then reacted with either diphenyl chlorophosphate (DPCPa) or diphenylphosphinic chloride (DPCPo), and magnesium oxide (MgO) to yield an allyl monofunctionalized flame retardant proline-derived molecule 922. If the process is carried out with DPCPa, the allyl monofunctionalized flame retardant proline-derived molecule 922 will have phosphoryl FR groups, and, if the reaction is carried out with DPCPo, the allyl monofunctionalized flame retardant proline-derived molecule 922 will have phosphonyl FR groups.

In process 900-12, the epoxy monofunctionalized flame retardant proline-derived molecule 920 is combined with lithium bromide (LiBr). Carbon dioxide ($CO_2$) is added to the mixture, either by injecting it into the headspace of the reaction flask, or by bubbling it through the solution. This process yields a propylene carbonate monofunctionalized flame retardant proline-derived molecule 924.

Figure 9E:
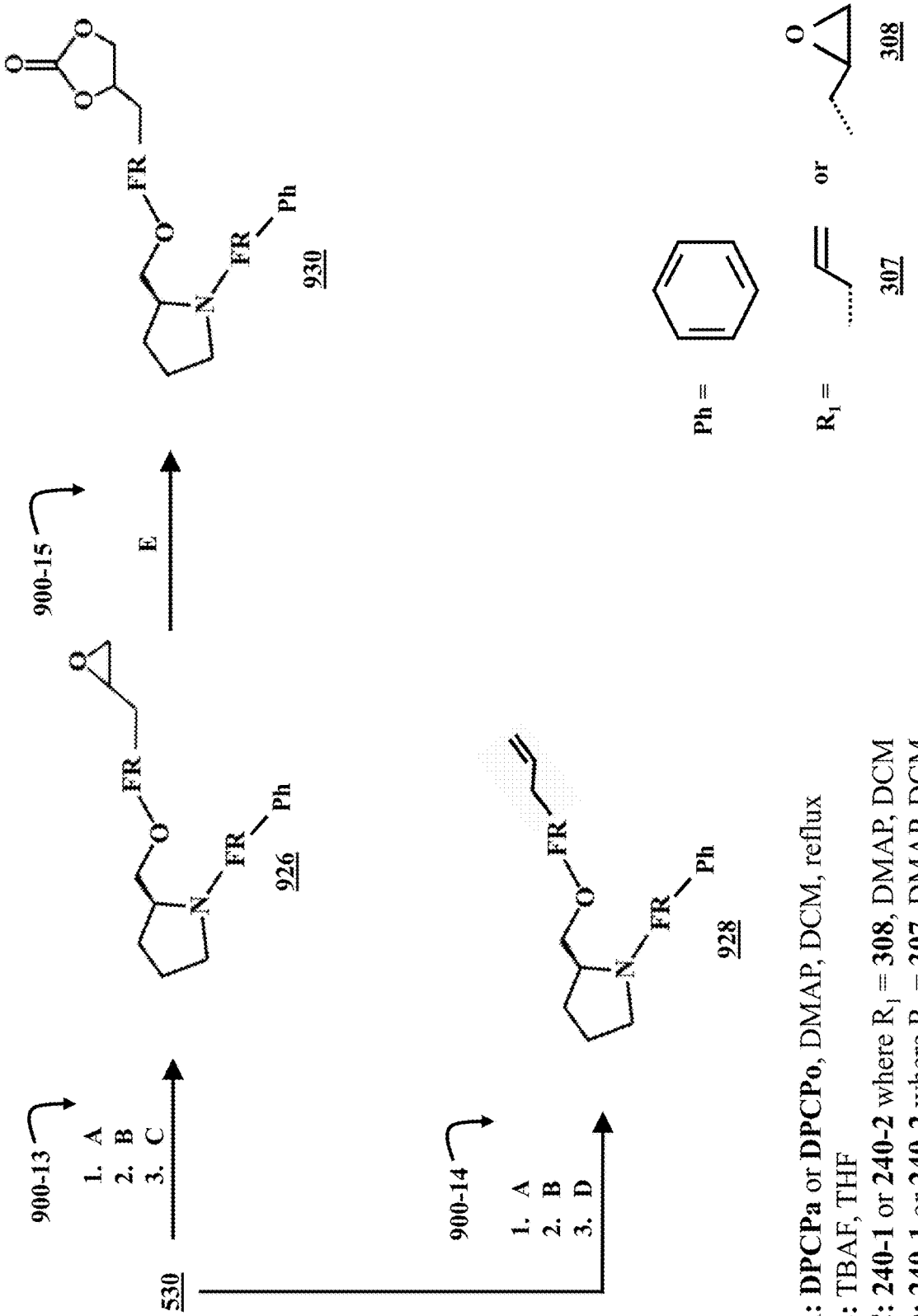
FIG. 9E is a chemical reaction diagram illustrating three processes of forming monofunctionalized flame retardant reduced proline-derived molecules, in accordance with embodiments of the present disclosure.

FIG. 9E is a chemical reaction diagram illustrating three processes 900-13, 900-14, and 900-15 of forming monofunctionalized flame retardant reduced proline-derived molecules 926, 928, and 930, in accordance with embodiments of the present disclosure. In process 900-13, protected reduced proline 530 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. Next, the protected reduced proline molecules with diphenyl functionalized FR groups bound to the amine functional groups are reacted with tetra-n-butylammonium fluoride (TBAF) and tetrahydrofuran (THF) to deprotect the hydroxyl group present on the protected reduced proline 530. After deprotection, the resulting molecules are then reacted with the phosphorus-based flame retardant molecule 240, where the $R_1$ functional group is an epoxy functional group 308, and magnesium oxide (MgO) to yield an epoxy monofunctionalized flame retardant reduced proline-derived molecule 926. If the process is carried out with DPCPa, the epoxy monofunctionalized flame retardant reduced proline-derived molecule 926 will have phosphoryl FR groups, and if the reaction is carried out with DPCPo, the epoxy monofunctionalized flame retardant reduced proline-derived molecule 926 will have phosphonyl FR groups.

In process 900-14, protected reduced proline 530 is reacted with either diphenyl chlorophosphate (DPCPa) or diphenylphosphinic chloride (DPCPo). The mixture is refluxed with catalytic dimethylaminopyridine (DMAP) in a dichloromethane (DCM) solution. In some embodiments, stoichiometric trimethylamine is used instead of DMAP. Next, the protected reduced proline molecules with diphenyl functionalized FR groups bound to the amine functional groups are reacted with tetra-n-butylammonium fluoride (TBAF) and tetrahydrofuran (THF) to deprotect the hydroxyl group present on the protected reduced proline 530. After deprotection, the resulting molecules are then reacted with the phosphorus-based flame retardant molecule 240, where the $R_1$ functional group is an allyl functional group 307, and magnesium oxide (MgO) to yield an allyl monofunctionalized flame retardant reduced proline-derived molecule 928. If the process is carried out with DPCPa, the allyl monofunctionalized flame retardant reduced proline-derived molecule 928 will have phosphoryl FR groups, and, if the reaction is carried out with DPCPo, the allyl monofunctionalized flame retardant reduced proline-derived molecule 928 will have phosphonyl FR groups.

In process 900-15, the epoxy monofunctionalized flame retardant reduced proline-derived molecule 926 is combined with lithium bromide (LiBr). Carbon dioxide ($CO_2$) is added to the mixture, either by injecting it into the headspace of the reaction flask, or by bubbling it through the solution. This process yields a propylene carbonate monofunctionalized flame retardant reduced proline-derived molecule 930.

Figure 9F:
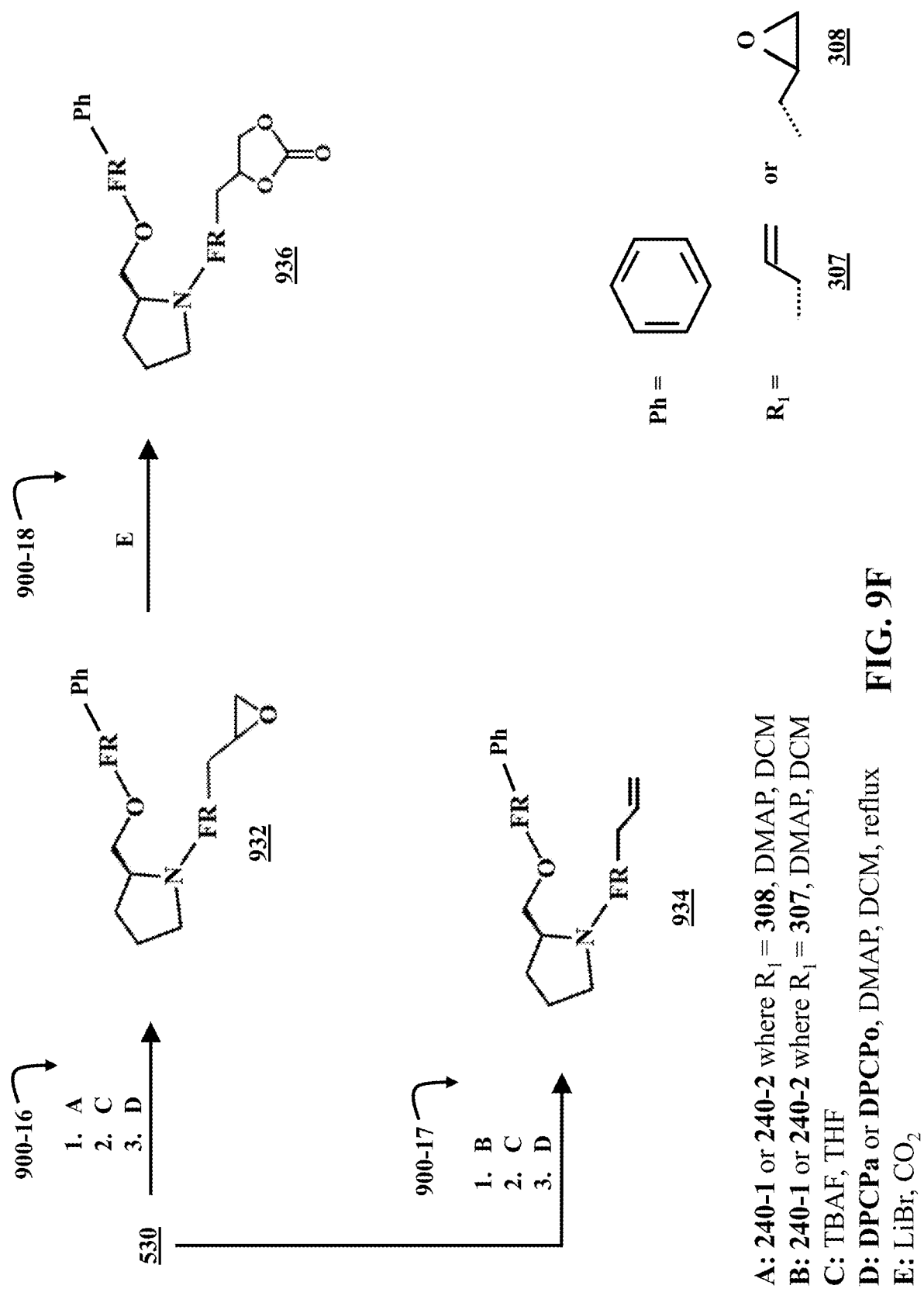
FIG. 9F is a chemical reaction diagram illustrating three processes of forming monofunctionalized flame retardant reduced proline-derived molecules, in accordance with embodiments of the present disclosure.

FIG. 9F is a chemical reaction diagram illustrating three processes 900-16, 900-17, and 900-18 of forming monofunctionalized flame retardant reduced proline-derived molecules 932, 934, and 936, in accordance with embodiments of the present disclosure. The monofunctionalized flame retardant reduced proline-derived molecules formed in FIG. 9F differ from the monofunctionalized flame retardant proline-derived molecules formed in FIG. 9E, as the diphenyl FR is bound to the carboxylic acid group in FIG. 9F as opposed to the amino group in FIG. 9E.

In process 900-16, protected reduced proline 530 is reacted with the phosphorus-based flame retardant molecule 240, where the $R_1$ functional group is an epoxy functional group 308. The mixture is refluxed with catalytic dimethylaminopyridine (DMAP) in a dichloromethane (DCM) solution. In some embodiments, stoichiometric trimethylamine is used instead of DMAP. Next, the protected reduced proline molecules with epoxy functionalized FR groups bound to the amine functional groups are reacted with tetra-n-butylammonium fluoride (TBAF) and tetrahydrofuran (THF) to deprotect the hydroxyl group present on the protected reduced proline 530. After deprotection, the resulting molecules are then reacted with either diphenyl chlorophosphate (DPCPa) or diphenylphosphinic chloride (DPCPo), and magnesium oxide (MgO) to yield an epoxy monofunctionalized flame retardant reduced proline-derived molecule 932. If the process is carried out with DPCPa, the epoxy monofunctionalized flame retardant reduced proline-derived molecule 932 will have phosphoryl FR groups, and, if the reaction is carried out with DPCPo, the epoxy monofunctionalized flame retardant reduced proline-derived molecule 932 will have phosphonyl FR groups.

In process 900-17, protected reduced proline 530 is reacted with the phosphorus-based flame retardant molecule 240, where the $R_1$ functional group is an allyl functional group 307. The mixture is refluxed with catalytic dimethylaminopyridine (DMAP) in a dichloromethane (DCM) solution. In some embodiments, stoichiometric trimethylamine is used instead of DMAP. Next, the protected reduced proline molecules with allyl functionalized FR groups bound to the amine functional groups are reacted with tetra-n-butylammonium fluoride (TBAF) and tetrahydrofuran (THF) to deprotect the hydroxyl group present on the protected reduced proline 530. After deprotection, the resulting molecules are reacted with either diphenyl chlorophosphate (DPCPa) or diphenylphosphinic chloride (DPCPo), and magnesium oxide (MgO) to yield an allyl monofunctionalized flame retardant reduced proline-derived molecule 934. If the process is carried out with DPCPa, the allyl monofunctionalized flame retardant reduced proline-derived molecule 934 will have phosphoryl FR groups, and if the reaction is carried out with DPCPo, the allyl monofunctionalized flame retardant reduced proline-derived molecule 934 will have phosphonyl FR groups.

In process 900-18, the epoxy monofunctionalized flame retardant reduced proline-derived molecule 932 is combined with lithium bromide (LiBr). Carbon dioxide ($CO_2$) is added to the mixture, either by injecting it into the headspace of the reaction flask, or by bubbling it through the solution. This process yields a propylene carbonate monofunctionalized flame retardant reduced proline-derived molecule 936.

With respect to FIG. 9A through FIG. 9F, the same reaction conditions as implemented in FIG. 8A through 8D can be implemented to synthesize thioether-linked monofunctionalized flame retardants. Specifically, allyl monofunctionalized flame retardant derivatives 904, 910, 916, 922, 928 and 934 can be reacted with thiol-ene molecules mercaptoethanol 410, cysteamine HCl 420, and 3-mercaptopropionate 430 (illustrated in FIG. 4) to yield monofunctionalized thioether-linked flame retardant molecules.

For example, allyl monofunctionalized flame retardant derivatives 904, 910, 916, 922, 928 and 934 can be reacted with 2-mercaptoethanol 410 under UV light, resulting in hydroxyl-monofunctionalized flame retardant derivatives. Allyl monofunctionalized flame retardant derivatives 904, 910, 916, 922, 928 and 934 can be reacted with cysteamine HCl 420 in a pH of approximately 8-11 methanol (MeOH) solution under UV light to yield amino-monofunctionalized flame retardant derivatives. Further, allyl monofunctionalized flame retardant derivatives 904, 910, 916, 922, 928 and 932 can be reacted with 2-mercaptopropionate 430 under UV light in a methanol (MeOH) solution to yield carboxylic acid-monofunctionalized flame retardant derivatives.

Figure 10A:
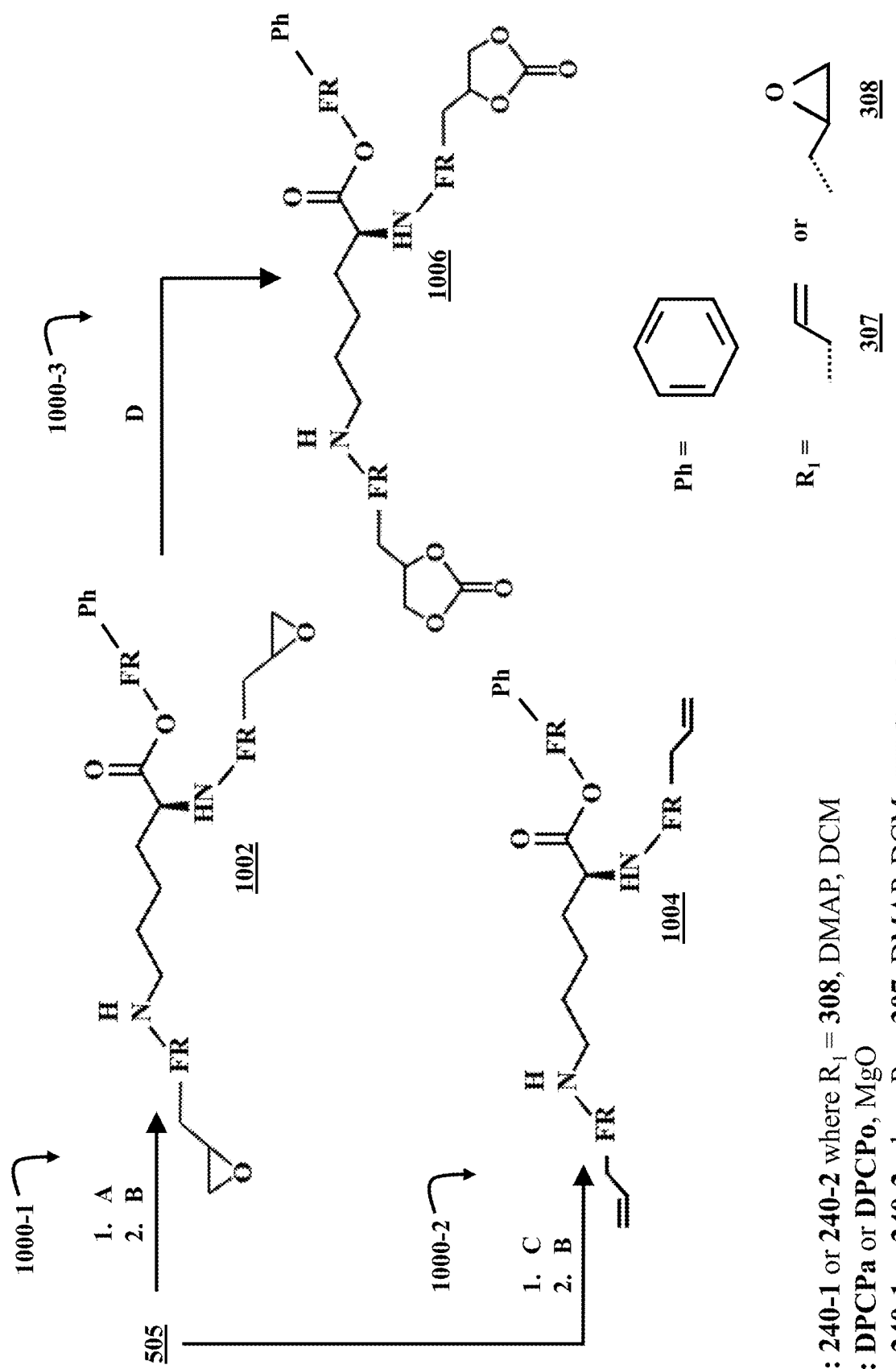
FIG. 10A is a chemical reaction diagram illustrating three processes of forming difunctionalized flame retardant lysine-derived molecules, in accordance with embodiments of the present disclosure.

FIG. 10A is a chemical reaction diagram illustrating three processes 1000-1, 1000-2, and 1000-3 of forming difunctionalized flame retardant lysine-derived molecules 1002, 1004, and 1006, in accordance with embodiments of the present disclosure. In process 1000-1, lysine 505 is reacted with the phosphorus-based flame retardant molecule 240, where the $R_1$ functional group is an epoxy functional group 308. The mixture is refluxed with catalytic dimethylaminopyridine (DMAP) in a dichloromethane (DCM) solution. In some embodiments, stoichiometric trimethylamine is used instead of DMAP. Further, in process 1000-1, the resulting molecules are then reacted with either diphenyl chlorophosphate (DPCPa) or diphenylphosphinic chloride (DPCPo), and magnesium oxide (MgO) to yield an epoxy difunctionalized flame retardant lysine-derived molecule 1002. If the process is carried out with DPCPa, the epoxy difunctionalized flame retardant lysine-derived molecule 1002 will have phosphoryl FR groups, and, if the reaction is carried out with DPCPo, the epoxy difunctionalized flame retardant lysine-derived molecule 1002 will have phosphonyl FR groups.

In process 1000-2, lysine 505 is reacted with the phosphorus-based flame retardant molecule 240, where the $R_1$ functional group is an allyl functional group 307. The mixture is refluxed with catalytic dimethylaminopyridine (DMAP) in a dichloromethane (DCM) solution. In some embodiments, stoichiometric trimethylamine is used instead of DMAP. Further, in process 1000-2, the resulting molecules are then reacted with either diphenyl chlorophosphate (DPCPa) or diphenylphosphinic chloride (DPCPo), and magnesium oxide (MgO) to yield an allyl difunctionalized flame retardant lysine-derived molecule 1004. If the process is carried out with DPCPa, the allyl difunctionalized flame retardant lysine-derived molecule 1004 will have phosphoryl FR groups, and, if the reaction is carried out with DPCPo, the allyl difunctionalized flame retardant lysine-derived molecule 1004 will have phosphonyl FR groups.

In process 1000-3, the epoxy difunctionalized flame retardant lysine-derived molecule 1002 is combined with lithium bromide (LiBr). Carbon dioxide ($CO_2$) is added to the mixture, either by injecting it into the headspace of the reaction flask, or by bubbling it through the solution. This process yields a propylene carbonate difunctionalized flame retardant lysine-derived molecule 1006.

Figure 10B:
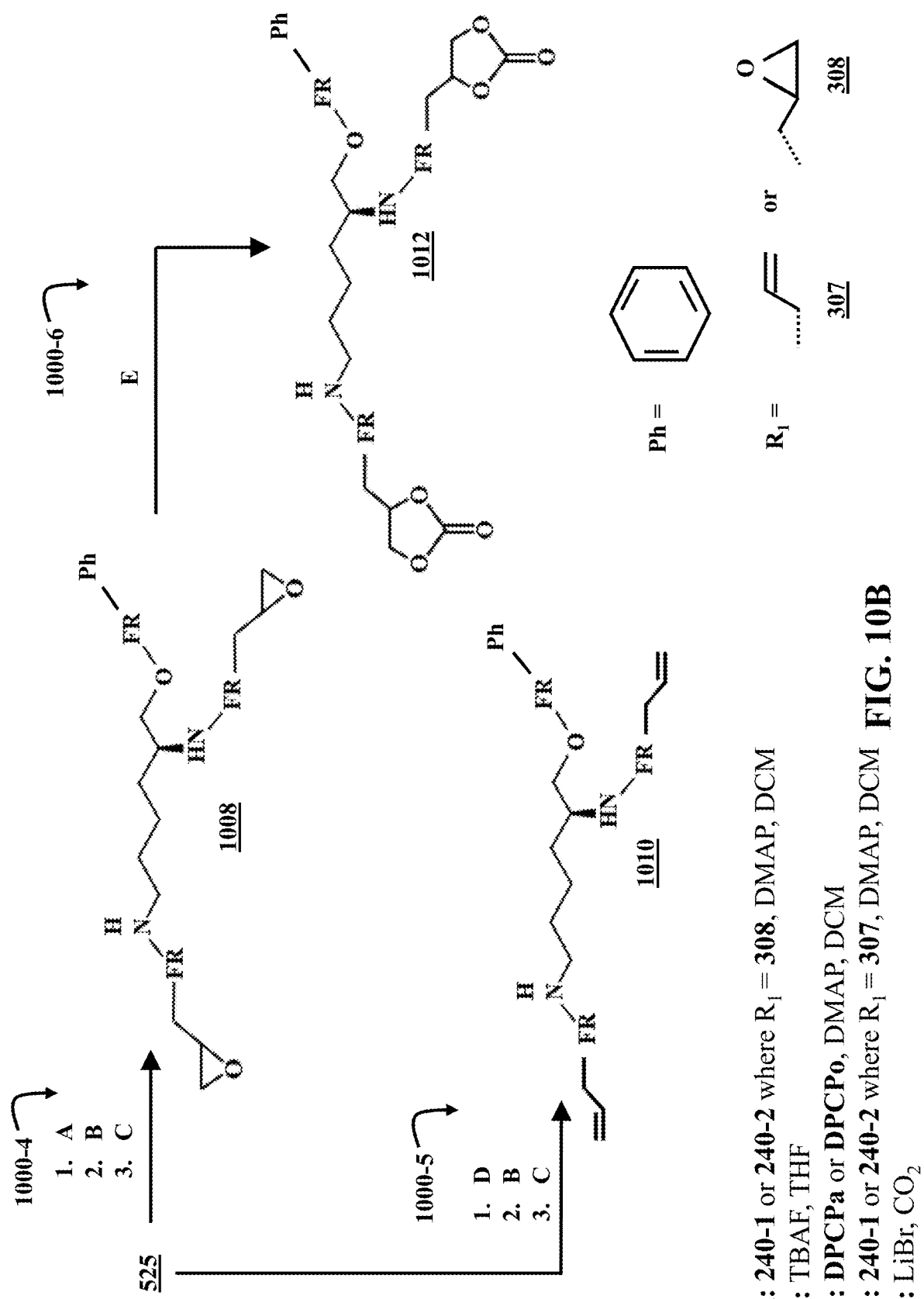
FIG. 10B is a chemical reaction diagram illustrating three processes of forming difunctionalized flame retardant reduced lysine-derived molecules, in accordance with embodiments of the present disclosure.

FIG. 10B is a chemical reaction diagram illustrating three processes 1000-4, 1000-5, and 1000-6 of forming difunctionalized flame retardant reduced lysine-derived molecules 1008, 1010, and 1012, in accordance with embodiments of the present disclosure. In process 1000-4, protected reduced lysine 525 is reacted with the phosphorus-based flame retardant molecule 240, where the $R_1$ functional group is an epoxy functional group 308. The mixture is refluxed with catalytic dimethylaminopyridine (DMAP) in a dichloromethane (DCM) solution. In some embodiments, stoichiometric trimethylamine is used instead of DMAP. Next, the protected reduced lysine molecules with epoxy functionalized FR groups bound to the amine functional groups are reacted with tetra-n-butylammonium fluoride (TBAF) and tetrahydrofuran (THF) to deprotect the hydroxyl group present on the protected reduced lysine 525. After deprotection, the resulting molecules are then reacted with either diphenyl chlorophosphate (DPCPa) or diphenylphosphinic chloride (DPCPo), and magnesium oxide (MgO) to yield an epoxy difunctionalized flame retardant reduced lysine-derived molecule 1008. If the process is carried out with DPCPa, the epoxy difunctionalized flame retardant reduced lysine-derived molecule 1008 will have phosphoryl FR groups, and, if the reaction is carried out with DPCPo, the epoxy difunctionalized flame retardant reduced lysine-derived molecule 1008 will have phosphonyl FR groups.

In process 1000-5, protected reduced lysine 525 is reacted with the phosphorus-based flame retardant molecule 240, where the $R_1$ functional group is an allyl functional group 307. The mixture is refluxed with catalytic dimethylaminopyridine (DMAP) in a dichloromethane (DCM) solution. In some embodiments, stoichiometric trimethylamine is used instead of DMAP. Next, the protected reduced lysine molecules with allyl functionalized FR groups bound to the amine functional groups are reacted with tetra-n-butylammonium fluoride (TBAF) and tetrahydrofuran (THF) to deprotect the hydroxyl group present on the protected reduced lysine 525. After deprotection, the resulting molecules are reacted with either diphenyl chlorophosphate (DPCPa) or diphenylphosphinic chloride (DPCPo), and magnesium oxide (MgO) to yield an allyl difunctionalized flame retardant reduced lysine-derived molecule 1010. If the process is carried out with DPCPa, the allyl difunctionalized flame retardant reduced lysine-derived molecule 1010 will have phosphoryl FR groups, and, if the reaction is carried out with DPCPo, the allyl difunctionalized flame retardant reduced lysine-derived molecule 1010 will have phosphonyl FR groups.

In process 1000-6, the epoxy difunctionalized flame retardant reduced lysine-derived molecule 1008 is combined with lithium bromide (LiBr). Carbon dioxide ($CO_2$) is added to the mixture, either by injecting it into the headspace of the reaction flask, or by bubbling it through the solution. This process yields a propylene carbonate difunctionalized flame retardant reduced lysine-derived molecule 1012.

With respect to FIG. 10A and FIG. 10B, the same reaction conditions as implemented in FIG. 8A through 8D can be implemented to synthesize thioether-linked difunctionalized lysine and reduced lysine flame retardants. Specifically, allyl difunctionalized flame retardant lysine and reduced lysine-derived molecules 1004 and 1010, respectively, can be reacted with thiol-ene molecules mercaptoethanol 410, cysteamine HCl 420, and 3-mercaptopropionate 430 (illustrated in FIG. 4) to yield difunctionalized thioether-linked flame retardant lysine and reduced lysine molecules.

For example, allyl difunctionalized flame retardant lysine and reduced lysine-derived molecules 1004 and 1010 can be reacted with 2-mercaptoethanol 410 under UV light, resulting in hydroxyl-difunctionalized flame retardant lysine and reduced lysine-derived molecules. Allyl difunctionalized flame retardant lysine and reduced lysine-derived molecules 1004 and 1010 can be reacted with cysteamine HCl 420 in a pH of approximately 8-11 methanol (MeOH) solution under UV light to yield amino-difunctionalized flame retardant lysine and reduced lysine-derived molecules. Further, allyl difunctionalized flame retardant lysine and reduced lysine-derived molecules 1004 and 1010 can be reacted with 2-mercaptopropionate 430 under UV light in a methanol (MeOH) solution to yield carboxylic acid-difunctionalized flame retardant lysine and reduced lysine-derived molecules.

Figure 11A:
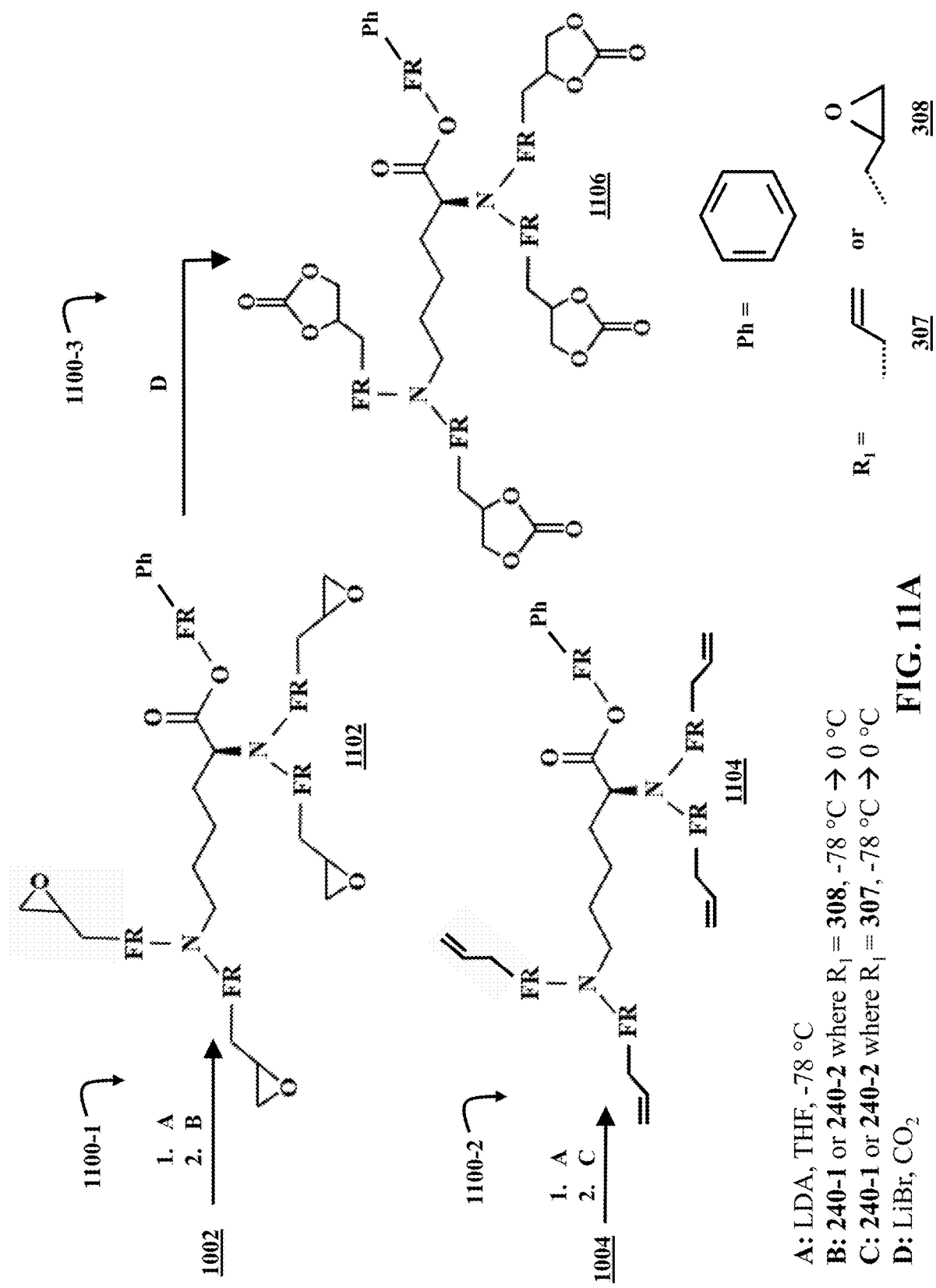
FIG. 11A is a chemical diagram illustrating three processes of synthesizing tetrafunctionalized flame retardant reduced lysine-derived molecules, in accordance with embodiments of the present disclosure.

FIG. 11A is a chemical diagram illustrating three processes 1100-1, 1100-2, and 1100-3 of synthesizing tetrafunctionalized flame retardant lysine-derived molecules 1102, 1104 and 1106, in accordance with embodiments of the present disclosure. In process 1100-1, the epoxy difunctionalized flame retardant lysine-derived molecule 1002 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an epoxy functional group 308 is added to the solution (e.g., dropwise, while stirring). The resulting mixture is then stirred for 16 hours while allowing it to warm gradually to room temperature. This yields an epoxy tetrafunctionalized flame retardant lysine-derived molecule 1102.

In process 1100-2, the allyl difunctionalized flame retardant lysine-derived molecule 1004 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an allyl functional group 308 is added to the solution (e.g., dropwise, while stirring). The resulting mixture is then stirred for 16 hours while allowing it to warm gradually to room temperature. This yields an allyl tetrafunctionalized flame retardant lysine-derived molecule 1104.

In process 1100-3, the epoxy tetrafunctionalized flame retardant lysine-derived molecule 1102 is combined with lithium bromide (LiBr). Carbon dioxide ($CO_2$) is added to the mixture, either by injecting it into the headspace of the reaction flask, or by bubbling it through the solution. This process yields a propylene carbonate tetrafunctionalized flame retardant lysine-derived molecule 1106.

Figure 11B:
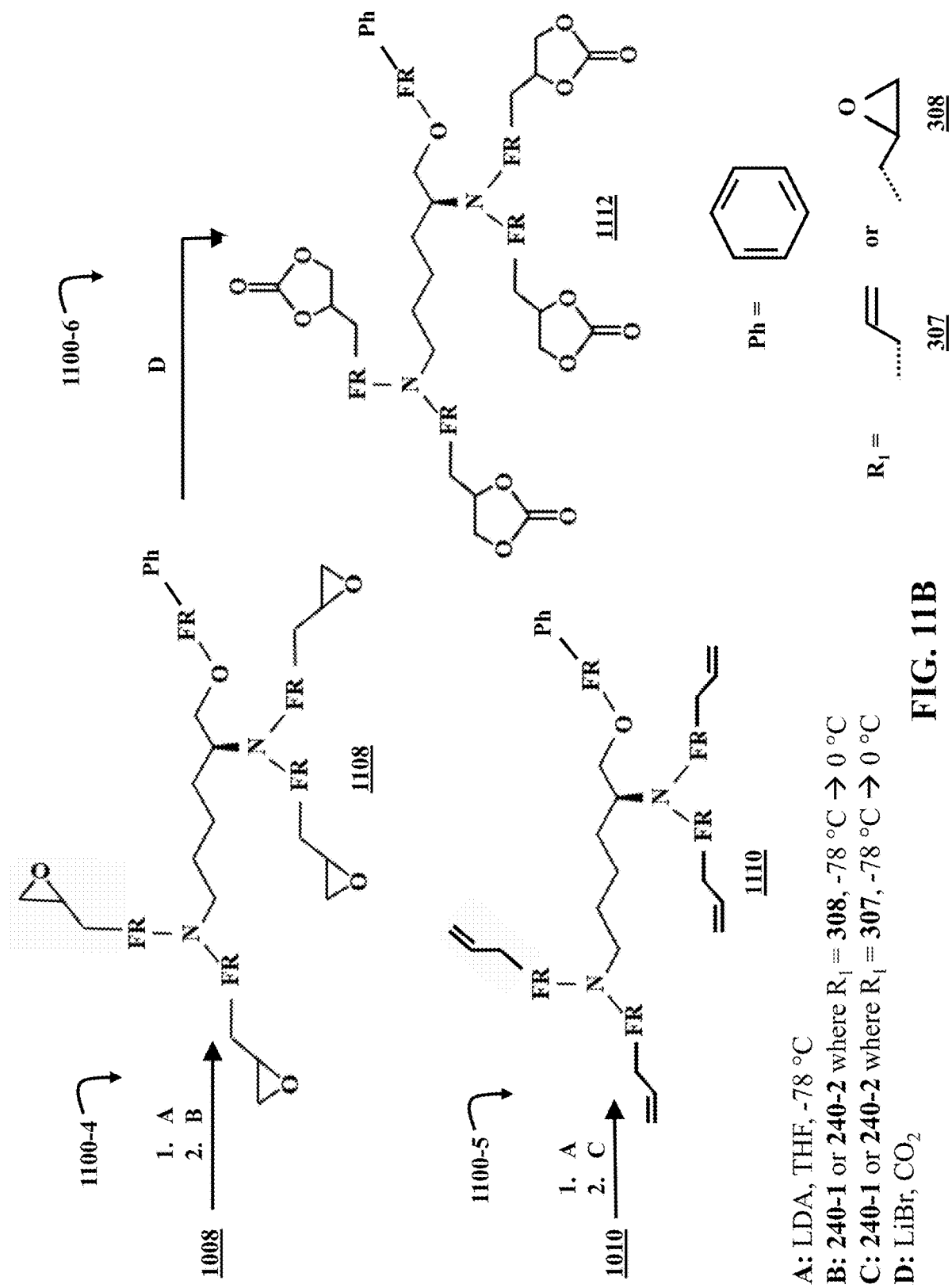
FIG. 11B is a chemical reaction diagram illustrating three processes of forming tetrafunctionalized flame retardant lysine-derived molecules, in accordance with embodiments of the present disclosure.

FIG. 11B is a chemical reaction diagram illustrating three processes 1100-4, 1100-5, and 1100-6 of forming tetrafunctionalized flame retardant reduced lysine-derived molecules 1108, 1110, and 1112, in accordance with embodiments of the present disclosure. In process 1100-4, the epoxy difunctionalized flame retardant reduced lysine-derived molecule 1008 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an epoxy functional group 308 is added to the solution (e.g., dropwise, while stirring). The resulting mixture is then stirred for 16 hours while allowing it to warm gradually to room temperature. This yields an epoxy tetrafunctionalized flame retardant reduced lysine-derived molecule 1108.

In process 1100-5, the allyl difunctionalized flame retardant reduced lysine-derived molecule 1010 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an allyl functional group 307, is added to the solution (e.g., dropwise, while stirring). The resulting mixture is then stirred for 16 hours while allowing it to warm gradually to room temperature. This yields an allyl tetrafunctionalized flame retardant lysine-derived molecule 1110.

In process 1100-6, the epoxy tetrafunctionalized flame retardant reduced lysine-derived molecule 1108 is combined with lithium bromide (LiBr). Carbon dioxide ($CO_2$) is added to the mixture, either by injecting it into the headspace of the reaction flask, or by bubbling it through the solution. This process yields a propylene carbonate tetrafunctionalized flame retardant reduced lysine-derived molecule 1112.

With respect to FIG. 11A and FIG. 11B, the same reaction conditions as implemented in FIG. 8A through 8D can be implemented to synthesize thioether-linked tetrafunctionalized flame retardants. Specifically, allyl tetrafunctionalized flame retardant derivatives 1104 and 1110 can be reacted with thiol-ene molecules mercaptoethanol 410, cysteamine HCl 420, and 3-mercaptopropionate 430 (illustrated in FIG. 4) to yield tetrafunctionalized thioether-linked flame retardant molecules.

Figure 12A:
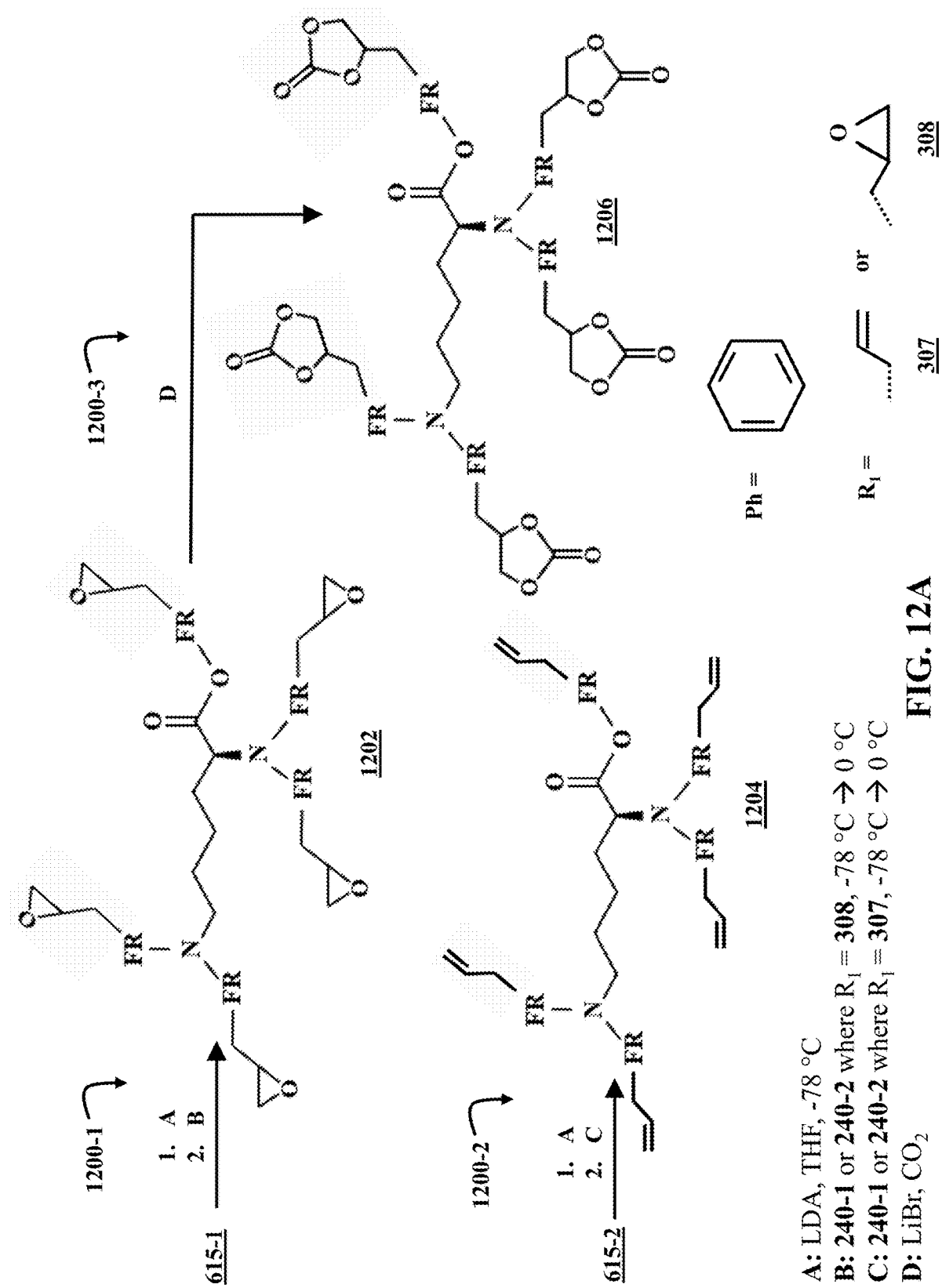
FIG. 12A is a chemical diagram illustrating three processes of forming pentafunctionalized flame retardant lysine-derived molecules, in accordance with embodiments of the present disclosure.

FIG. 12A is a chemical diagram illustrating three processes 1200-1, 1200-2, and 1200-3 of forming pentafunctionalized flame retardant lysine-derived molecules 1202, 1204, and 1206, in accordance with embodiments of the present disclosure. In process 1200-1, the epoxy functionalized flame retardant lysine cross-linker 615-1 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an epoxy functional group 308 is added to the solution (e.g., dropwise, while stirring). The resulting mixture is then stirred for 16 hours while allowing it to warm gradually to room temperature. This yields an epoxy pentafunctionalized flame retardant lysine-derived molecule 1202.

In process 1200-2, the allyl functionalized flame retardant lysine cross-linker 615-2 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an allyl functional group 307 is added to the solution (e.g., dropwise, while stirring). The resulting mixture is then stirred for 16 hours while allowing it to warm gradually to room temperature. This yields an allyl pentafunctionalized flame retardant lysine-derived molecule 1204.

In process 1200-3, the epoxy pentafunctionalized flame retardant lysine-derived molecule 1202 is combined with lithium bromide (LiBr). Carbon dioxide ($CO_2$) is added to the mixture, either by injecting it into the headspace of the reaction flask, or by bubbling it through the solution. This process yields a propylene carbonate pentafunctionalized flame retardant lysine-derived molecule 1206.

Figure 12B:
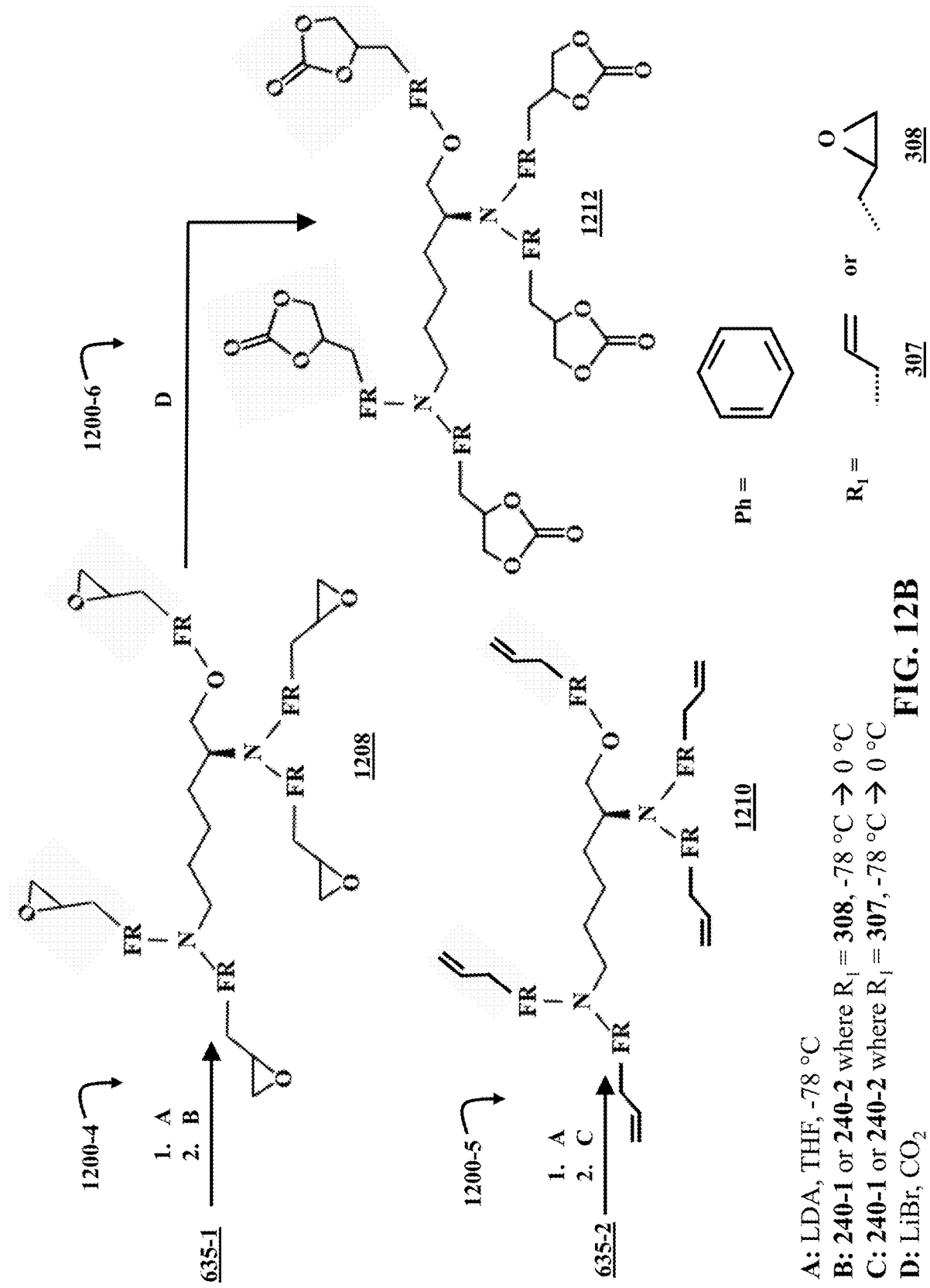
FIG. 12B is a chemical reaction diagram illustrating three processes of forming pentafunctionalized flame retardant reduced lysine-derived molecules, in accordance with embodiments of the present disclosure.

FIG. 12B is a chemical reaction diagram illustrating three processes 1200-4, 1200-5, and 1200-6 of forming pentafunctionalized flame retardant reduced lysine derived molecules 1208, 1210, and 1212, in accordance with embodiments of the present disclosure. In process 1200-4, the epoxy functionalized flame retardant reduced lysine cross-linker 635-1 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an epoxy functional group 308 is added to the solution (e.g., dropwise, while stirring). The resulting mixture is then stirred for 16 hours while allowing it to warm gradually to room temperature. This yields an epoxy pentafunctionalized flame retardant reduced lysine-derived molecule 1208.

In process 1200-5, the allyl functionalized flame retardant reduced lysine cross-linker 635-2 is reacted with either lithium diisopropylamine (LDA) or lithium bis(trimethylsilyl) amide in a tetrahydrofuran (THF) solution of approximately −78° C. The resulting mixture is stirred for 30 minutes. Afterwards, the phosphorus-based flame retardant molecule 240, where the $R_1$ functional group is an allyl functional group 307 is added to the solution (e.g., dropwise, while stirring). The resulting mixture is then stirred for 16 hours while allowing it to warm gradually to room temperature. This yields an allyl pentafunctionalized flame retardant reduced lysine-derived molecule 1210.

In process 1200-6, the epoxy pentafunctionalized flame retardant reduced lysine-derived molecule 1208 is combined with lithium bromide (LiBr). Carbon dioxide ($CO_2$) is added to the mixture, either by injecting it into the headspace of the reaction flask, or by bubbling it through the solution. This process yields a propylene carbonate pentafunctionalized flame retardant reduced lysine-derived molecule 1212.

With respect to FIG. 12A and FIG. 12B, the same reaction conditions as implemented in FIG. 8A through 8D can be implemented to synthesize thioether-linked pentafunctionalized flame retardants. Specifically, allyl pentafunctionalized flame retardant derivatives 1204 and 1210 can be reacted with thiol-ene molecules mercaptoethanol 410, cysteamine HCl 420, and 3-mercaptopropionate 430 (illustrated in FIG. 4) to yield pentafunctionalized thioether-linked flame retardant molecules.

With reference to the FIGS. 6-12, in some embodiments meta-chloroperoxybenzoic acid (mCPBA) can be used to oxidize allyl $R_1$ functional groups 307 into epoxy $R_1$ functional groups 308, as opposed to binding the allyl groups directly to the precursor molecules (e.g., lysine 505, reduced lysine 515, proline 510, and reduced proline 520). For example, flame retardant molecules 615-2, 635-2, 620-2, and 640-2 can be converted into flame retardant molecules 615-1, 635-1, 620-1, and 640-1 via reaction with mCPBA. These mCPBA reactions can be completed with any allyl functionalized flame retardant molecule, including ally difunctionalized, trifunctionalized, tetrafunctionalized, and pentafunctionalized molecules.

Further, in some embodiments, stoichiometric trimethylamine is used instead of DMAP to phosphorylate the amino/hydroxyl functional groups. In some embodiments, phosphorylating amines/hydroxyl functional groups includes reacting the selected precursor and flame retardant molecule in a solution containing water ($H_2O$), ethanol (EtOH), carbon tetrachloride ($CCl_4$), and trimethylamine ($Et_3N$) for 2 hours at a temperature of approximately 0-20° C.

In some embodiments, secondary amine molecules (e.g., 615 and 635) are formed via reaction of primary amines (e.g., 505 and 515) with $Et_3N$ and toluene. In an example, lysine 505 is reacted with $Et_3N$ and the phosphorus-based flame retardant molecule 240 in a toluene solution at 60° C. to form the trifunctionalized flame retardant lysine cross-linker 615. As another example, reduced lysine 515 is reacted with $Et_3N$ and the phosphorus-based flame retardant molecule 240 in a toluene solution at 60° C. to form the trifunctionalized flame retardant reduced lysine cross-linker 635.

In some embodiments, tertiary amine molecules (e.g., 1102, 1104, 1108, and 1110) are formed via reaction of secondary amines (e.g., 1002, 1004, 1008, and 1010) with Et$_3$N and toluene. In an example, the epoxy difunctionalized flame retardant lysine-derived molecule 1002 is reacted with Et$_3$N and the phosphorus-based flame retardant molecule 240, where R$_1$ is the epoxy functional group 308, in a toluene solution at 110° C. for 5 hours to form the epoxy tetrafunctionalized flame retardant lysine-derived molecule 1102.

Figure 13:
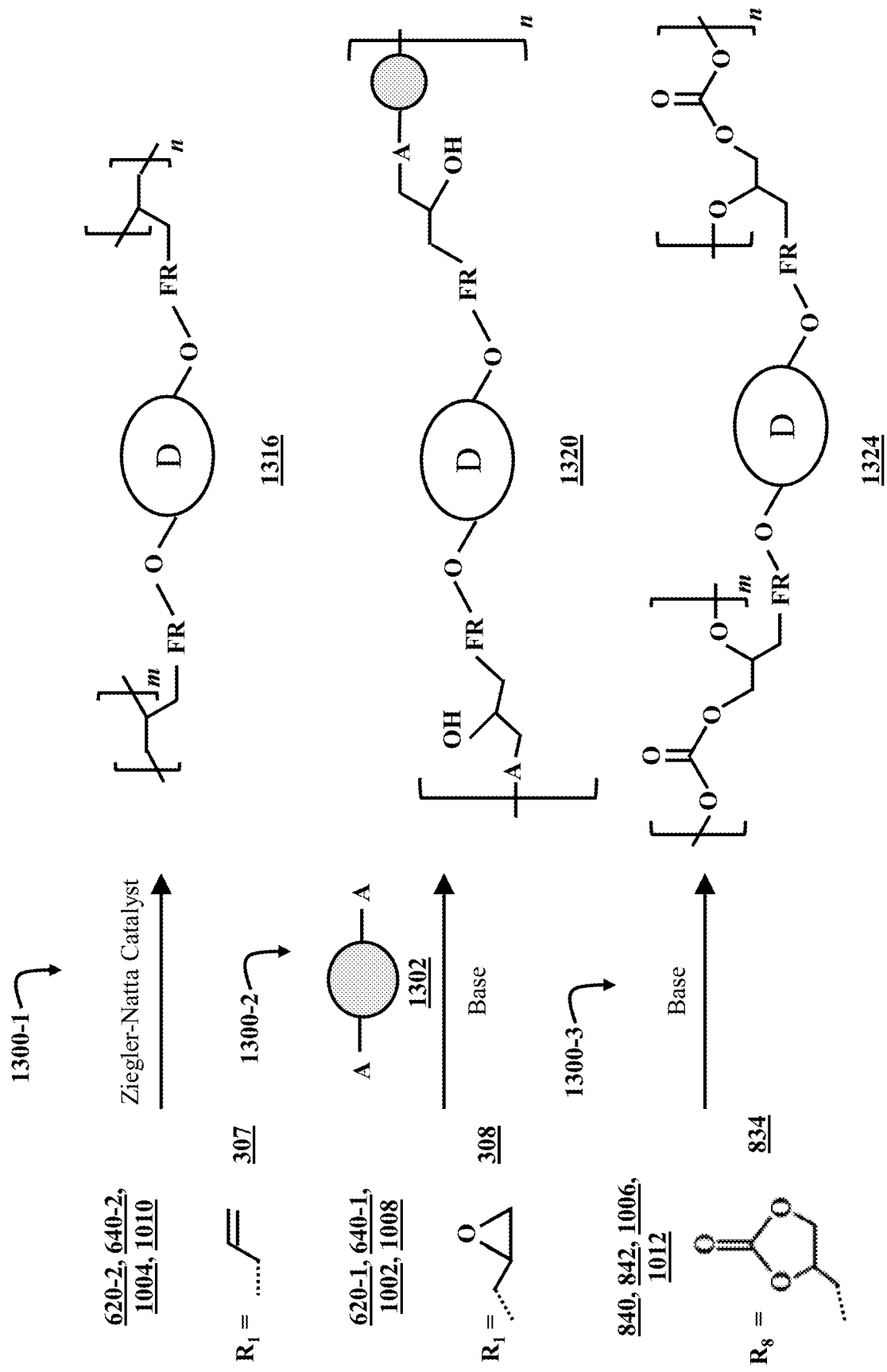
FIG. 13 is a chemical reaction diagram illustrating processes of synthesizing flame retardant lysine-based, reduced lysine-based, proline-based, or reduced proline-based polymers from flame retardant lysine-derived, reduced lysine-derived, proline-derived, or reduced proline-derived monomers, in accordance with embodiments of the present disclosure.

FIG. 13 is a chemical reaction diagram illustrating three processes 1300-1, 1300-2, and 1300-3 of synthesizing flame retardant lysine-based, reduced lysine-based, proline-based, or reduced proline-based polymers 1316, 1320, and 1324 from flame retardant lysine-derived, reduced lysine-derived, proline-derived, or reduced proline-derived monomers, in accordance with embodiments of the present disclosure. Each structure shows only the ligands with R functional groups (i.e., allyl, epoxy, or propylene carbonate). An oval labeled "D" represents the lysine-derivative, reduced lysine-derivative, proline-derivative, or reduced proline-derivative core of each monomer. The reactions illustrated herein are prophetic examples of polymers that can be synthesized from the flame retardant lysine-derived, reduced lysine-derived, proline-derived, or reduced proline-derived monomers, but other polymers can be produced as well (e.g., by changing reaction conditions, co-monomers, R groups, etc.).

Processes 1300-1, 1300-2, and 1300-3 illustrate the polymerization of difunctionalized flame retardant lysine-derived molecules, reduced lysine-derived molecules, proline-derived molecules, or reduced proline-derived molecules 620, 640, 840, 842, 1002, 1004, 1006, 1008, 1010, 1012 only. However, it should be noted that each of these polymerization reactions can also be carried out with the trifunctionalized flame retardant lysine and reduced lysine-derived molecules (e.g., 615, 635, 836, and 838), tetrafunctionalized flame retardant lysine and reduced lysine-derived molecules (e.g., 1102, 1104, 1106, 1108, 1110, and 1112), and pentafunctionalized flame retardant lysine and reduced lysine-derived molecules (e.g., 1202, 1204, 1206, 1208, 1210, and 1212). Further, processes 1300-1 and 1300-3 may similarly be carried out with monofunctionalized flame retardant lysine, reduced lysine, proline, and reduced proline-derived molecules (e.g., 904, 906, 910, 912, 916, 918, 922, 924, 928, 930, 934, and 936).

In some embodiments, the polymerization reactions are carried out with a combination of mono-, di-, tri-, tetra-, and/or pentafunctionalized monomers. Any combination of these monomers may be polymerized. Further, any ratio of monomers may be combined.

In process 1300-1, allyl-derived flame retardant lysine, reduced lysine, proline, and reduced proline based polymers 1316 are formed from allyl difunctionalized flame retardant proline-derived molecules 620-2, reduced proline-derived molecules 640-2, lysine-derived molecules 1004, and reduced lysine-derived molecules 1010. The allyl difunctionalized flame retardant proline-derived molecules 620-2, reduced proline-derived molecules 640-2, lysine-derived molecules 1004, or reduced lysine-derived molecules 1010 are reacted with a Ziegler-Natta catalyst. Ziegler-Natta catalysts catalyze the polymerization of 1-alkenes. Examples of these catalysts can include heterogeneous Ziegler-Natta catalysts based on titanium compounds and homogeneous Ziegler-Natta catalysts based on complexes of titanium, zirconium, or hafnium. Heterogeneous and homogeneous Ziegler-Natta catalysts can be used in combination with organoaluminum co-catalysts in some embodiments.

In process 1300-2, epoxy-derived flame retardant lysine, reduced lysine, proline, and reduced proline based polymers 1320 are formed from epoxy difunctionalized flame retardant proline-derived molecules 620-1, reduced proline-derived molecules 640-1, lysine-derived molecules 1002, and reduced lysine-derived molecules 1008. The epoxy difunctionalized flame retardant proline-derived molecules 620-1, reduced proline-derived molecules 640-1, lysine-derived molecules 1002, and reduced lysine-derived molecules 1008 are reacted with a base and a second monomer 1302. The second monomer 1302 is a compound with at least two hydroxyl (OH) groups or at least two amino (NH$_2$) groups (e.g., a diol, polyol, diamine, polyamine, etc.). These compounds 1302 are illustrated as a gray oval with attached A groups. The A group represents a hydroxyl group or an amino group. It should be noted that, while two A groups are illustrated herein, there are more than two A groups in some embodiments. Additionally, in some embodiments, the epoxy difunctionalized proline-derived molecules 620-1, reduced proline-derived molecules 640-1, lysine-derived molecules 1002, and reduced lysine-derived molecules 1008 self-polymerize under basic conditions. In these instances, the reaction does not include the second monomer 1302.

In process 1300-3, propylene carbonate-derived flame retardant lysine, reduced lysine, proline, and reduced proline based polymers 1324 are formed from propylene carbonate-difunctionalized flame retardant proline-derived molecules 840, reduced proline-derived molecules 842, lysine-derived molecules 1006, and reduced lysine-derived molecules 1012. The propylene carbonate difunctionalized flame retardant proline-derived molecules 840, reduced proline-derived molecules 842, lysine-derived molecules 1006, or reduced lysine-derived molecules 1012 are reacted in a ring-opening polymerization initiated by a base. Examples of bases that can be used as initiators can include potassium hydroxide (KOH), sodium hydroxide (NaOH), lithium hydroxide (LiOH), etc.

In addition to the polymers illustrated in FIG. 13, the flame retardant lysine-derivatives, reduced lysine-derivatives, proline-derivatives, or reduced proline-derivatives disclosed herein can be used in the synthesis of other flame retardant polymers, in some embodiments. An array of classes of flame retardant polymers can be made with different combinations of monomers. These polymerization processes are in accordance with polymer chemistry platforms that can include polyhydroxyurethanes, polycarbonates, polymers obtained by radical polymerization, polyurethanes, polyesters, polyacrylates, polycarbonates, epoxy resins, polyimides, polyureas, polyamides, poly(vinyl-esters), etc.

One example of an application of polymers made, at least in part, from flame retardant lysine-derivatives, reduced lysine-derivatives, proline-derivatives, or reduced proline-derivatives is in plastics used in electronics hardware. Additional applications can include acoustic dampening, cushioning, plastics, synthetic fibers, insulation, etc. The flame retardant lysine-derivatives, reduced lysine-derivatives, proline-derivatives, or reduced proline-derivatives can also be used to make adhesives such as bio-adhesives, elastomers, thermoplastics, emulsions, thermosets, etc. Further, materials containing the flame retardant lysine-derivatives, reduced lysine-derivatives, proline-derivatives, or reduced proline-derivatives can be incorporated into various devices with electronic components that can include printed circuit boards (PCBs), semiconductors, transistors, optoelectronics, capacitors, resistors, etc.

Resins for printed circuit boards (PCBs) can be made flame retardant by incorporating polymers that are made, at least in part, from lysine-derivatives, reduced lysine-derivatives, proline-derivatives, or reduced proline-derivatives. PCBs are electrical circuits that can be found in most types of electronic devices, and they support and electronically connect electrical components in the device. PCBs are formed by etching a copper conductive layer laminated onto an insulating substrate. The insulating substrate can be a laminate comprising a resin and a fiber. Many resins in PCBs contain a polymer, such as an epoxy, a polyhydroxyurethane, a polycarbonate, a polyester, a polyacrylate, a polyimide, a polyamide, a polyurea, a poly(vinyl-ester), etc. Using polymers that incorporate the flame retardant lysine-derivatives, reduced lysine-derivatives, proline-derivatives, or reduced proline-derivatives can prevent the PCB from catching fire when exposed to high temperature environments or electrical power overloads.

It should be noted that, in some embodiments, the compounds described herein can contain one or more chiral centers. These can include racemic mixtures, diastereomers, enantiomers, and mixtures containing one or more stereoisomer. Further, the disclosed can encompass racemic forms of the compounds in addition to individual stereoisomers, as well as mixtures containing any of these.

The synthetic processes discussed herein and their accompanying drawings are prophetic examples, and are not limiting; they can vary in reaction conditions, components, methods, etc. In addition, the reaction conditions can optionally be changed over the course of a process. Further, in some embodiments, processes can be added or omitted while still remaining within the scope of the disclosure, as will be understood by a person of ordinary skill in the art.

What is claimed is:

1. A flame retardant lysine-derived molecule with a formula of:

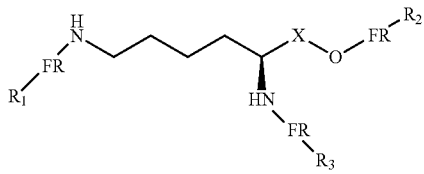

wherein X is selected from a group consisting of a methanediyl moiety and a carbonyl moiety;
wherein FR is a phosphorus-based moiety;
wherein $R_1$ is a substituent selected from a group consisting of an allyl substituent, an epoxide substituent, a propylene carbonate substituent, and a thioether substituent;
wherein $R_2$ is a substituent selected from a group consisting of an allyl substituent, an epoxide substituent, a propylene carbonate substituent, and a thioether substituent; and
wherein $R_3$ is a substituent selected from a group consisting of an allyl substituent, an epoxide substituent, a propylene carbonate substituent, and a thioether substituent.

2. The flame retardant lysine-derived molecule of claim 1, wherein the FR is a phosphoryl moiety with a formula of:

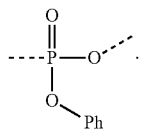

3. The flame retardant lysine-derived molecule of claim 1, wherein the FR is a phosphonyl moiety with a formula of:

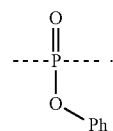

4. A flame retardant proline-derived molecule with a formula of:

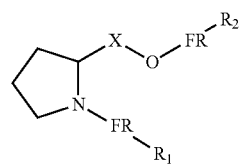

wherein X is selected from a group consisting of a methanediyl moiety and a carbonyl moiety;
wherein FR is a phosphorus-based moiety;
wherein $R_1$ is a substituent selected from a group consisting of an allyl substituent, an epoxide substituent, a propylene carbonate substituent, and a thioether substituent; and
wherein $R_2$ is a substituent selected from a group consisting of an allyl substituent, an epoxide substituent, a propylene carbonate substituent, and a thioether substituent.

5. The flame retardant proline-derived molecule of claim 4, wherein the FR is a phosphoryl moiety with a formula of:

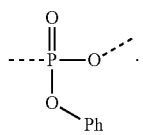

6. The flame retardant proline-derived molecule of claim 4, wherein the FR is a phosphonyl moiety with a formula of:

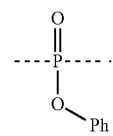

7. An article of manufacture, comprising a material containing a flame retardant lysine-derived molecule with a formula of:

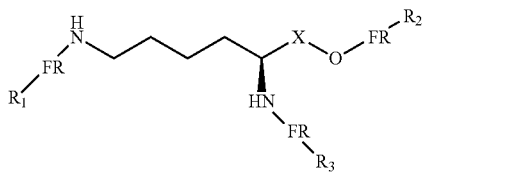

wherein X is selected from a group consisting of a methanediyl moiety and a carbonyl moiety;

wherein FR is a phosphorus-based moiety;

wherein $R_1$ is a substituent selected from a group consisting of an allyl substituent, an epoxide substituent, a propylene carbonate substituent, and a thioether substituent;

wherein $R_2$ is a substituent selected from a group consisting of an allyl substituent, an epoxide substituent, a propylene carbonate substituent, and a thioether substituent; and wherein $R_3$ is a substituent selected from a group consisting of an allyl substituent, an epoxide substituent, a propylene carbonate substituent, and a thioether substituent.

wherein the article of manufacture further comprises a printed circuit board (PCB).

* * * * *